United States Patent
Ahangari et al.

(10) Patent No.: US 12,060,555 B2
(45) Date of Patent: Aug. 13, 2024

(54) MicroRNA-33 INHIBITORS AND USE THEREOF IN THE TREATMENT OF PULMONARY FIBROSIS

(71) Applicants: Yale University, New Haven, CT (US); University of Connecticut, Farmington, CT (US)

(72) Inventors: Farida Ahangari, New Haven, CT (US); Naftali Kaminski, New Haven, CT (US); Carlos Fernandez-Hernando, New Haven, CT (US); Raman Bahal, Glastonbury, CT (US)

(73) Assignees: YALE UNIVERSITY, New Haven, CT (US); UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 17/663,378

(22) Filed: May 13, 2022

(65) Prior Publication Data
US 2022/0364083 A1    Nov. 17, 2022

Related U.S. Application Data

(60) Provisional application No. 63/188,759, filed on May 14, 2021.

(51) Int. Cl.
  *C12N 15/113* (2010.01)
  *A61K 31/713* (2006.01)
  *A61P 9/10* (2006.01)
  *C12N 15/11* (2006.01)

(52) U.S. Cl.
  CPC .......... *C12N 15/111* (2013.01); *A61K 31/713* (2013.01); *A61P 9/10* (2018.01); *C12N 15/113* (2013.01)

(58) Field of Classification Search
  CPC ....... C12N 15/111; C12N 15/113; A61P 9/10; A61K 31/713
  USPC ...................................................... 514/44 A
  See application file for complete search history.

(56) References Cited

U.S. PATENT DOCUMENTS 9,241,950 B2    1/2016 Moore et al.
2012/0053227 A1*  3/2012 Fernandez-Hernando ..................
                                              C12N 15/113
                                              514/44 A

OTHER PUBLICATIONS

Barna BP, McPeek M, Malur A, Fessler MB, Wingard CJ, Dobbs L, Verbanac KM, Bowling M, Judson MA, Thomassen MJ. Elevated MicroRNA-33 in Sarcoidosis and a Carbon Nanotube Model of Chronic Granulomatous Disease. Am J Respir Cell Mol Biol. Jun. 2016;54(6):865-71. doi: 10.1165/rcmb.2015-0332OC. (Year: 2015).*
Miguel V, Rey C, Aceña JL, Maqueda F, Fernández-Hernando C, Rodríguez-Puyol D, Vaquero JJ, Lamas S. The pHLIP system as a vehicle for microRNAs in the kidney. Nefrologia (Engl Ed). Sep.-Oct. 2020;40(5):491-498. English, Spanish. doi: 10.1016/j.nefro.2020.05.007. Epub Jul. 18, 2020. PMID: 32693933. (Year: 2020).*
F. Ahangari, N.L. Price, G. Ibarra, G. Yu, J.C. Schupp, C. Fernandez-Hernando, N. Kaminski.MiR-33, a MicroRNA Family Linking Metabolic Pathways and Fibrosis in Lung. American Journal of Respiratory and Critical Care Medicine 2018;197:A2203. Poster Presentation. (Year: 2018).*
Price, et al. "Genetic deficiency or pharmacological inhibition of miR-33 protects from kidney fibrosis." JCI insight 4.22 (2019).
Farida Ahangari, MD "Cell Specific microRNA Silencing—A Novel Therapeutic Approach in Pulmonary Fibrosis" Public Presentation on May 20, 2020 for Boehringer Ingelheim Discovery Award.

* cited by examiner

*Primary Examiner* — J. E. Angell
(74) *Attorney, Agent, or Firm* — Saul Ewing LLP; Kathryn Doyle; Domingos J. Silva

(57) ABSTRACT

In one aspect, the present disclosure provides a microRNA-33 (miR-33) inhibitor comprising a peptide nucleic acid covalently bound to a pH low insertion peptide. In another aspect, the present disclosure provides a method of treating pulmonary fibrosis in a subject, the method comprising administering to the subject a therapeutically effective amount of the miR-33 inhibitor. In some embodiments, the pulmonary fibrosis is idiopathic pulmonary fibrosis.

8 Claims, 47 Drawing Sheets
Specification includes a Sequence Listing.

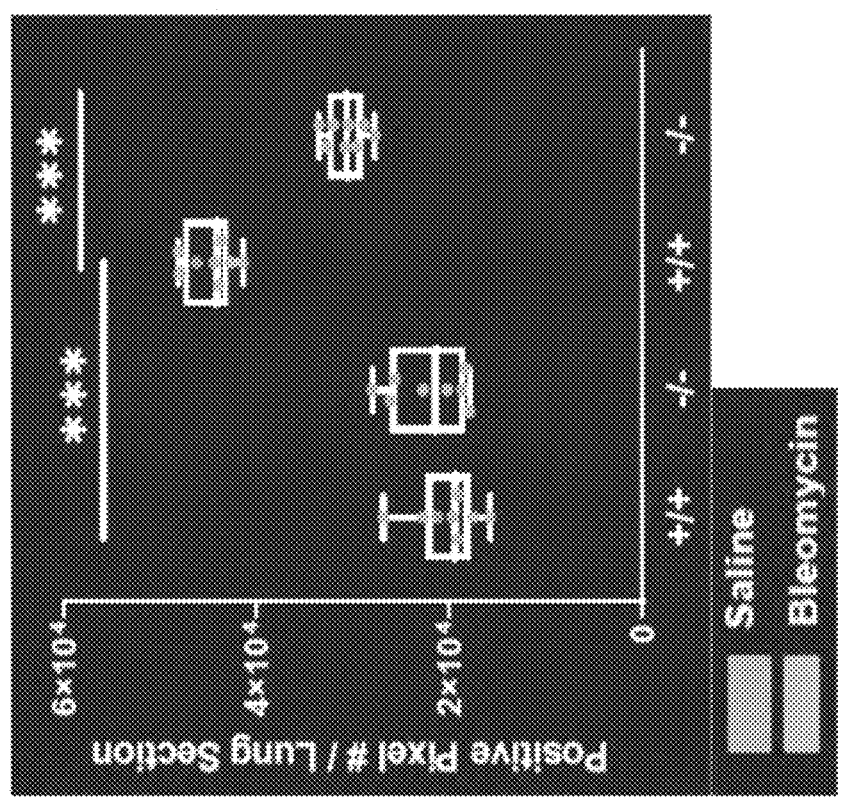
FIG. 8
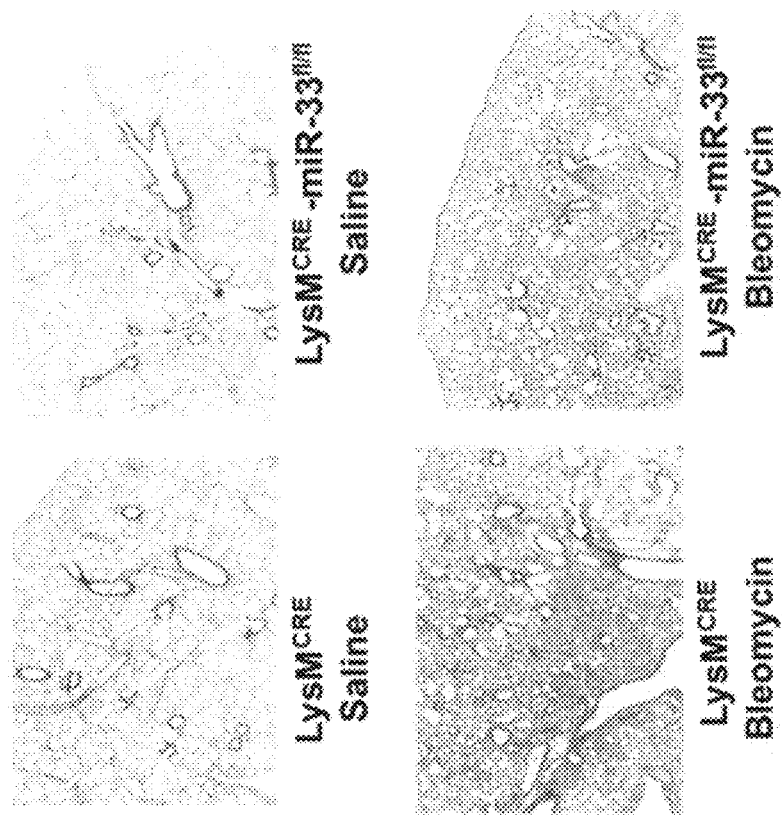

FIG. 12
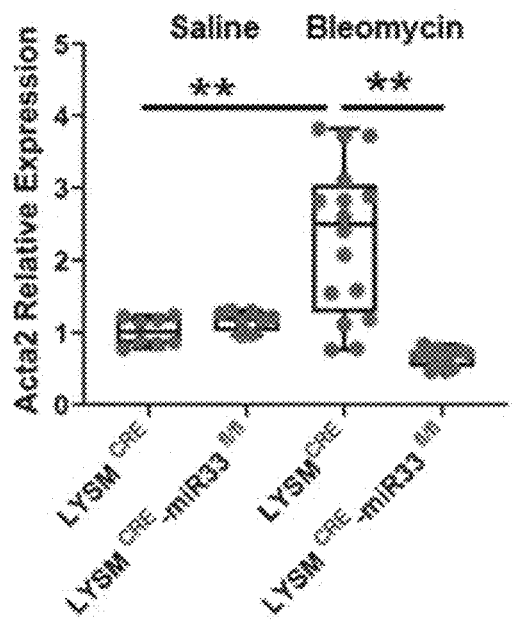
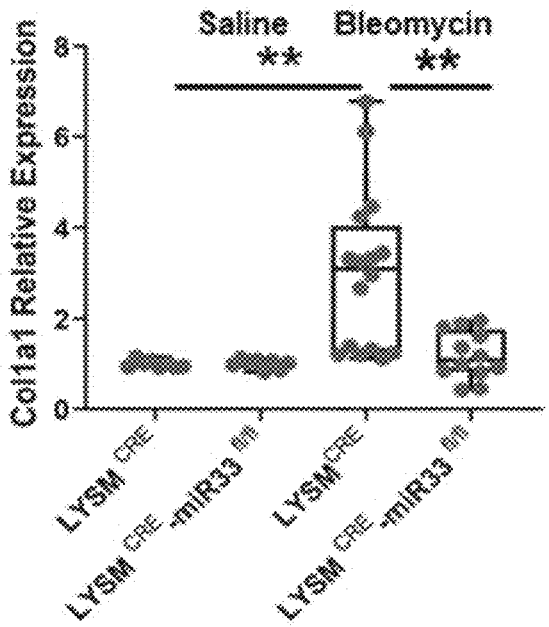
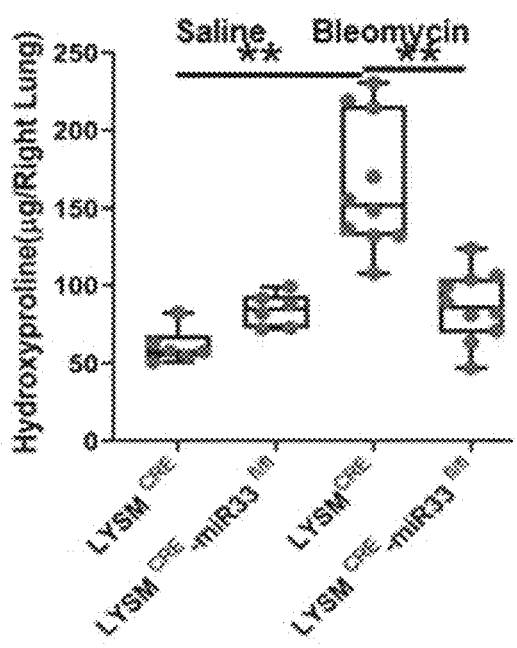
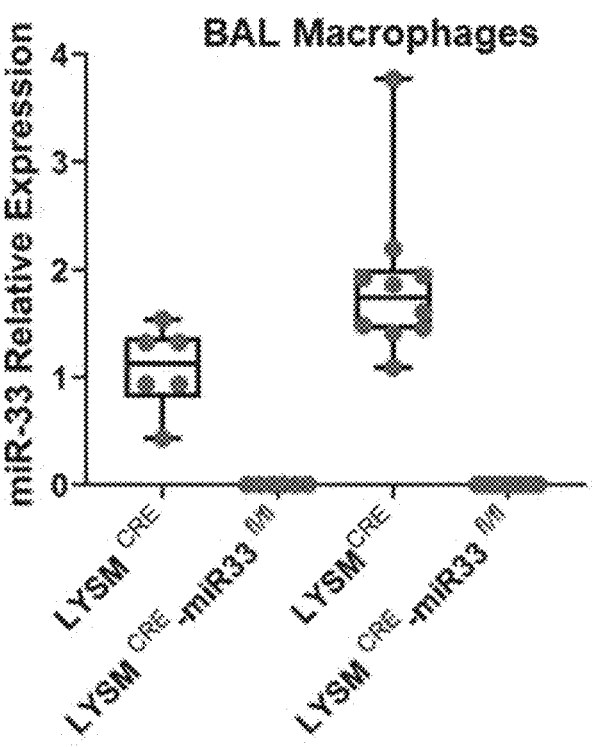

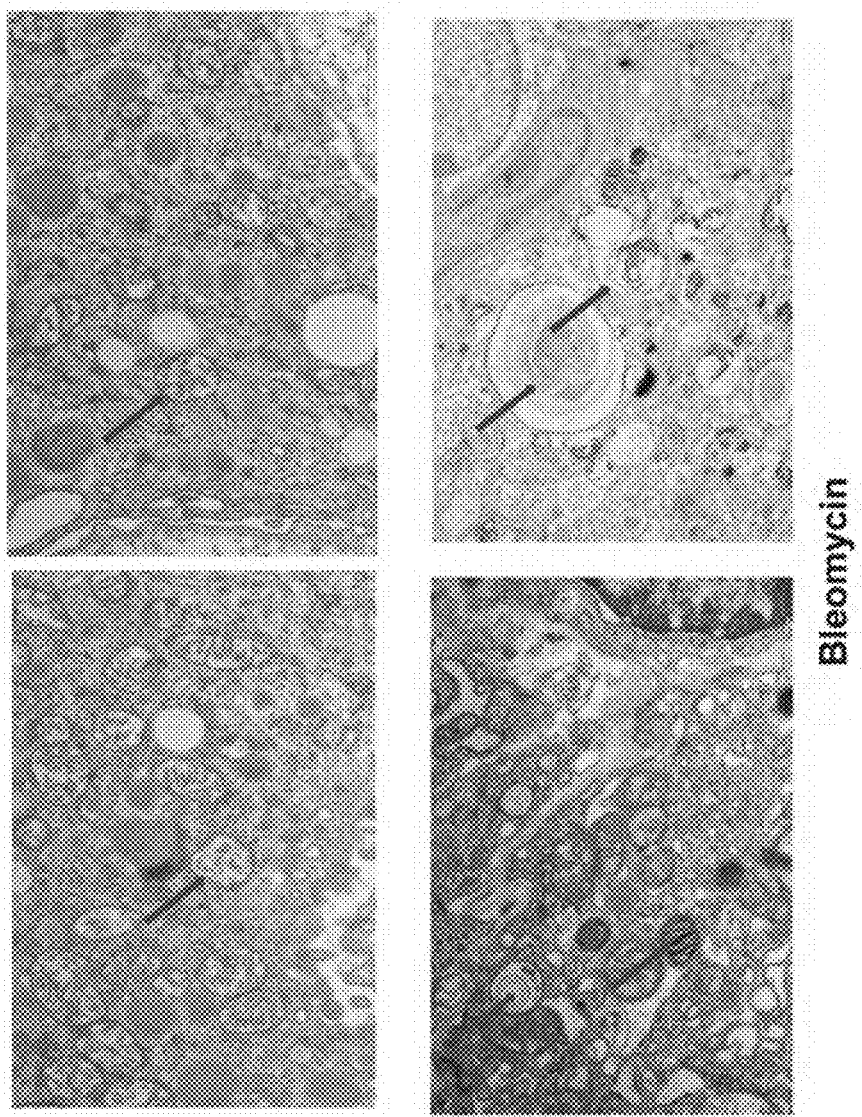
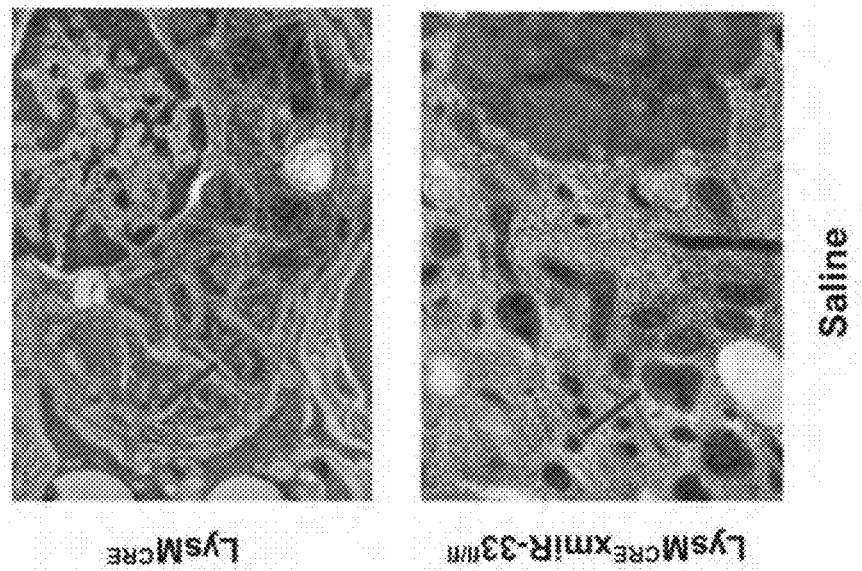
FIG. 13A

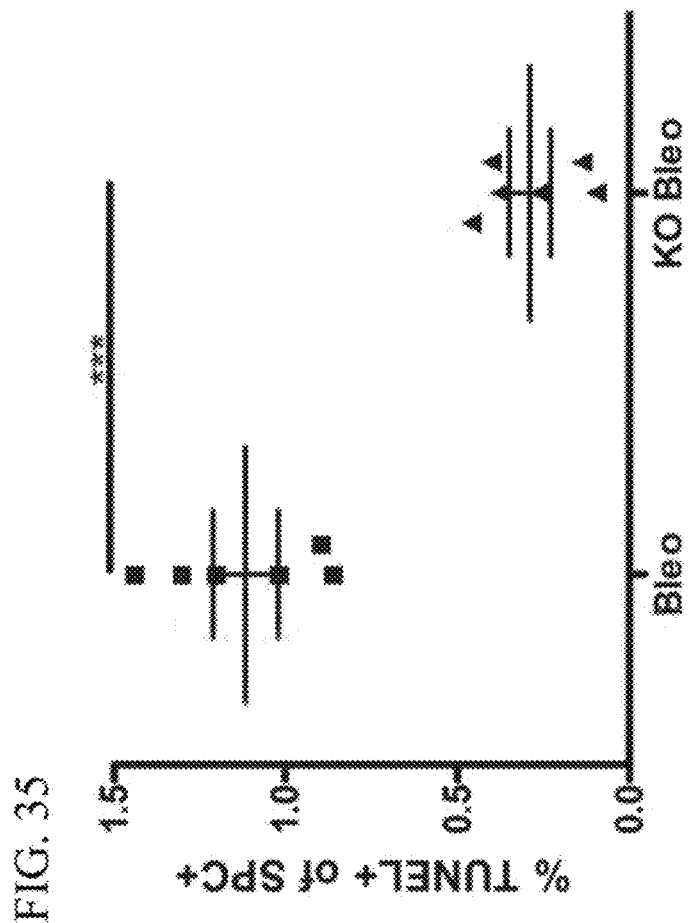
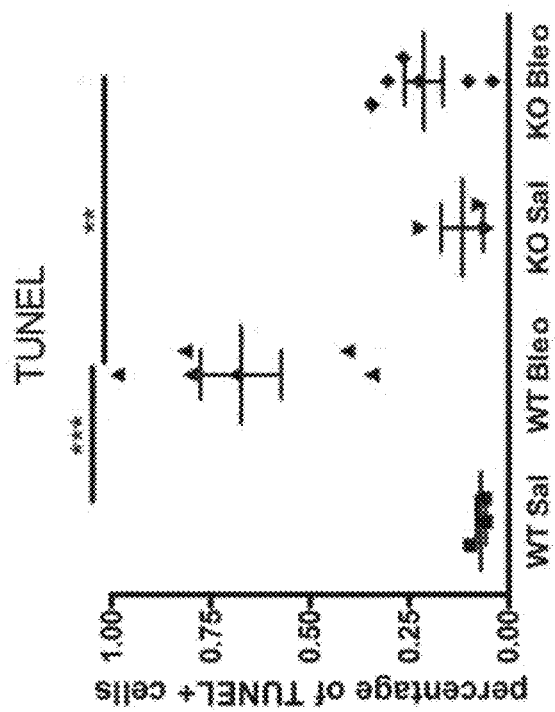
FIG. 35

FIG. 37
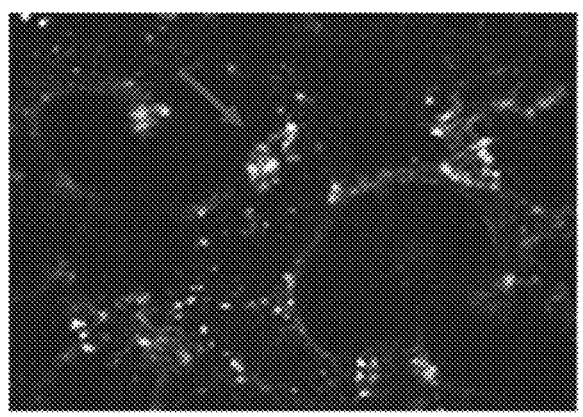
FIG. 38
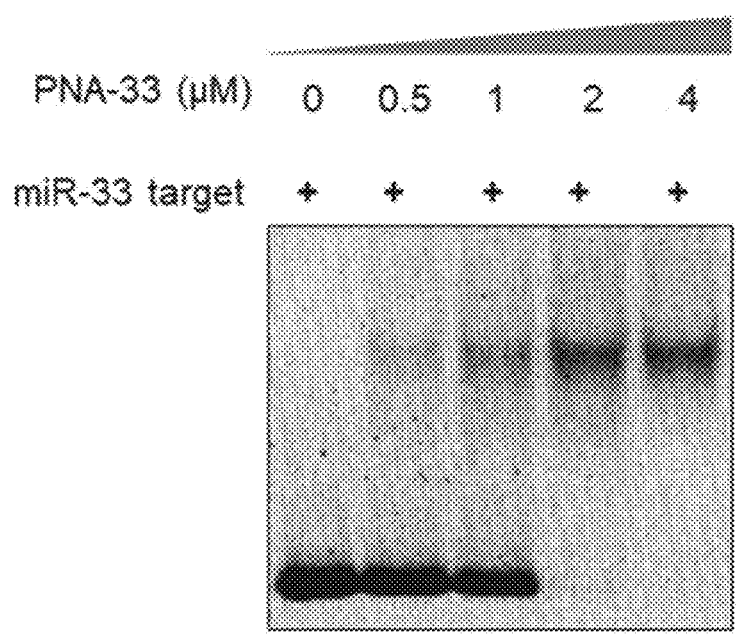

MicroRNA-33 INHIBITORS AND USE THEREOF IN THE TREATMENT OF PULMONARY FIBROSIS

CROSS-REFERENCE TO RELATED APPLICATIONS

The present application claims priority under 35 U.S.C. § 119(e) to U.S. Provisional Patent Application No. 63/188,759, filed May 14, 2021, which is incorporated herein by reference in its entirety.

STATEMENT REGARDING FEDERALLY SPONSORED RESEARCH

This invention was made with government support under HL141852 awarded by National Institutes of Health. The government has certain rights in the invention.

BACKGROUND

Idiopathic pulmonary fibrosis (IPF) is a chronic, progressive, and fatal disease with unknown etiology. The phenotypic changes in IPF include aberrant remodeling and profound changes in all lung cells including alveolar epithelial cells, lung fibroblasts, and macrophages, along with excessive deposition of extracellular matrix proteins in the interstitial space of the lung. IPF is characterized by aberrant wound healing caused by repetitive alveolar epithelial cell injury and excessive deposition of extracellular matrix proteins in the interstitial space of the lung. Median survival of IPF is 3 to 5 years after initial diagnosis and its incidence continues to rise.

There is a need in the art for compounds that can treat, ameliorate, and/or prevent pulmonary fibrosis as well as methods of using these compounds to treat, ameliorate, and/or prevent pulmonary fibrosis a subject. The present invention satisfies these unmet needs.

SUMMARY

In some aspects, the instant specification is directed to a method of treating, ameliorating, and/or preventing pulmonary fibrosis in a subject.

In some embodiments, the method includes administering to the subject a therapeutically effective amount of a microRNA-33 (miR-33) inhibitor via a mode of administration selected from nasal, pulmonary, aerosol, inhalational, intratracheal, intrabronchial, intraperitoneal, intravenous, and oral gavage.

In some embodiments, the miR-33 inhibitor is an antisense peptide nucleic acid (PNA) including a peptide backbone modified with at least nine nucleobases that are complementary to at least nine contiguous nucleotides in miR-33.

In some embodiments, the miR-33 inhibitor includes a structure of formula (I)

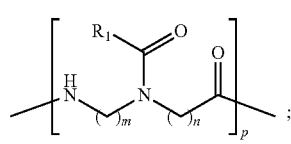

formula (I)

wherein:
each $R_1$ is independently $(CH_2)_q$-nucleobase;
m, n, and q are each independently an integer from 1 to 3;
p is an integer from 5 to 50; and
wherein the nucleobase is selected from adenine, guanine, cysteine, thymine, and uracil such that adjacent nucleobases are complementary to contiguous nucleotides in miR-33.

In some embodiments, in formula (I), m is 2, n is 1, and each q is 1.

In some embodiments, in formula (I), p is an integer from 9 to 17.

In some embodiments, in formula (I), p is 17.

In some embodiments, the nucleobases include the sequence 5'-ATGCAACTACAATGCAA-3' (SEQ ID NO: 1) or the sequence 5'-ATGCAACTACAATGCAA-Cys-SH-3' (SEQ ID NO: 2).

In some embodiments, the structure of formula (I) is linked to a pH low insertion peptide (pHLIP).

In some embodiments, the pulmonary fibrosis is idiopathic pulmonary fibrosis.

In some embodiments, the miR-33 inhibitor is administered to the subject intranasally.

In some embodiments, the miR-33 inhibitor dissolved in saline is administered directly to the lungs of the subject through the subject's nose.

BRIEF DESCRIPTION OF THE DRAWINGS

The following detailed description of exemplary embodiments of the invention will be better understood when read in conjunction with the appended drawings. For the purpose of illustrating the invention, non-limiting embodiments are shown in the drawings. It should be understood, however, that the invention is not limited to the precise arrangements and instrumentalities of the embodiments shown in the drawings.

FIG. 8 shows Masson-Trichrome staining of lung tissues demonstrating that macrophage specific miR-33 KO (LysM$_{CRE}$xmiR-33$^{fl/fl}$) is protective against bleomycin-induced pulmonary fibrosis, in accordance with some embodiments.

FIG. 12 shows that macrophage specific miR-33 KO is protective against bleomycin-induced pulmonary fibrosis, in accordance with some embodiments.

FIGS. 13A-13B and FIG. 14 depict that the absence of miR-33 in macrophages enhances mitochondrial homeostasis and autophagy after bleomycin injury, in accordance with some embodiments. FIG. 13B depicts that, in macrophage specific MiR-33 KO mice after bleomycin, the mitochondria maintain their normal looking structures and autophagosomes are dramatically increased (red arrows: mitochondria, white arrows: autophagosomes).

FIG. 33, FIG. 34, and FIG. 35 show that the absence of miR-33 in macrophages reduces bleomycin-induced cell death in AEC-II cells, in accordance with some embodiments.

FIG. 37 is two-photon images of mice lungs after IV and IT injection of pHLIP-PNA-TAMRA conjugated, showing the accumulation of the dye inside the macrophages, in accordance with some embodiments.

FIG. 38 is a gel-shift assay following annealing of miR-33 target with PNA-33 at different concentrations, in accordance with some embodiments.

DETAILED DESCRIPTION OF THE DISCLOSURE

Figure 1B:
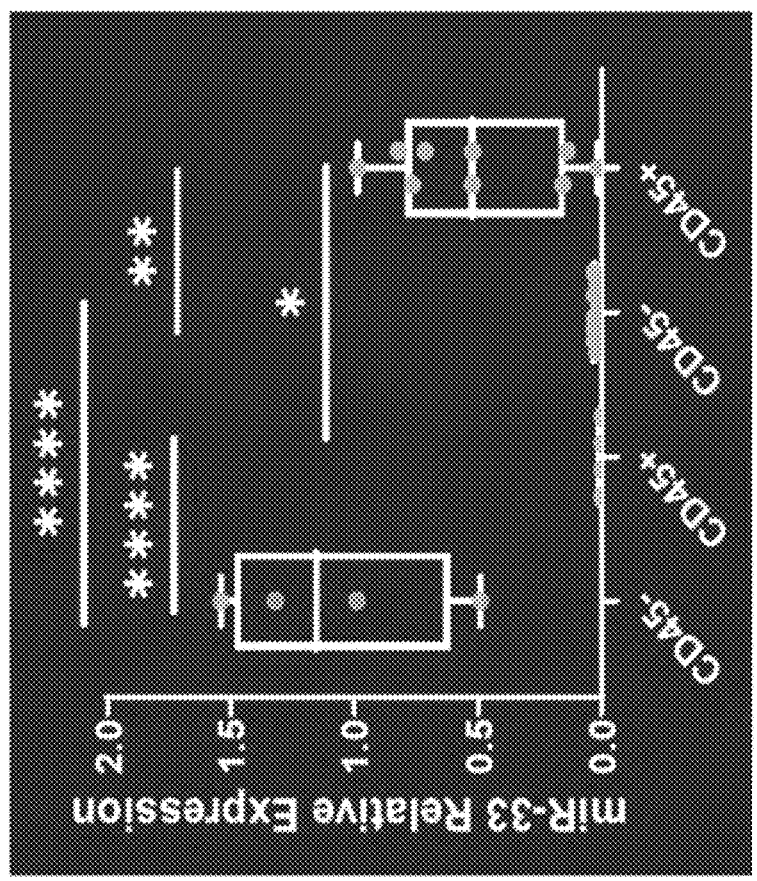
FIG. 1B depicts that miR-33 is increased in monocytes isolated from IPF patients compared to controls, in accordance with some embodiments.

Until recently, there were no effective therapeutic approaches that could alter the course of IPF and prolong a patient's survival, other than lung transplantation, which is available only to a small minority of individuals. In the past decade, researchers have begun to elucidate the mechanism behind the metabolic changes in macrophages and appreciate their impact on lung diseases. In certain embodiments, metabolic reprogramming of mitochondrial dysfunction in all cells, specifically macrophages required for their roles in wound repair and resolution, can provide treatment for IPF.

MiR-33a and miR-33b are intronic microRNAs, which are known as master regulators of sterol and fatty acid metabolism with effects on mitochondrial function. One of the main target genes of miR-33 is peroxisome proliferator-activated receptor gamma coactivator-1α (PPARGC1A or PGC-1α), a gene that plays a central role in regulating cellular energy homeostasis and mitochondrial metabolism, especially in macrophages. PGC-1α, a known marker of mitochondria biogenesis, is decreased in human IPF lungs. Ablation of miR-33 in macrophages promotes mitochondrial biogenesis and efficient production of ATP via a PGC-1α dependent pathway.

It was discovered herein that miR-33 is increased in cells isolated from bronchoalveolar lavage of patients with IPF. In parallel, it was observed that miR-33 knockout mice as well as macrophage-specific knockout mice (LysMCRExmiR-$33^{fl/fl}$) are protected against bleomycin induced pulmonary fibrosis. In certain embodiments, miR-33 contributes to the development of pulmonary fibrosis, by its effects on mitochondrial biogenesis and function in macrophages, and thus a cell specific inhibition of miR-33 can lead to a resolution of pulmonary fibrosis.

The present disclosure provides an miR-33 inhibitor. In some embodiments, the miR-33 inhibitor is an antisense peptide nucleic acid (PNA) comprising a peptide backbone modified with at least ten nucleobases that are complementary to at least ten contiguous nucleotides in miR-33. In some embodiments, the PNA is linked to a pH low insertion peptide (pHLIP). In certain embodiments, the miR-33 inhibitor comprises a structure of formula (I). In some embodiments, the structure of formula (I) is linked to a pHLIP.

The present disclosure further provides a method of treating, ameliorating, and/or preventing pulmonary fibrosis in a subject. In certain embodiments, the method comprises administering to the subject a therapeutically effective amount of an miR-33 inhibitor disclosed herein. In some embodiments, the pulmonary fibrosis is IPF.

Definitions

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, peptide chemistry, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the term "pharmaceutical composition" or "composition" refers to a mixture of at least one compound useful within the disclosure with a pharmaceutically acceptable carrier. The pharmaceutical composition facilitates administration of the compound to a patient. Multiple techniques of administering a compound exist in the art including, but not limited to, subcutaneous, intravenous, oral, aerosol, inhalational, rectal, vaginal, transdermal, intranasal, buccal, sublingual, parenteral, intrathecal, intragastrical, ophthalmic, pulmonary, and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, a "pharmaceutically effective amount," "therapeutically effective amount," or "effective amount" of a compound is that amount of compound that is sufficient to provide a beneficial effect to the subject to which the compound is administered.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "treatment" or "treating" is defined as the application or administration of a therapeutic agent, i.e., a compound useful within the disclosure (alone or in combination with another pharmaceutical agent), to a patient, or application or administration of a therapeutic agent to an isolated tissue or cell line from a patient (e.g., for diagnosis or ex vivo applications), who has a disease or disorder and/or a symptom of a disease or disorder, with the purpose to cure, heal, alleviate, relieve, alter, remedy, ameliorate, improve or affect the disease or disorder and/or the symptoms of the disease or disorder. Such treatments may be specifically tailored or modified, based on knowledge obtained from the field of pharmacogenomics.

As used herein, the term "pH low insertion peptide" or "pHLIP" refers to a peptide that is water soluble and is unable to insert into a lipid bilayer, such as the plasma membrane of a eukaryotic cell, when the pH is neutral or basic. When the pH become acidic (such as below 7, below 6.8, below 6.5, below 6.2, below 6.0, below 5.8 or below 5.5), however; the peptide undergoes changes in conformation and gains the ability to insert into lipid bilayers. In some embodiments, the acidic pH cause at least a portion of the pHLIP to form a transmembrane α-helix. In some embodiments, the acidic pH caused conformational change causes the peptide to insert into the plasma membrane, which mediates lipid membrane translocation via a non-endocytic route. pH low insertion peptides are described in, for example, Hunt et al. (*Biochemistry*. 1997 Dec. 9; 36(49): 15177-92), Reshetnyak et al. (*Proc Natl Acad Sci USA*. 2008 Oct. 7; 105(40):15340-5), Andreev et al. (*Molecular Membrane Biology*, 27:7, 341-352, 2010), Weerakkody et al. (*Proc Natl Acad Sci USA* 110, 5834-5839 (2013)), PCT Application Publications Nos. WO2012047354 and WO2017165452, U.S. Pat. Nos. 8,076,451, 8,846,081, 9,676,823, and 9,814,781, and U.S. Patent Applications No. US2008/0233107, US2012/0039990, US2015/0051153, US2015/0191508, US2016/0256560, US2018/0221500, and US2019/0382448. The entireties of these references are hereby incorporated herein by reference.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

In one aspect, the present disclosure relates to a miR-33 inhibitor. In certain embodiments, the miR-33 inhibitor is an miR-33a inhibitor. In other embodiments, the miR-33 inhibitor is an miR-33b inhibitor. In yet other embodiments, the miR-33 inhibitor is an miR-33a and an miR-33b inhibitor.

In certain embodiments, the miR-33 inhibitor is an antisense peptide nucleic acid (PNA) comprising a peptide backbone modified with at least nine nucleobases that are complementary to at least nine contiguous nucleotides in miR-33. In some embodiments, the PNA comprises a peptide backbone modified with seventeen nucleobases that are complementary to seventeen contiguous nucleotides in miR-33. In certain embodiments, the PNA comprises a charge-neutral backbone. Although not wishing to be limited by theory, it is believed that the charge-neutral backbone enables the PNA to hybridize to DNA and to bind single-strand targets with high specificity and affinity. In certain embodiments, the peptide backbone comprises a polyamide. In some embodiments, the peptide backbone is modified with at least ten nucleobases wherein each nucleobase is covalently bonded to the peptide backbone through an optional linker. In certain embodiments, the each nucleobase is covalently bonded to the peptide backbone through an acyl linker. In some embodiments, the acyl linker is a carboxymethylene linker. In certain embodiments, the nucleobases are selected from adenine, guanine, cysteine, thymine, and uracil. In certain embodiments, the PNA comprises 17 nucleobases comprising the sequence 5'-ATGCAACTACAATGCAA-3' (SEQ ID NO: 1). In some embodiments, the PNA comprises the sequence 5'-ATGCAACTACAATGCAA-Cys-SH-3' (SEQ ID NO: 2). In some embodiments, the thymine residues in SEQ ID NO: 1 or SEQ ID NO: 2 are replaced with uracil residues.

In some embodiments, the PNA is linked to a pH low insertion peptide (pHLIP). In certain embodiments, the PNA is covalently bonded to the pHLIP. In certain embodiments, the PNA is covalently bonded through the peptide backbone to the pHLIP. In other embodiments, the PNA is covalently bonded through a cysteine nucleobase on the PNA with a cysteine residue in the pHLIP. In certain embodiments, the cysteine nucleobase on the PNA and the cysteine residue in the pHLIP form a disulfide bond. In certain embodiments, the 3'-terminal cysteine residue of SEQ ID NO: 2 forms a disulfide bond with a cysteine residue in the pHLIP. In some embodiments, the pHLIP is modified with a fluorophore. In certain embodiments, the pHLIP is modified with a TAMRA fluorophore. In certain embodiments, the PNA is not susceptible to proteases and/or nucleases, making the PNA an ideal molecule for targeting microRNAs.

In certain embodiments, the miR-33 inhibitor comprises a structure of formula (I)

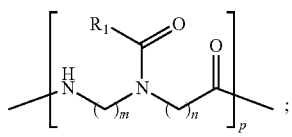

formula (I)

wherein:
each $R_1$ is independently $(CH_2)_q$-nucleobase;
m, n, and q are each independently an integer from 1 to 3;
p is an integer from 5 to 50; and
wherein the nucleobase is selected from adenine, guanine, cysteine, thymine, and uracil such that adjacent nucleobases are complementary to contiguous nucleotides in miR-33.

In certain embodiments, m is 2. In certain embodiments, n is 1. In certain embodiments, each q is 1. In certain embodiments, p is an integer from 9 to 17. In some embodiments, p is 17.

In certain embodiments, the nucleobases of formula (I) comprise SEQ ID NO: 1. In certain embodiments, the nucleobases of formula (I) comprise SEQ ID NO: 2. In some embodiments, the thymine residues in SEQ ID NO: 1 or SEQ ID NO: 2 are replaced with uracil residues.

In certain embodiments, the structure of formula (I) is linked to a pHLIP. In some embodiments, the structure of formula (I) is covalently bonded to a pHLIP. In some embodiments, the structure of formula (I) is covalently bonded through a cysteine nucleobase with a cysteine residue in the pHLIP. In certain embodiments, the cysteine nucleobase on the structure of formula (I) and the cysteine residue in the pHLIP form a disulfide bond. In certain embodiments, the 3'-terminal cysteine residue of SEQ ID NO: 2 forms a disulfide bond with a cysteine residue in the pHLIP. In some embodiments, the pHLIP is modified with a fluorophore. In certain embodiments, the pHLIP is modified with a TAMRA fluorophore.

In some embodiments, the miR-33 inhibitor is a component of a composition. In certain embodiments, the composition comprises a pharmaceutically acceptable carrier. Exemplary pharmaceutically acceptable carriers are described elsewhere herein. In some embodiments, the composition comprises a solvent. In certain embodiments, the solvent is an aqueous solvent. In certain embodiments, the aqueous solvent is water. In other embodiments, the aqueous solvent is saline. In some embodiments, the composition comprises one or more liquid pharmaceutically acceptable carriers such that the composition may be administered to a subject via intravenous, intranasal, and/or inhalational administration. In certain embodiments, the composition comprises one or more pharmaceutically acceptable carriers such that the composition may be administered to a subject as an aerosol. In some embodiments, a composition comprising an miR-33 inhibitor disclosed herein and an aqueous solvent does not comprise any additional pharmaceutically acceptable carriers. In certain embodiments, a composition comprising an miR-33 inhibitor disclosed herein and an aqueous solvent can be administered to a subject intranasally without any additional pharmaceutically acceptable carriers. In certain embodiments, composition comprising an miR-33 inhibitor disclosed herein and an aqueous solvent can be administered to a subject as an aerosol without any additional pharmaceutically acceptable carriers.

Salts

The compounds described herein may form salts with acids or bases, and such salts are included in the present disclosure. The term "salts" embraces addition salts of free acids or bases that are useful within the methods of the disclosure. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present disclosure, such as for example utility in process of synthesis, purification or formulation of compounds useful within the methods of the disclosure.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the disclosure.

Suitable pharmaceutically acceptable base addition salts of compounds of the disclosure include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Methods

In another aspect, the present disclosure relates to a method of treating, ameliorating, and/or preventing pulmonary fibrosis in a subject, the method comprising administering to the subject a therapeutically effective amount of an miR-33 inhibitor.

The miR-33 inhibitor is described elsewhere herein. In certain embodiments the miR-33 inhibitor comprises a structure of formula (I). In some embodiments, the miR-33 inhibitor comprises a structure of formula (I) that is linked to a pHLIP. In certain embodiments, the structure of formula (I) is covalently bonded to the pHLIP. In some embodiments, the miR-33 inhibitor is a component of a composition. Other components of the composition are described elsewhere herein.

The miR-33 inhibitor can be administered to the subject in any amount necessary to treat pulmonary fibrosis in the subject. In some embodiments, the miR-33 inhibitor treats, ameliorates, and/or prevents pulmonary fibrosis in the subject by reducing, decreasing, or alleviating one or more symptoms of pulmonary fibrosis in the subject. In other embodiments, the miR-33 inhibitor leads to the resolution of pulmonary fibrosis in the subject. A dose of miR-33 inhibitor of between about 0.5 mg/kg to about 5 mg/kg was demonstrated to have a therapeutic effect on pulmonary fibrosis in mice. Therefore, in some embodiments, a similar dosage range of the miR-33 inhibitor, appropriately adjusted for administration to subject being treated, is administered to treat pulmonary fibrosis in the subject. A dose of miR-33 inhibitor of between about 0.05 µg/µl and about 0.5 µg/µl was found to have an antifibrotic effect on an ex vivo human precision cut lung slice (PCLS). Therefore, in some embodiments, a similar dosage range of the miR-33 inhibitor is administered to treat pulmonary fibrosis in the subject. In yet other embodiments, a dosage range of between about 0.05 µg/µl and about 0.5 mg/kg (adjusted for the subject as described above) of the miR-33 inhibitor is administered to the subject to treat pulmonary fibrosis.

The miR-33 inhibitor can be administered to the subject using any mode of administration known to a person of skill in the art. In certain embodiments, the miR-33 inhibitor is administered to the subject inhibitor via a mode of administration selected from nasal, pulmonary, aerosol, inhalational, intratracheal, intrabronchial, intraperitoneal, intravenous, oral gavages, and combinations thereof. In certain embodiments, the miR-33 inhibitor is administered to the subject via intranasal administration. In certain embodiments, the miR-33 inhibitor, dissolved in saline, is delivered directly through the nose of the subject to the subject's lungs. Although not wishing to be limited by theory, pulmonary delivery of the miR-33 inhibitor is expected to be an easy and convenient mode of administration with fewer systemic side effects, faster onset of action, improved therapeutic response, and reduced cost. In some embodiments, the pulmonary delivery of the miR-33 inhibitor delivers the inhibitor directly to the lung by an intranasal or aerosolized route.

The pulmonary fibrosis can be any type of pulmonary fibrosis known to a person of skill in the art. In certain embodiments, the pulmonary fibrosis is idiopathic pulmonary fibrosis (IPF).

In certain embodiments, the subject is a mammal. In certain embodiments, the subject is a human.

Although not wishing to be limited by theory, it is believed that miR-33 contributes to the development of pulmonary fibrosis by its effects on mitochondrial biogenesis and its function in macrophages. Therefore, a cell specific inhibitor of miR-33 acts to provide resolution of pulmonary fibrosis, thus treating pulmonary fibrosis in a subject. In some embodiments, a macrophage specific inhibitor of miR-33 acts to provide resolution of pulmonary fibrosis. In certain embodiments, the miR-33 inhibitors disclosed elsewhere herein are macrophage specific miR-33 inhibitors. In some embodiments, PGC-1α, a marker of mitochondria biogenesis, is decreased in the lungs of subjects with IPF. In some embodiments, the miR-33 inhibitors disclosed herein promote mitochondrial biogenesis and/or the efficient production of ATP via a PGC-1α dependent pathway. In some embodiments, the miR-33 inhibitors disclosed herein reduce cell death in AEC-II cells, thus treating pulmonary fibrosis in the subject.

Pharmaceutical Compositions and Formulations

The disclosure provides pharmaceutical compositions comprising at least one compound of the disclosure or a salt or solvate thereof, which are useful to practice methods of the disclosure. Such a pharmaceutical composition may consist of at least one compound of the disclosure or a salt or solvate thereof, in a form suitable for administration to a subject, or the pharmaceutical composition may comprise at least one compound of the disclosure or a salt or solvate thereof, and one or more pharmaceutically acceptable carriers, one or more additional ingredients, or any combinations of these. At least one compound of the disclosure may be present in the pharmaceutical composition in the form of a physiologically acceptable salt, such as in combination with a physiologically acceptable cation or anion, as is well known in the art.

In certain embodiments, the pharmaceutical compositions useful for practicing the method of the disclosure may be administered to deliver a dose of between 1 ng/kg/day and 100 mg/kg/day. In other embodiments, the pharmaceutical compositions useful for practicing the disclosure may be administered to deliver a dose of between 1 ng/kg/day and 1,000 mg/kg/day.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the disclosure may be suitably developed for nasal, inhalational, oral, rectal, vaginal, pleural, peritoneal, parenteral, topical, transdermal, pulmonary, intranasal, buccal, ophthalmic, epidural, intrathecal, intravenous, or another route of administration. A composition useful within the methods of the disclosure may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the disclosure are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as cattle, pigs, horses, sheep, cats, and dogs.

In certain embodiments, the compositions of the disclosure are formulated using one or more pharmaceutically acceptable excipients or carriers. In certain embodiments, the pharmaceutical compositions of the disclosure comprise a therapeutically effective amount of at least one compound of the disclosure and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring, and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure include but are not limited to those selected from the group consisting of benzyl alcohol, sorbic acid, parabens, imidurea and any combinations thereof. One such preservative is a combination of about 0.5% to 2.0% benzyl alcohol and 0.05-0.5% sorbic acid.

The composition may include an antioxidant and a chelating agent that inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non-ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the disclosure may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the disclosure may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the disclosure are administered to the patient in dosages that range from one to six times per day or more. In other embodiments, the compositions of the disclosure are administered to the patient in range of dosages that include, but are not limited to, once every day, every two days, every three days to once a week, and once every two weeks. It will be readily apparent to one skilled in the art that the frequency of administration of the various combination compositions of the disclosure will vary from subject to subject depending on many factors including, but not limited to, age, disease or disorder to be treated, gender, overall health, and other factors. Thus, the disclosure should not be construed to be limited to any particular dosage regime and the precise dosage and composition to be administered to any patient will be determined by the attending physician taking all other factors about the patient into account.

Compounds of the disclosure for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the disclosure is from about 0.5 µg and about 5,000 mg. In some embodiments, a dose of a compound of the disclosure used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the disclosure include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Formulations may be employed in admixtures with conventional excipients, i.e., pharmaceutically acceptable organic or inorganic carrier substances suitable for oral, parenteral, nasal, intravenous, subcutaneous, enteral, aerosol, ophthalmic, inhalational, intratracheal, intrapulmonary, intrabronchial, and topical or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Pulmonary Administration

Routes of administration of any of the compositions of the invention include nasal, inhalational, intratracheal, intrapulmonary, intrabronchial, and inhalation.

Suitable compositions and dosage forms include, for example, dispersions, suspensions, solutions, syrups, granules, beads, powders, pellets, liquid sprays for nasal administration, dry powder or aerosolized formulations for inhalation, and the like. It should be understood that the formulations and compositions that would be useful in the present invention are not limited to the particular formulations and compositions that are described herein.

Powdered and granular formulations of a pharmaceutical preparation of the invention may be prepared using known methods. Such formulations may be administered directly to a subject, used, for example, to form a material that is suitable to administration to a subject. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration in certain embodiments have an average diameter in the range from about 0.1 to about 200 nanometers.

The pharmaceutical composition of the invention may be delivered using an inhalator such as those recited in U.S. Pat. No. 8,333,192 B2, which is incorporated herein by reference in its entirety.

In certain embodiments, the composition of the invention comprises a stable dry powder blend containing an active agent; lactose particles, comprising lactose $H_2O$, gelatin and starch maize; sodium starch glycolate; magnesium stearate; and talc silicified, comprising talc purified and colloidal silicon dioxide. In other embodiments, the dry powder comprises the active agent in an amount 4 to 0.02 mg per 100 mg of the dry powder. In yet other embodiments, the dry powder comprises lactose in an amount higher than 90 mg per 100 mg of the dry powder preparation. In yet other embodiments, the dry powder comprises lactose particles consisting of lactose $H_2O$, gelatin and starch maize, wherein the ratio by weight-mg of: "lactose $H_2O$":"gelatin":"starch maize" is 55-75:0.20-0.80:20-40. In yet other embodiments, the dry powder comprises sodium starch glycolate in an amount of 4-8 mg per 100 mg of dry powder. In yet other embodiments, the dry powder comprises magnesium stearate in an amount of 0.5-2 mg per 100 mg of dry powder. In yet other embodiments, the dry powder comprises talc silicified, in an amount of 2 mg per 100 mg of dry powder, wherein the talc silicified comprises talc purified and colloidal silicon dioxide in an amount of 0.667 mg of talc purified and 1.333 mg of colloidal silicon dioxide for 2 mg of talc silicified. In yet other embodiments, the blend further comprises a lake. In yet other embodiments, the dry powder comprises sodium starch glycolate in an amount of 5-6 mg per 100 mg of dry powder. In yet other embodiments, the dry powder comprises magnesium stearate in an amount of 1 mg per 100 mg of dry powder.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Additional Administration Forms

Additional dosage forms of this disclosure include dosage forms as described in U.S. Pat. Nos. 6,340,475, 6,488,962, 6,451,808, 5,972,389, 5,582,837, and 5,007,790. Additional dosage forms of this disclosure also include dosage forms as described in U.S. Patent Applications Nos. 20030147952, 20030104062, 20030104053, 20030044466, 20030039688, and 20020051820. Additional dosage forms of this disclosure also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the compositions and/or formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the disclosure may be administered in the form of microparticles, for example, by injection or in the form of wafers or discs by implantation.

In certain embodiments of the disclosure, the compounds useful within the disclosure are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

Dosing

The therapeutically effective amount or dose of a compound described herein depends on the age, sex and weight of the patient, the current medical condition of the patient and the progression of the disease or disorder in the patient being treated. The skilled artisan is able to determine appropriate dosages depending on these and other factors.

A suitable dose of a compound described herein can be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound(s) described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds described herein can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents are considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

It is to be understood that, wherever values and ranges are provided herein, the description in range format is merely for convenience and brevity and should not be construed as an inflexible limitation on the scope of the disclosure. Accordingly, all values and ranges encompassed by these values and ranges are meant to be encompassed within the scope of the present disclosure. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present disclosure. However, they are in no way a limitation of the teachings or disclosure of the present disclosure as set forth herein.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Macrophage Specific Regulatory Role of miR-33 in Pulmonary Fibrosis

Methods

Both miR-33 knockout and macrophage-specific knockout mice (LysM$^{CRE}$xmiR-33$^{fl/fl}$) as well as control littermates were treated with 0.9% saline or bleomycin (1.5 U/kg—day 0) and the lungs were isolated at day 14-21 at the peak of the fibrosis phase. In parallel, primary alveolar macrophages were isolated from these mice to identify cell specificity of miR-33 in mitochondrial function.

To evaluate mitochondrial function, a variety of approaches such as basal oxygen consumption rate (OCR), ATP-linked respiration and proton leak measurements (using the Seahorse XF96 Extracellular Flux Analyzer), ATP production assay, and/or flow cytometric analysis (to measure mitochondrial ROS by mitoSOX) can be used.

Transmission Electron microscopy was performed on lung tissues and alveolar macrophages to identify mitochondrial structure and the digital images were qualified by Image J software.

Primary macrophages were isolated from cryopreserved cells obtained from human lungs and the BAL of patients with IPF and healthy controls. In vitro experiments were performed on these macrophages using Magnetic-Activated Cell Sorting (MACS) for mitochondrial evaluations after miR-33 inhibition using peptide nucleic acids (PNAs) anti miR-33 and scramble control. The nucleobases of the scramble control PNA have the sequence 5'-TACGCTAAT-CACAAAGA-Cys-SH-3' (SEQ ID NO: 3).

To determine the effects of miR-33 inhibition on its target gene, PGC-1α expression and activation was evaluated at steady state and after bleomycin injury in alveolar macrophages isolated from mice lungs. PGC-1α siRNA will be used intranasally after bleomycin exposure in miR-33 null mice and the fibrosis phenotype in these mice will be characterized by histology and collagen measurement.

Peptide nucleic acids (PNAs) attached to pHLIP as a potential therapeutic anti-fibrotic agent in pulmonary fibrosis were delivered (intranasal or inhalation) in different doses to identify the most efficacious cell specific inhibitory system. Macrophages were isolated after the delivery and the efficacy of inhibition was tested in a time and dose dependent manner. Then, the minimal efficacious dose was used following bleomycin administration (intratracheally, 1.5 U/kg) and the extent of fibrosis was compared to animals treated with scrambled microRNA.

For inhalational delivery of the PNAs, the animals will be exposed to aerosol using the SCIREQ inExpose system, which is suitable for six mice at a time. The system contains soft restraints for mice. Which conform to the mouse's body shape, preventing overheating, humidity, and thoracic restriction, which translates into less stress during exposure. All inhibitors and scramble controls will be administered daily at days 3-13, or at 10-20 days, post-bleomycin and mice will be sacrificed at days 14 or 21, respectively. Mice lungs will be harvested for functional and molecular analyses. To identify the dose dependency of the miR-33 inhibitor and to establish the minimal efficacious dose of this agent, different doses of the miR-33 inhibitor will be administered in the bleomycin model and the extent of fibrosis will be evaluated.

Another animal model of lung fibrosis will be used to show that the therapeutic effect of the disclosed miR-33 inhibitors is not limited to the bleomycin model. For this purpose, the effect of the miR-33 inhibitor will be tested in a TGF-β induced lung fibrosis animal model by delivering the miR-33 inhibitor following a single dose of intranasal adenoviral TGF-β. Lungs and bronchoalveolar lavage will be collected after establishment of fibrosis. The extent of fibrosis in the lung will be evaluated by several techniques such as the measurement of hydroxyproline and total soluble collagen, immunohistochemistry using Masson trichrome assay and a-SMA staining, and gene expression of fibrotic markers. In both models, primary macrophages will be isolated from lung and BAL for metabolic evaluations.

Statistical Considerations

For the objective of determining the differences in response to therapy in animal models, if there are 10 subjects in both the control and treated groups and it is assumed that both groups have the same standard deviation (denoted by SD) across the samples within each group, there is an 82% power to detect a difference of 1.2×SD between the two groups at the 0.05 statistical significance level. For example, if the standard deviation of the response in the treatment group is 2, the difference with 82% power at 0.05 statistical significance can be detected when the mean response in the control group is >2.4 different than the treatment group. Thus, in all experimental conditions, the minimal number of animals used/to be used is 10. Animal data will be analyzed using the Stata 13 software package or, where needed, the R environment version 2.13.1 for statistical analysis.

Results and Selected Discussion

MicroRNA-33 (miR-33) is a family (miR-33a and miR-33b) of intronic microRNAs which control cellular energy status and mitochondrial function. In certain embodiments, miR-33 contributes to the development of pulmonary fibrosis by its effects on mitochondrial biogenesis and function in macrophages, and thus a cell specific inhibition of miR-33 may lead to the resolution of pulmonary fibrosis. One of the main problems in lung related disorders is the lack of targeted miRNA delivery technology to minimize off-target effects and improve the safety of microRNAs in vivo. Also, current anti-miR technologies are hindered by physiological and cellular barriers to delivery into targeted cells.

miR-33 has a crucial role in cholesterol metabolism but has never been studied in the concept of lung fibrosis. miR-33 is an intronic microRNA located within the genes encoding sterol-regulatory element-binding factors 1 and 2 and is known as master regulators of sterol and fatty acid metabolism with effects on mitochondrial function. miR-33 has been implicated in cardiac and kidney fibrosis. A macrophage-specific regulatory role for miR-33 in pulmonary fibrosis was discovered herein and this novel observation led to the exploration of miR-33 as a novel target to treat pulmonary fibrosis through controlling mitochondrial homeostasis in macrophages. Prior to this disclosure, there were no effective pro-mitochondrial anti-microRNA therapies for pulmonary fibrosis. The present disclosure demonstrates that inhibiting miR-33 in macrophages is an efficient and practical approach and supports the study of the cell/target specific therapeutic effectiveness in IPF treatment. Furthermore, the disclosure provides a formulation to deliver a microRNA inhibitor at a cell specific level.

It was recently demonstrated that delivery of thyroid hormone or sobetirome, a small molecule thyroid hormone, against fibrosis was dependent on induction of PGC-1α. MicroRNA-33 (miR-33a and miR-33b) are intronic microRNAs which control cellular energy status and mitochondrial function. Inhibition of endogenous miR-33 in macrophages promotes mitochondrial biogenesis and efficient production of ATP via a PGC-1α dependent pathway. The present disclosure provides an understanding of the cellular mechanisms that contribute to the development of pulmonary fibrosis and proposes a novel cell specific therapeutic approach for this disease. The present disclosure improves treatment of pulmonary fibrosis by:

1) Emphasizing the importance of microRNAs in pulmonary fibrosis by focusing on the therapeutic role of miR-33: The identification of a novel, effective, long-term anti-fibrotic agent that targets the root causes of pulmonary fibrosis is very appealing. Individual microRNAs that modulate expression of multiple mRNA targets and interfere with single microRNAs can have broad effects on multiple cellular pathways.

2) Targeting the mitochondria as a key mechanistic modulator of pulmonary fibrosis: Increasing evidence suggests that mitochondrial dysfunction underlies multiple conditions including pulmonary fibrosis. Metabolic reprogramming and mitochondrial dysfunction in the pathogenesis of IPF could be the main key to resolve and control this fatal disease. This microRNA inhibitor as a pro-mitochondrial function therapy is a novel approach in treating IPF.

3) Novel therapeutic interventions: Utilizing miR-33 inhibitors as therapeutic agents to target macrophages in the lung is a novel therapeutic approach. Therefore, the present disclosure provides a groundbreaking therapy to target mitochondrial dysfunction.

Elucidating the Mechanism by Which miR-33 Regulates Fibrosis via Modulating Mitochondrial Function in Macrophages Following a systematic approach, it was discovered that in IPF BAL cells, which are mostly alveolar macrophages, miR-33 increases dramatically compared to controls. This upregulation of miR-33, which is a well-known regulator or metabolic pathways, led to the exploration of whether miR-33 could be a novel target to treat IPF through controlling mitochondrial homeostasis of the lung. The investigation was extended with the evaluation of miR-33 null mice having bleomycin-induced pulmonary fibrosis. The data shows that these mice are protected against lung fibrosis. Upon further investigation, it was discovered that miR-33 macrophage specific knockout mice show similar protection against bleomycin-induced pulmonary fibrosis. Mitochondrial dysfunction can be an important factor in susceptibility to IPF. While others have implemented the regulatory role of miR-33 in mitochondria (especially in macrophages) these studies all focus on fatty acid oxidation and cholesterol metabolism in other disorders, such as atherosclerosis and diabetes.

Figure 1A:
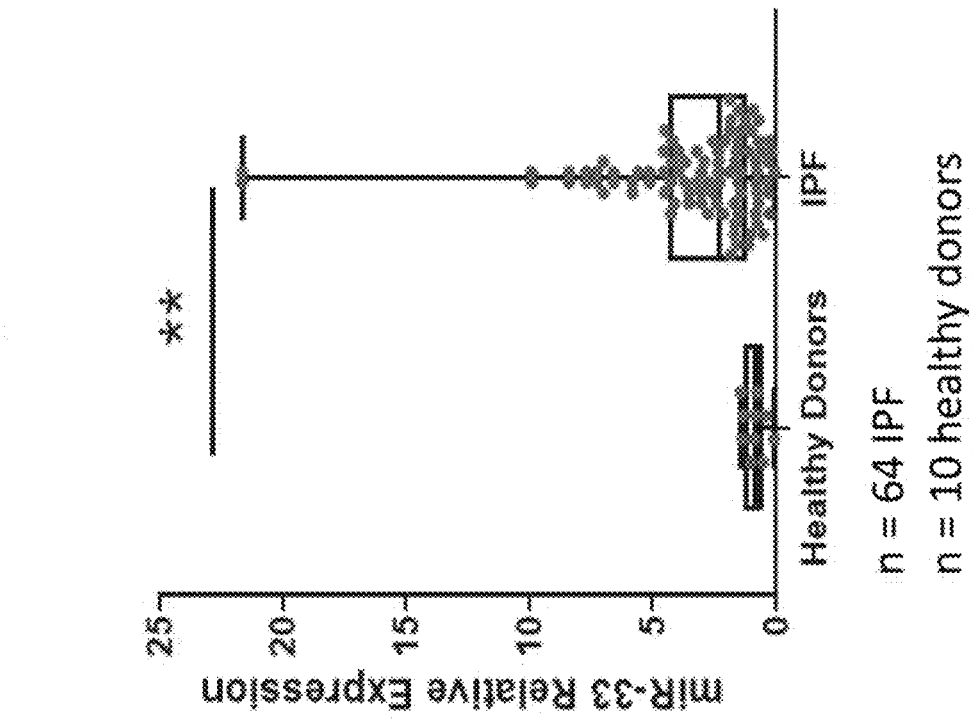
FIG. 1A depicts that microRNA-33 (miR-33) is increased in cells isolated from the bronchoalveolar lavage (BAL) of patients with IPF compared to controls (P=0.0024, RC=5), in accordance with some embodiments.
Figure 2:
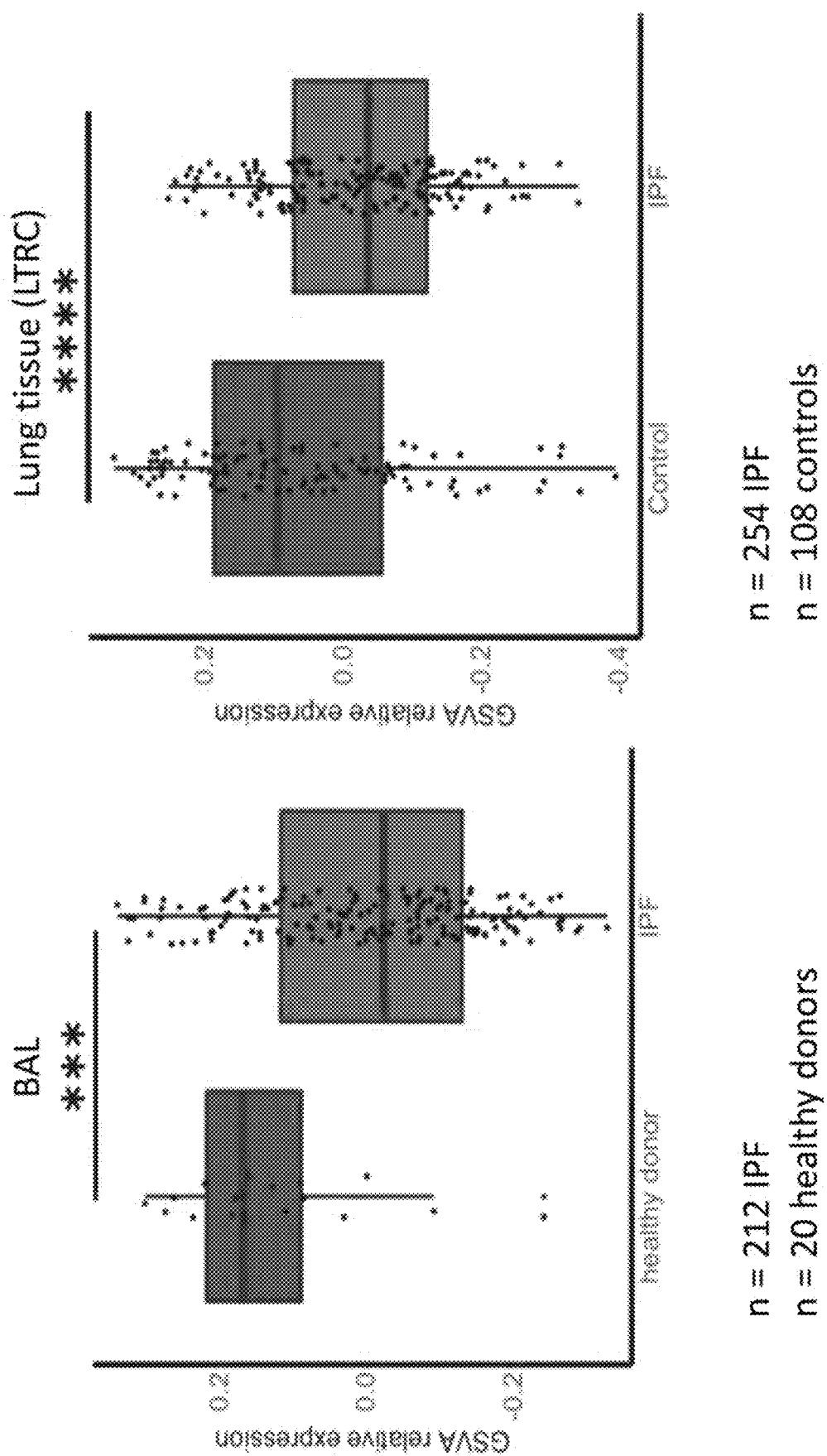
FIG. 2 depicts that miR-33 target gene expressions are decreased in BAL and lungs of IPF patients, in accordance with some embodiments.

The level of miR-33 was evaluated in Broncho Alveolar Lavage (BAL) samples obtained from 64 well-characterized patients with IPF and compared to 10 aged matched healthy controls. This analysis revealed that miR-33 is significantly upregulated in IPF versus controls (P value=0.0024) (FIG. 1, FIG. 2). Based on this finding which shows that the major upregulation in miRNA-33 in human IPF happens in BAL cells, which are mostly macrophages (>90%), additional experiments on miR-33 effects in pulmonary fibrosis were focused on macrophages.

Figure 3:
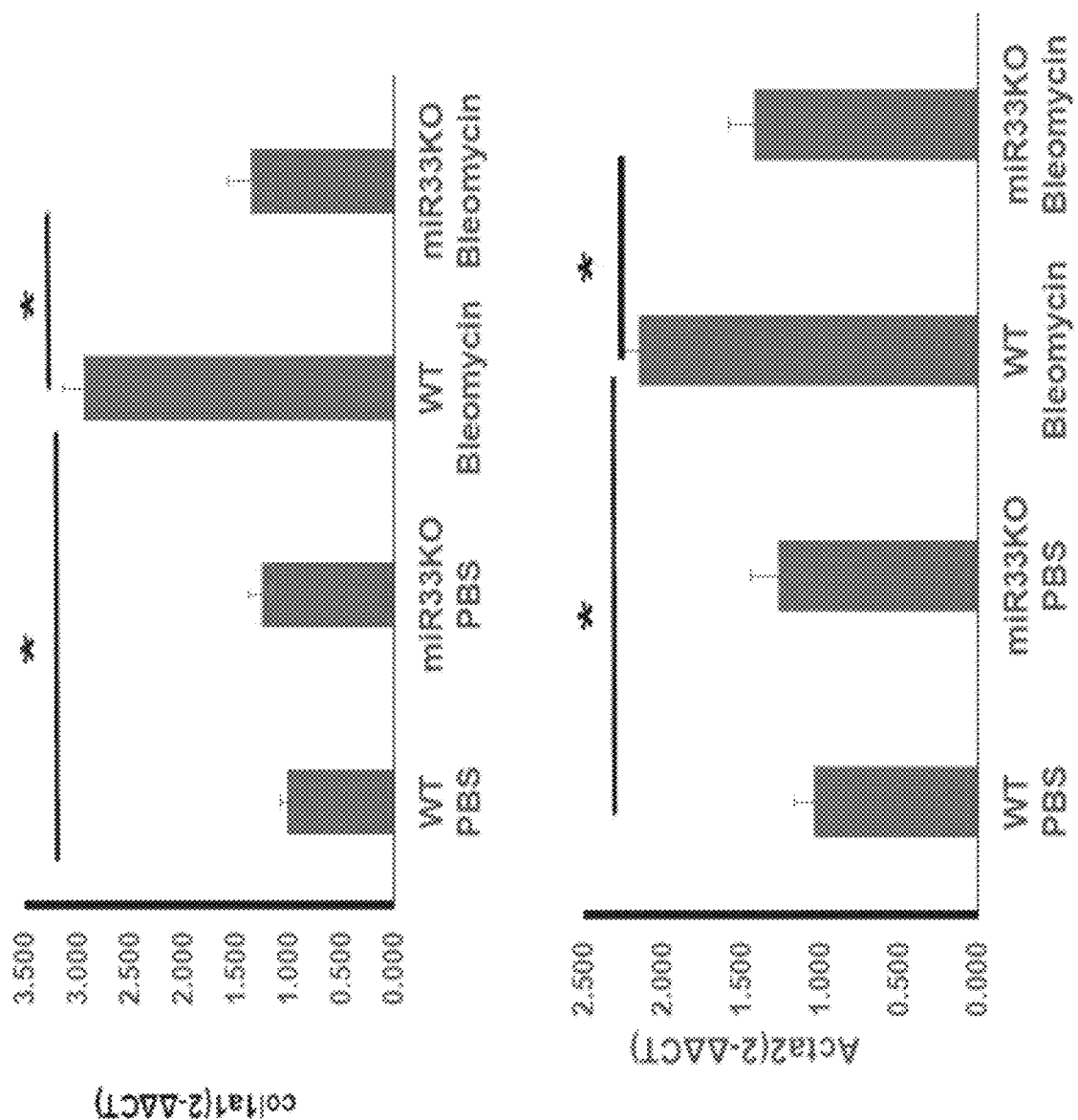
FIG. 3 shows that miR-33 KO is protective against bleomycin-induced pulmonary fibrosis, in accordance with some embodiments.
Figure 4:
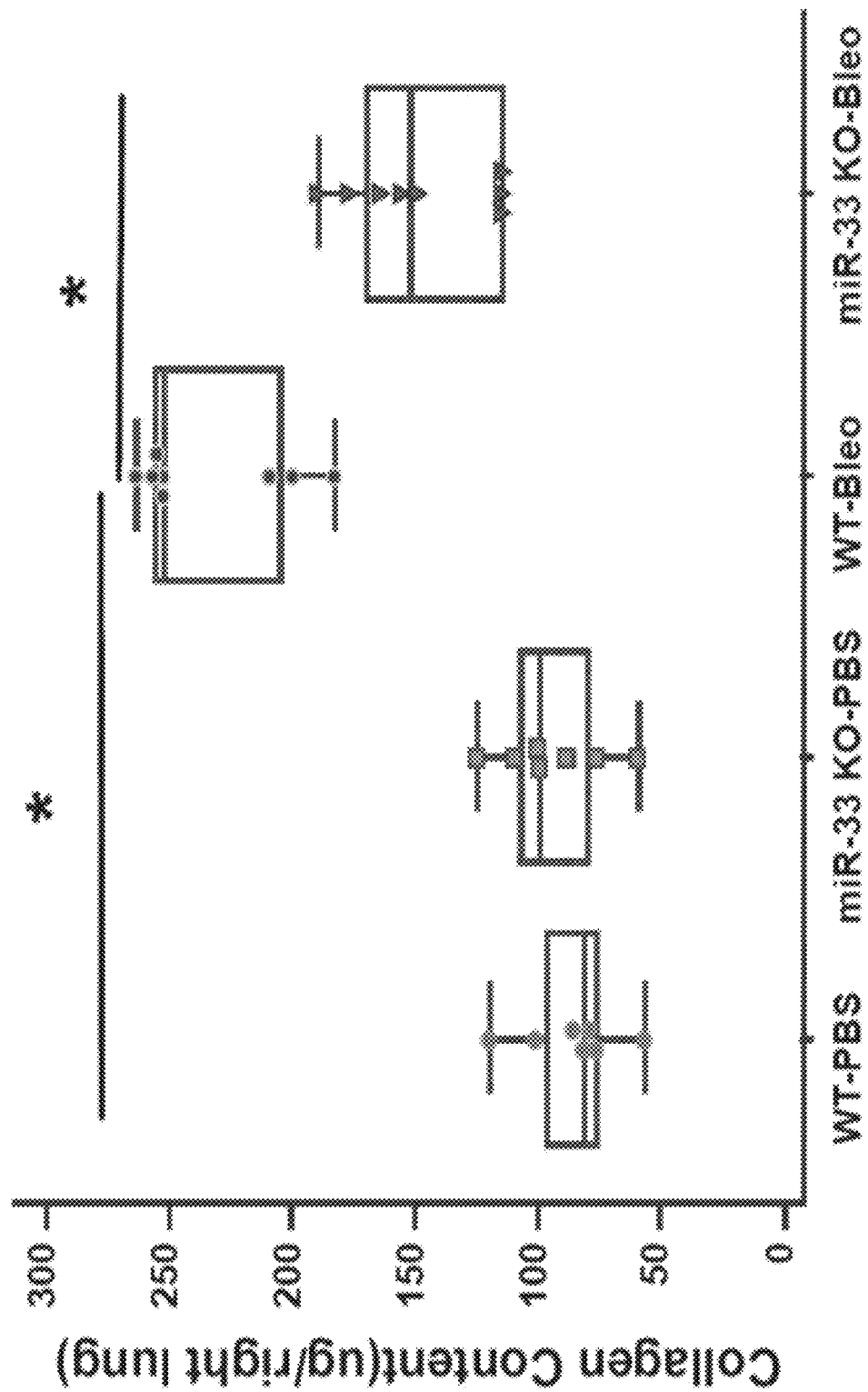
FIG. 4 depicts Sircol measurements of right lungs (all P values≤0.005) demonstrating that miR-33 KO is protective against bleomycin-induced pulmonary fibrosis, in accordance with some embodiments.
Figure 5:
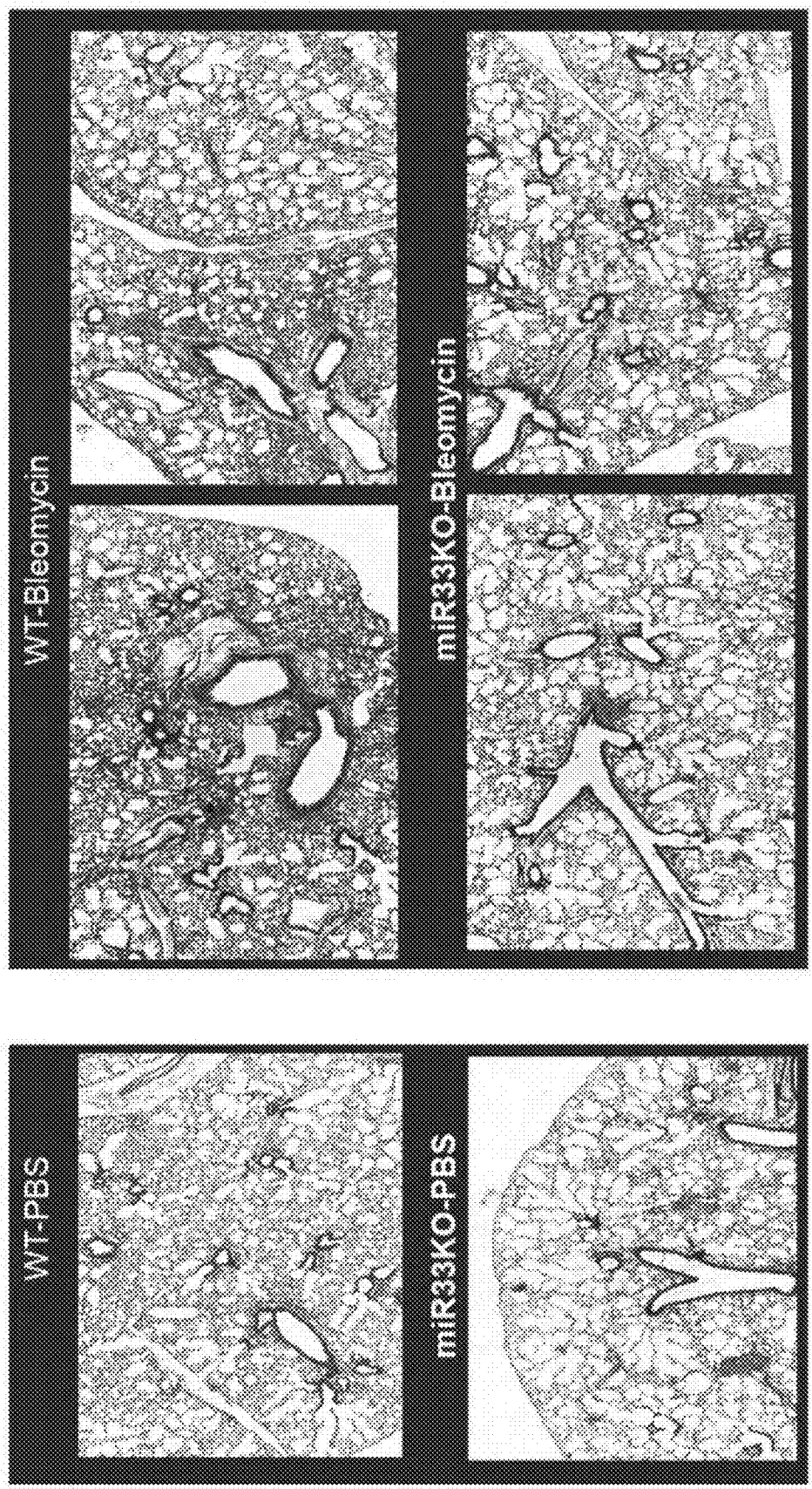
FIG. 5 depicts Masson-Trichrome staining of lung tissues demonstrating that miR-33 KO is protective against bleomycin-induced pulmonary fibrosis, in accordance with some embodiments.

To identify the role of miR-33 in lung fibrosis, the level of this microRNA was tested in WT mice lungs at 14 days after intra-tracheal bleomycin delivery and demonstrated more than a two-fold increase (P value=0.02) in miR-33 levels in fibrotic lung tissues (FIG. 2). The investigation was extended by utilizing miR-33 null mice in a bleomycin-induced pulmonary fibrosis model. Intra-tracheal bleomycin was delivered to these mice and their lungs and BAL samples were evaluated after 14 days. A significant decrease in soluble collagen was identified (measurement via Sircol assay) in miR-33 null mice after bleomycin. This finding was validated by Masson Tichrome staining, which is a standard staining method to identify collagen accumulation in fibrotic tissues (FIG. 3, FIG. 4, FIG. 5).

Figure 6A:
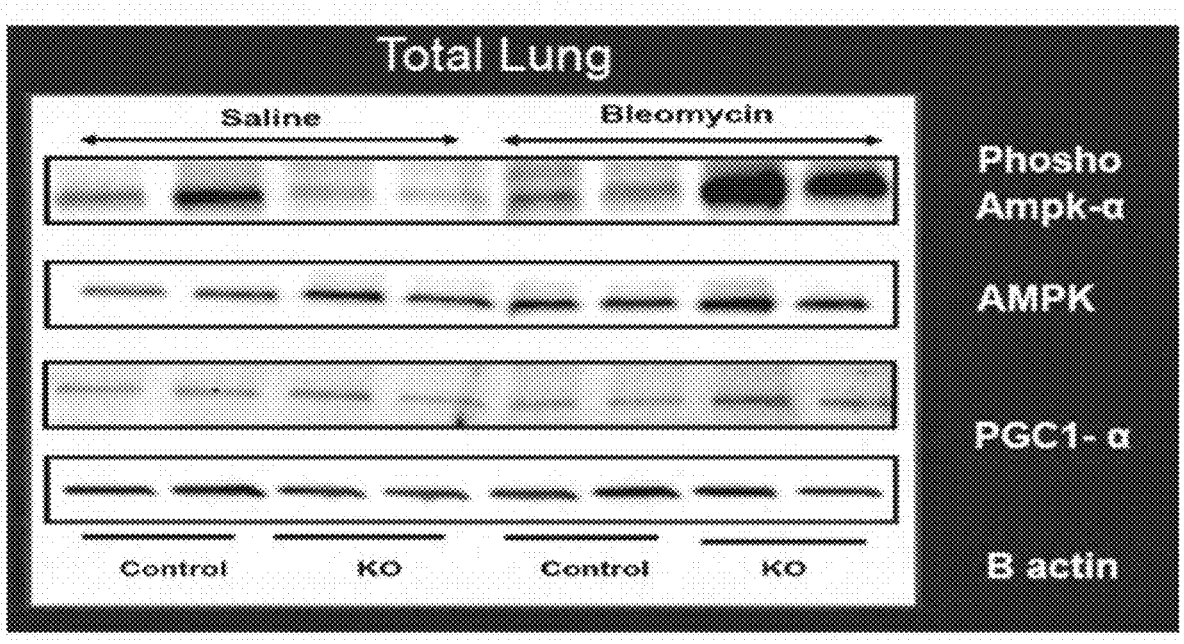
FIG. 6A is a Western blot of a total lung showing that PGC-1α is upregulated in miR-33 knockout mice after bleomycin, in accordance with some embodiments.
Figure 6B:
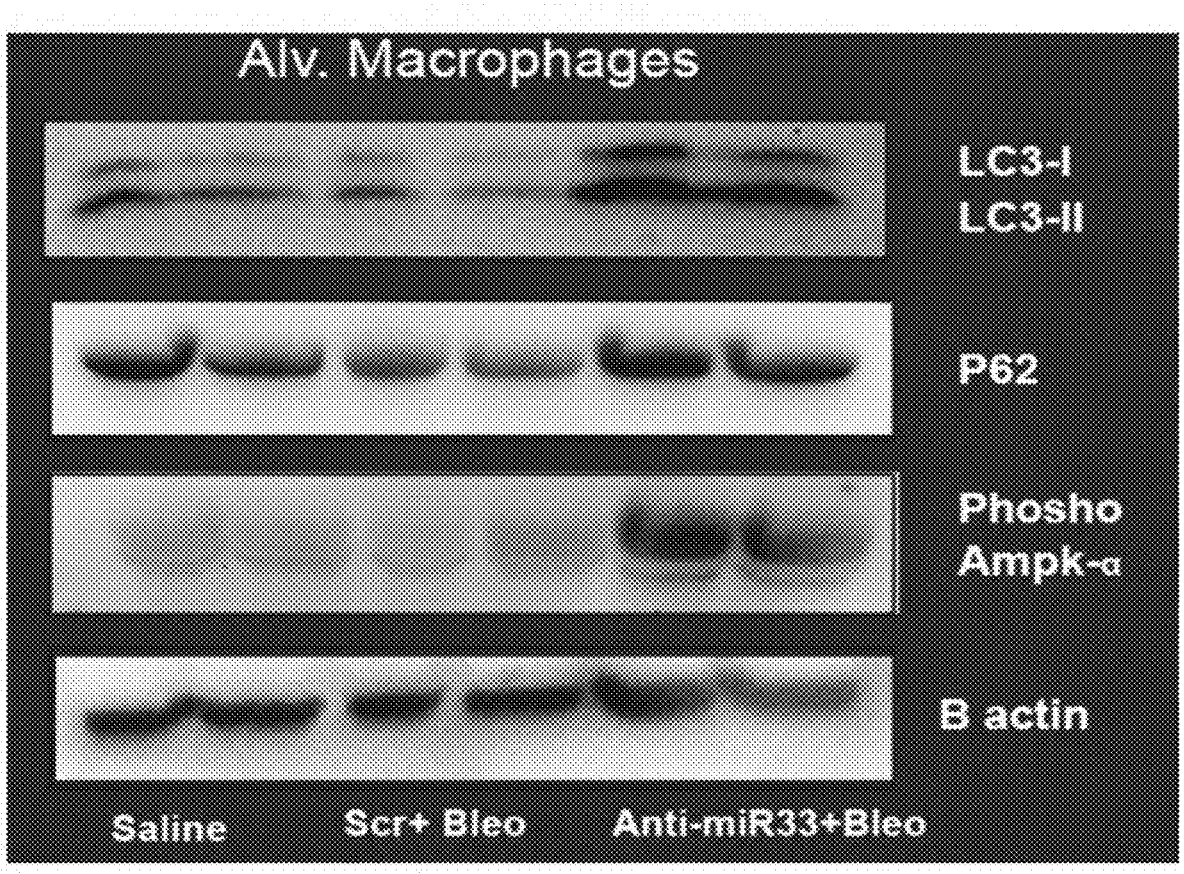
FIG. 6B shows that AMPK-α and LC3/P62 increase in the absence of miR-33, in accordance with some embodiments.

Peroxisome proliferator-activated receptor gamma (PPARγ) coactivator-1α (PPARGC1A or PGC-1α) is a well-known master regulator of mitochondria biogenesis. It was confirmed that PGC-1α is a direct and specific target of miR-33, with conserved binding sites in the 3'UTR of both human and mouse transcripts. The level of PGC-1α was evaluated in miR-33 knockout lungs before and after bleomycin exposure. Interestingly, in lung tissues after bleomycin injury, PGC-1α is increased significantly (FIG. 6).

Figure 7:
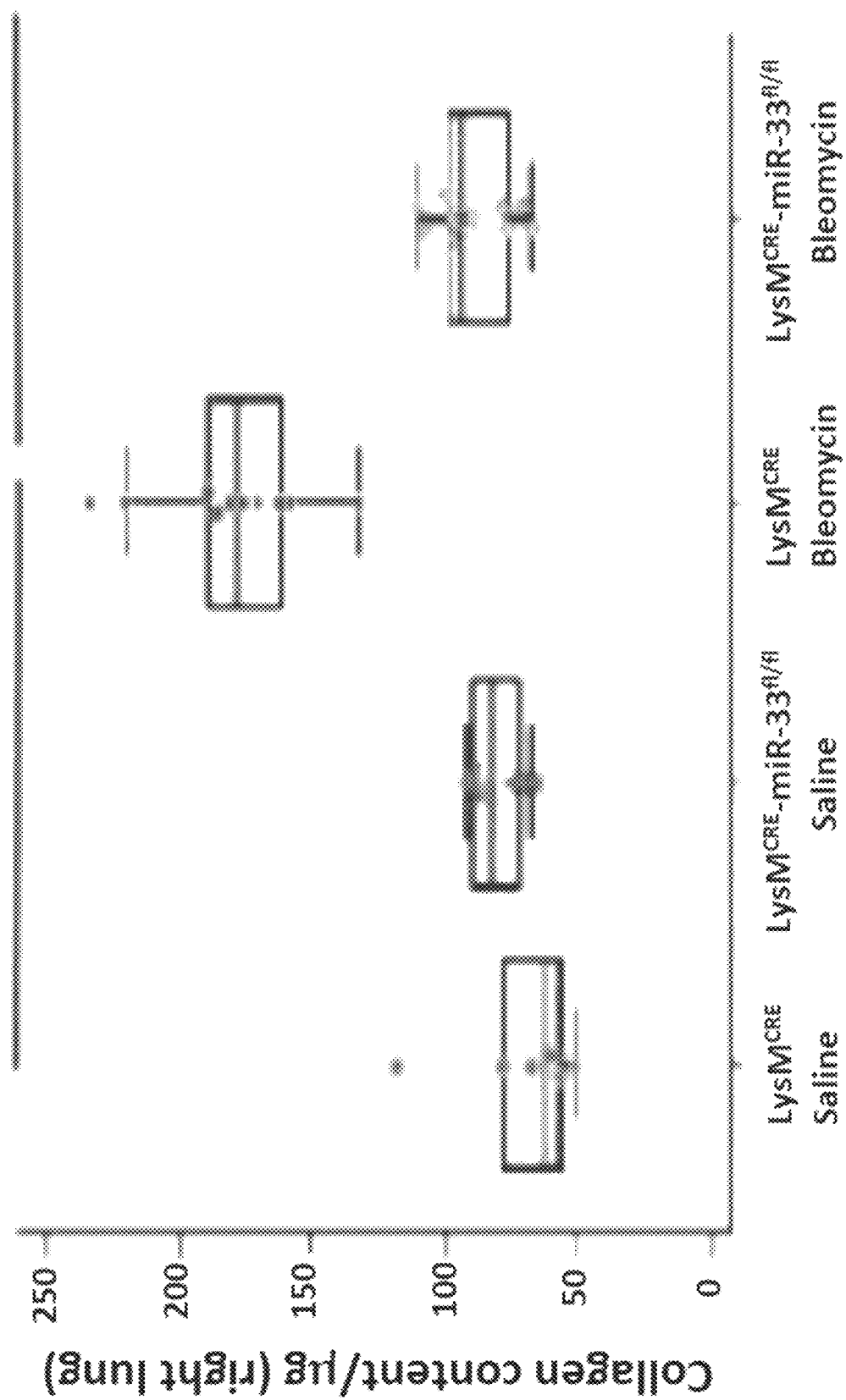
FIG. 7 is a graph of the results from Sircol measurements of right lungs (all P values ≤0.005) demonstrating that macrophage specific miR-33 KO (LysM$_{CRE}$xmiR-33$^{fl/fl}$) is protective against bleomycin-induced pulmonary fibrosis, in accordance with some embodiments.

The investigation was extended by utilizing miR-33 macrophage-specific knockout mice (LysM$^{CRE}$xmiR-33$^{fl/fl}$) and controls in a bleomycin-induced pulmonary fibrosis model. Intra-tracheal bleomycin was delivered to the mice and their lungs and BAL samples were evaluated after 14 days. Significant decrease in soluble collagen (measurement via Sircol assay) was identified and confirmed by Masson Trichrome staining (FIG. 7, FIG. 8).

Based on the data demonstrating the protective role of miR-33 ablation, the macrophage specific role of miR-33 in mitochondrial biogenesis and morphology in pulmonary fibrosis was explored as follows.

1) To determine whether the effects of miR-33 in mice lung fibrosis are mediated through its effects on mitochondria: Mitochondrial biogenesis and energetics were evaluated in alveolar macrophages isolated from miR-33 knockout mice and macrophage-specific knockout mice (LysM$^{CRE}$xmiR-33$^{fl/fl}$) in vitro, at baseline, and in response to bleomycin.

2) To elucidate whether miR-33 regulates mitochondrial function in human IPF: Cryopreserved cells from the lungs and BAL of patients with IPF and healthy controls were evaluated for their mitochondrial function and morphology after miR-33 inhibition.

3) To elucidate whether miR-33 regulates mitochondrial function through PGC-1α (a known target of miR-33) in vitro and in vivo: The effects of miR-33 inhibition on PGC-1α expression and activation were analyzed at steady state and after bleomycin injury in alveolar macrophages isolated from mice.

Figure 9:
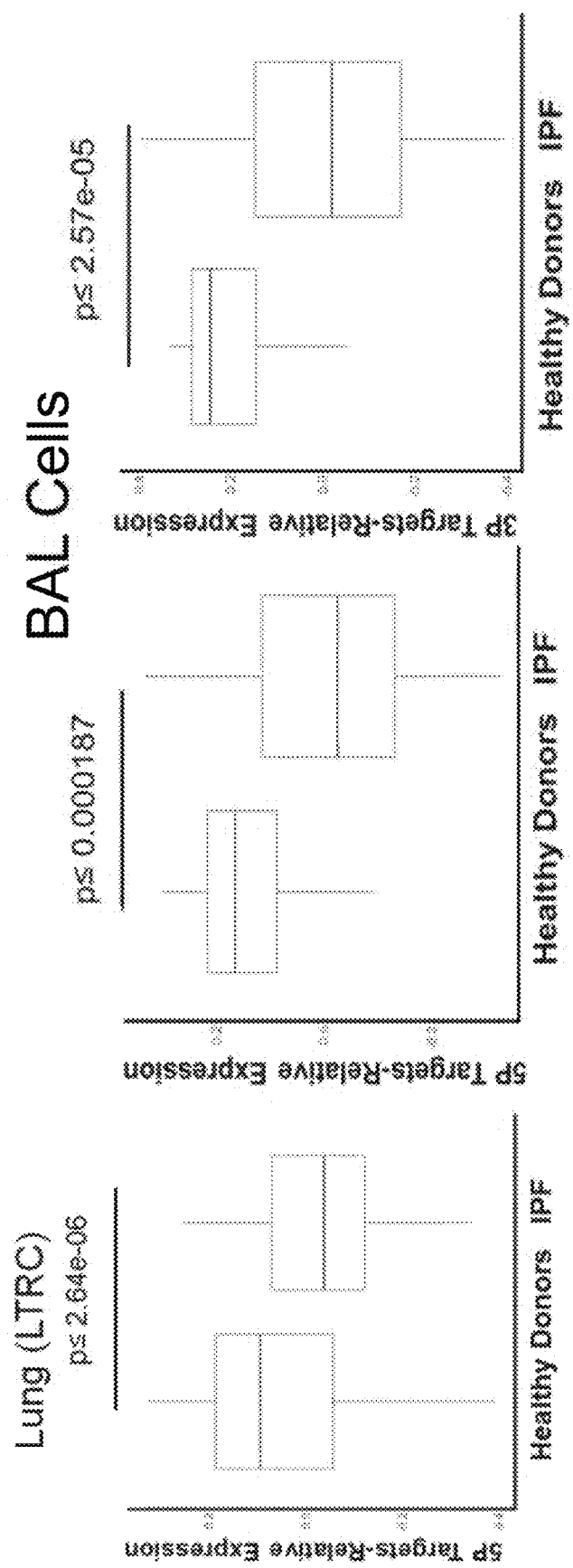
FIG. 9 shows that miR-33 target gene expression is increased in the BAL and lungs of IPF patients compared to controls, in accordance with some embodiments.

FIG. 9 shows that miR-33 target gene expression is increased in the BAL and lungs of IPF patients compared to controls.

Figure 10:
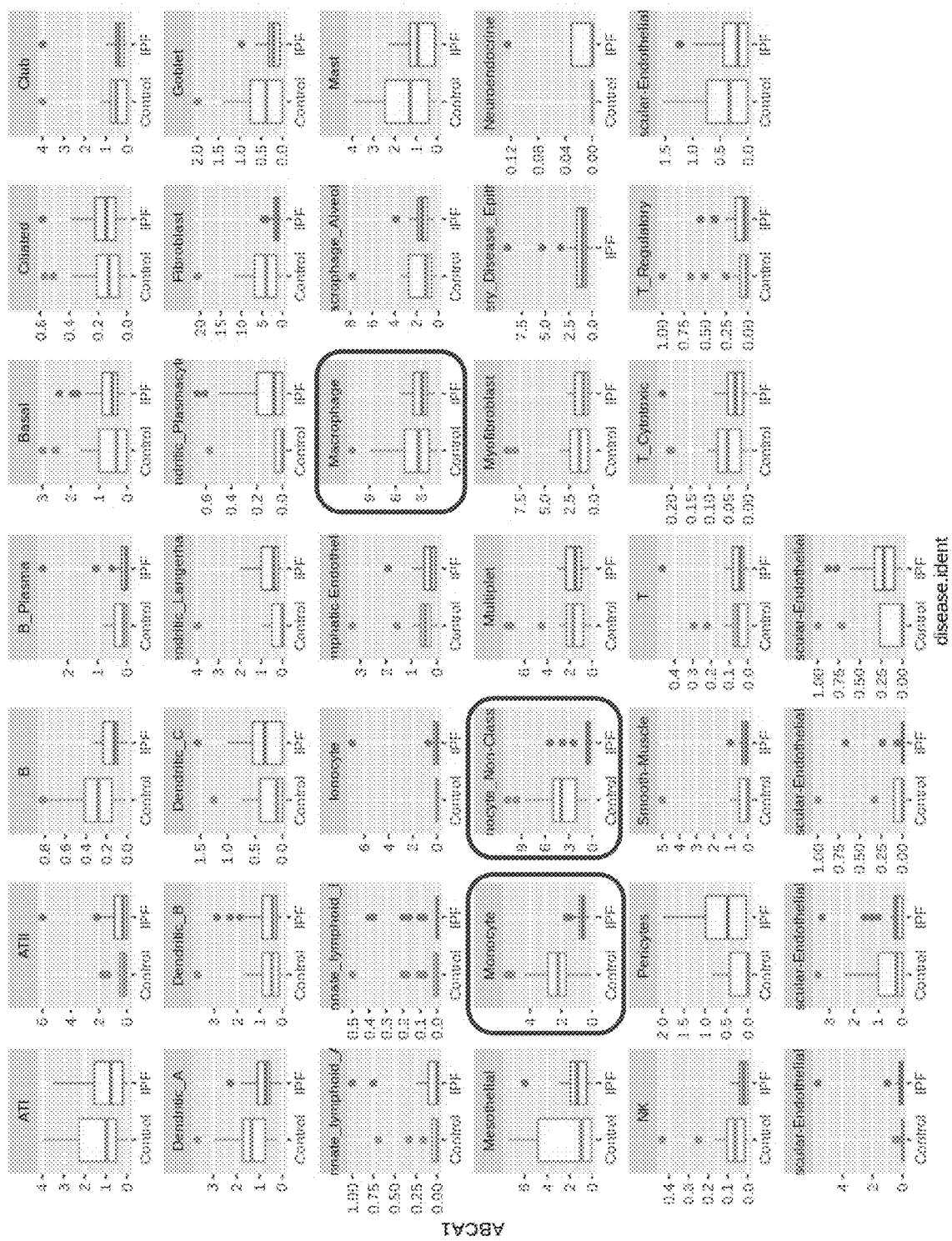
FIG. 10 and FIG. 11 show that ABCA1 (top miR-33 target gene) is decreased in lung monocytes/macrophage cells in IPF vs control (IPF Cell Atlas data), in accordance with some embodiments.
Figure 11:
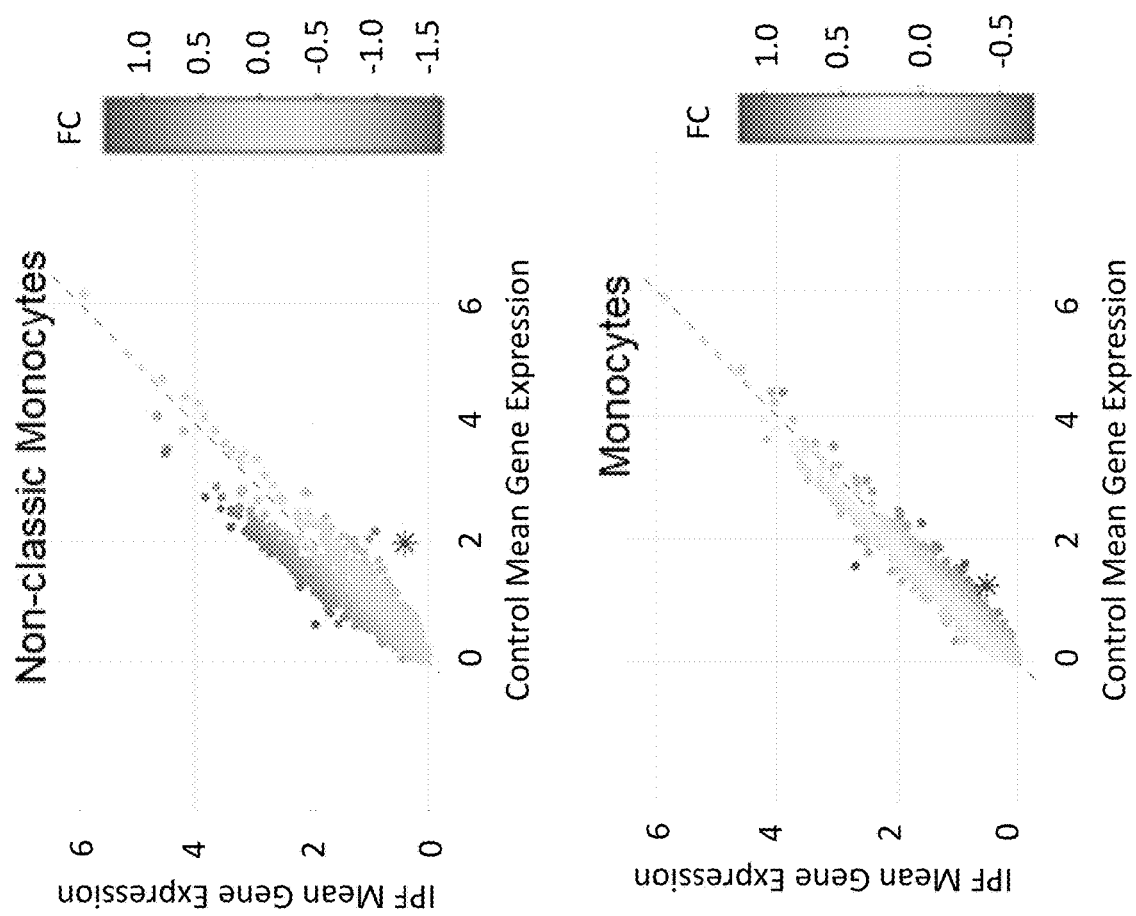

FIG. 10 and FIG. 11 show that ABCA1 (top miR-33 target gene) is decreased in lung monocytes/macrophage cells in IPF vs control (IPF Cell Atlas data)

FIG. 12 shows that macrophage specific miR-33 KO is protective against bleomycin-induced pulmonary fibrosis.

Figure 13B:
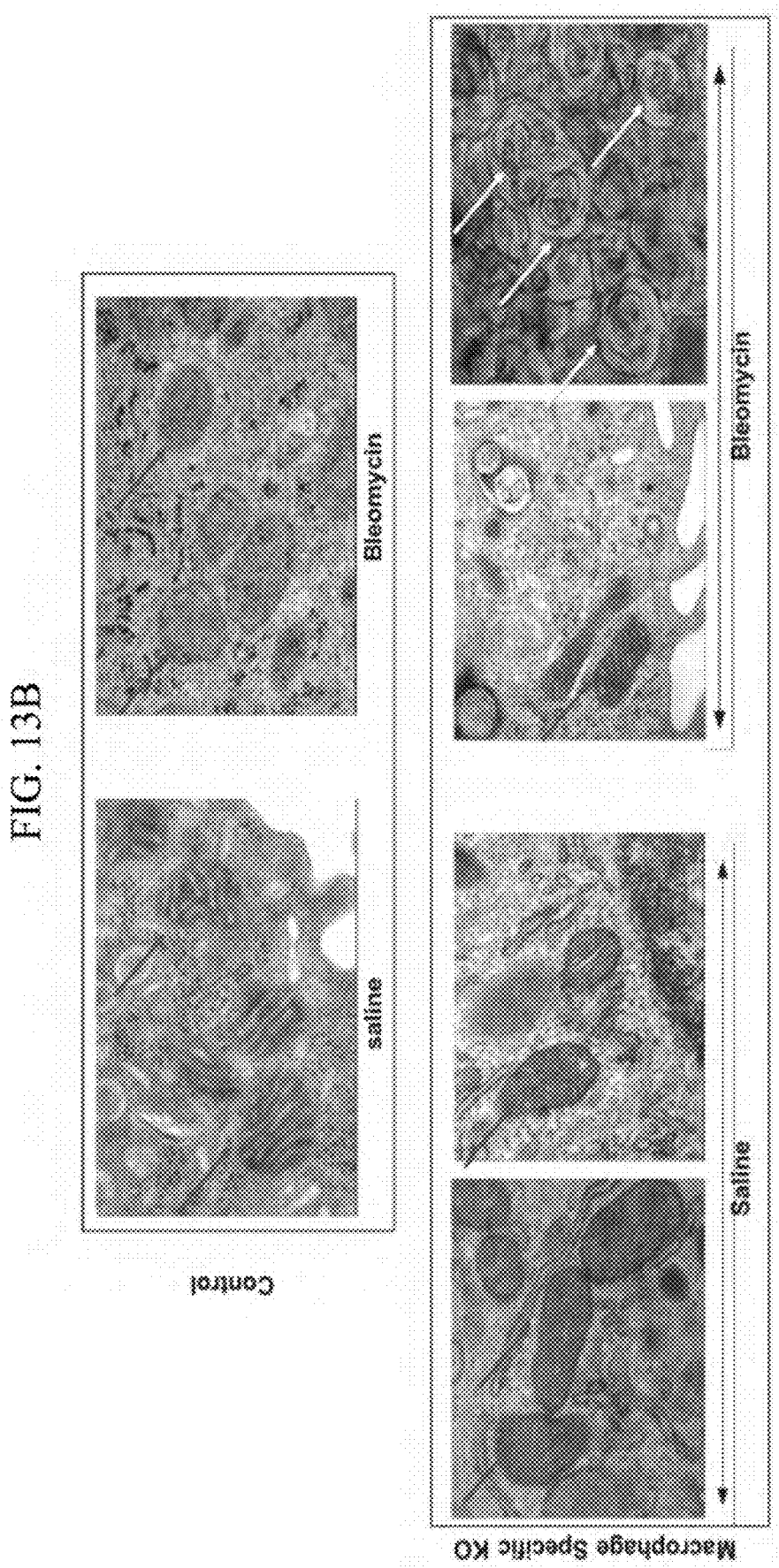
Figure 14:
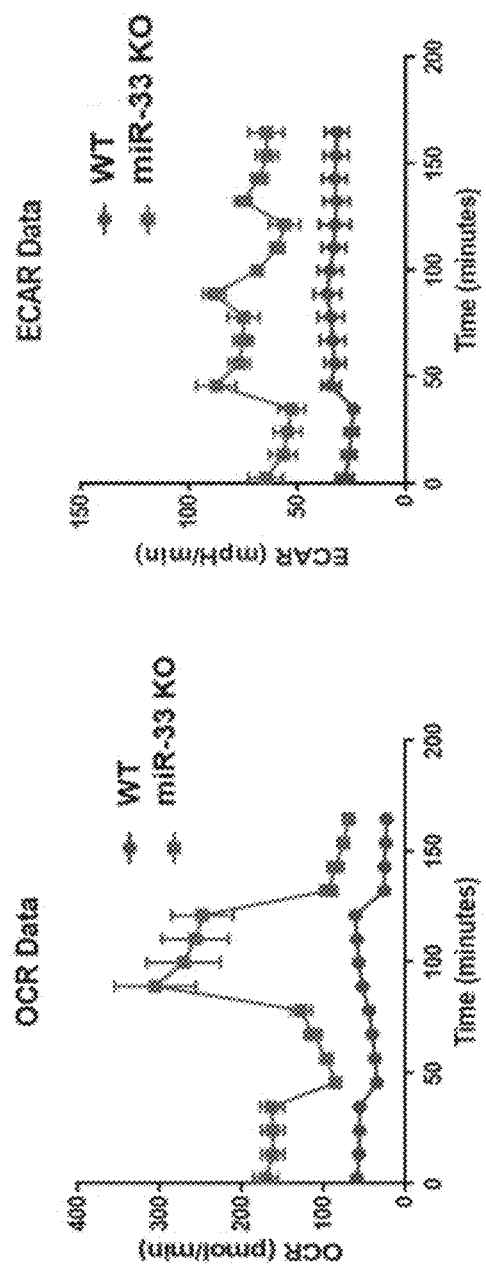

FIGS. 13A-13B and FIG. 14 depict that the absence of miR-33 in macrophages enhances mitochondrial homeostasis and autophagy after bleomycin injury. FIG. 13B depicts that, in macrophage specific MiR-33 KO mice after bleomycin, the mitochondria maintain their normal looking structures and autophagosomes are dramatically increased (red arrows: mitochondria, white arrows: autophagosomes).

Figure 15:
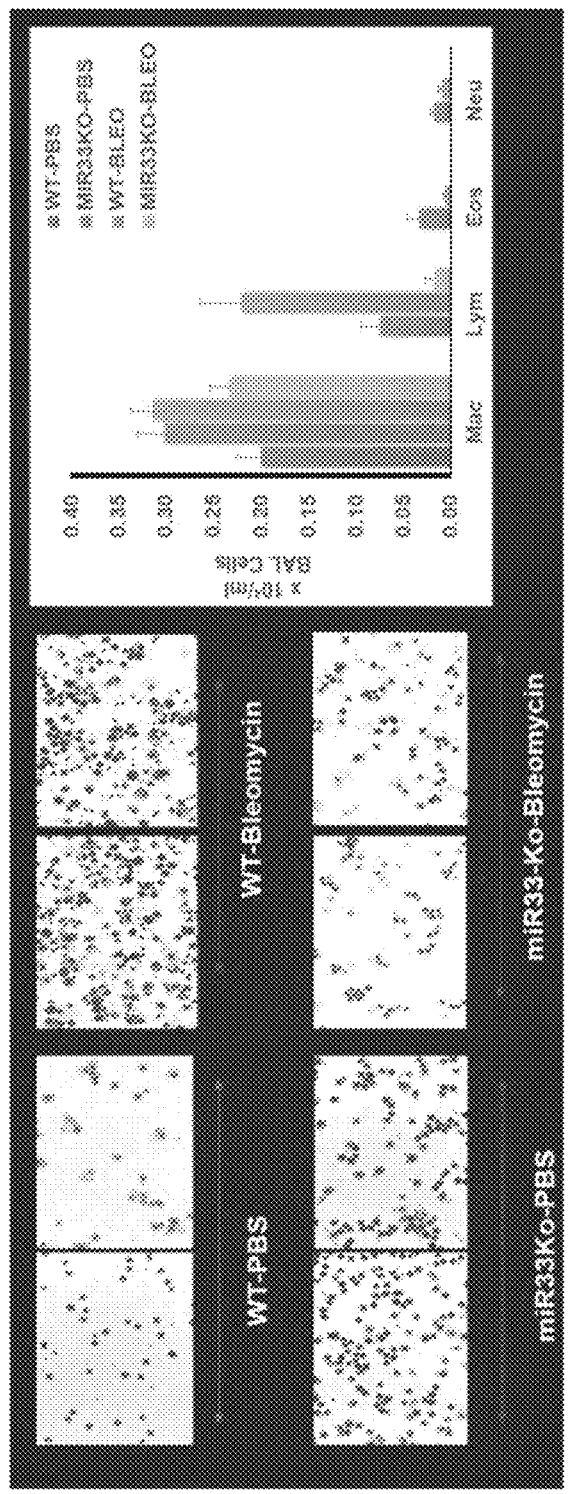
FIG. 15 shows that, in miR-33 KO, BAL cell recovery is augmented at baseline and reduced after bleomycin injury, in accordance with some embodiments.

FIG. 15 shows that, in miR-33 KO, BAL cell recovery is augmented at baseline and reduced after bleomycin injury.

Figure 16:
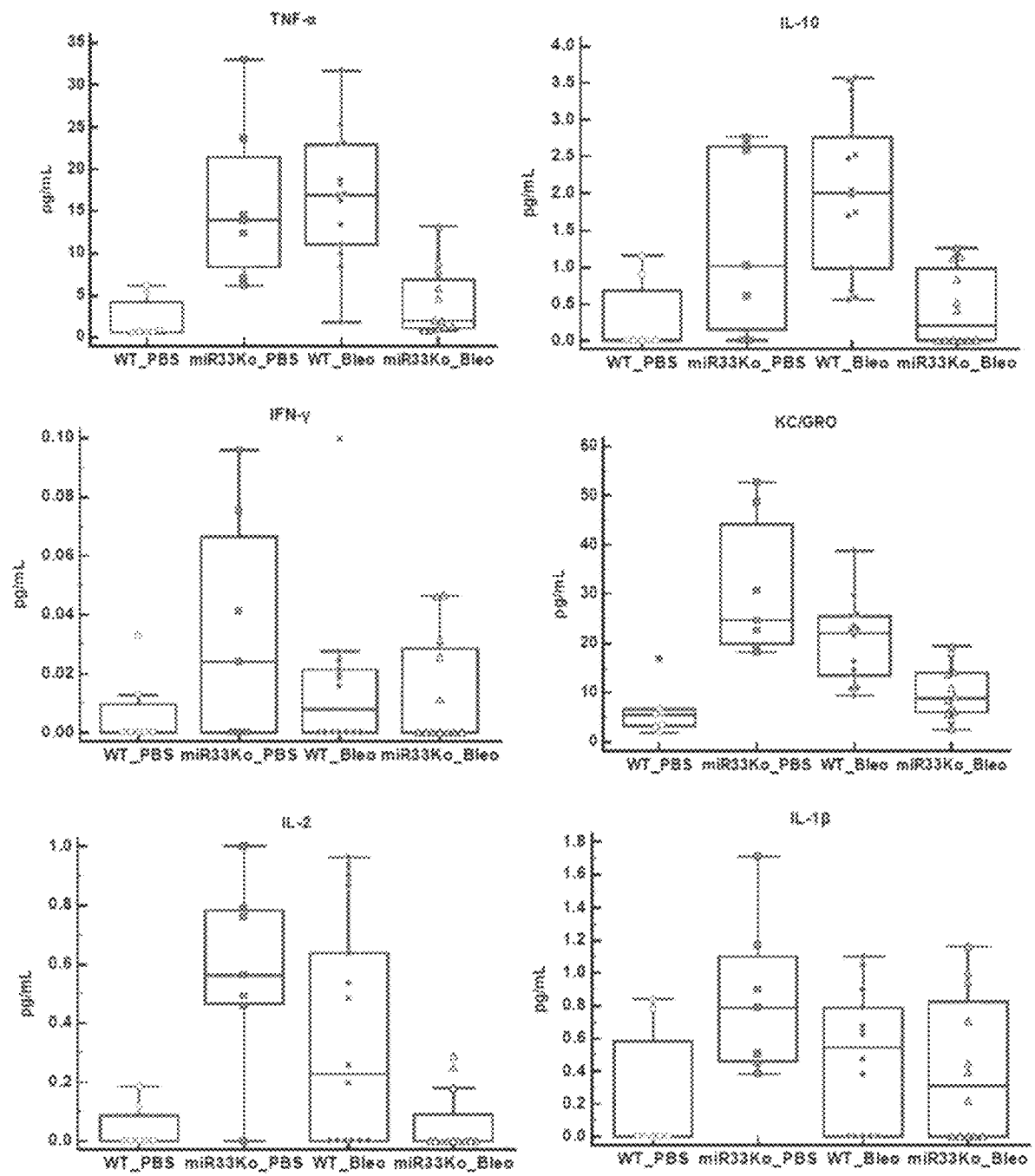
FIG. 16 shows that, in miR-33 KO, BAL pro-inflammatory cytokines are augmented at baseline and reduced after bleomycin injury, in accordance with some embodiments.

FIG. 16 shows that, in miR-33 KO, BAL pro-inflammatory cytokines are augmented at baseline and reduced after bleomycin injury.

Figure 17:
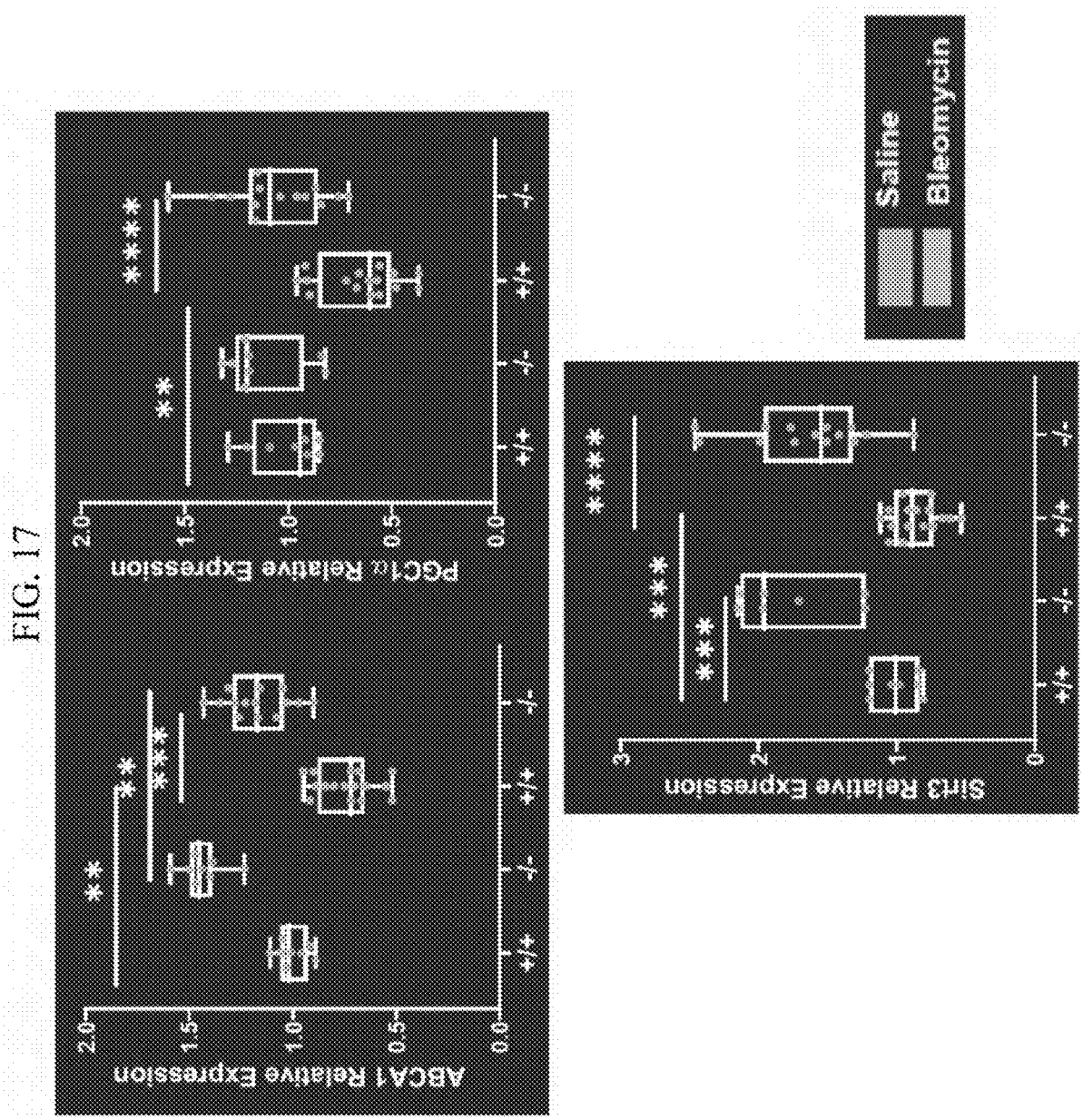
FIG. 17 shows that, in the absence of miR-33 in macrophages, miR-33 target genes relevant to mitochondrial homeostasis are increased at baseline and after bleomycin injury, in accordance with some embodiments.

FIG. 17 shows that, in the absence of miR-33 in macrophages, miR-33 target genes relevant to mitochondrial homeostasis are increased at baseline and after bleomycin injury.

Figure 18:
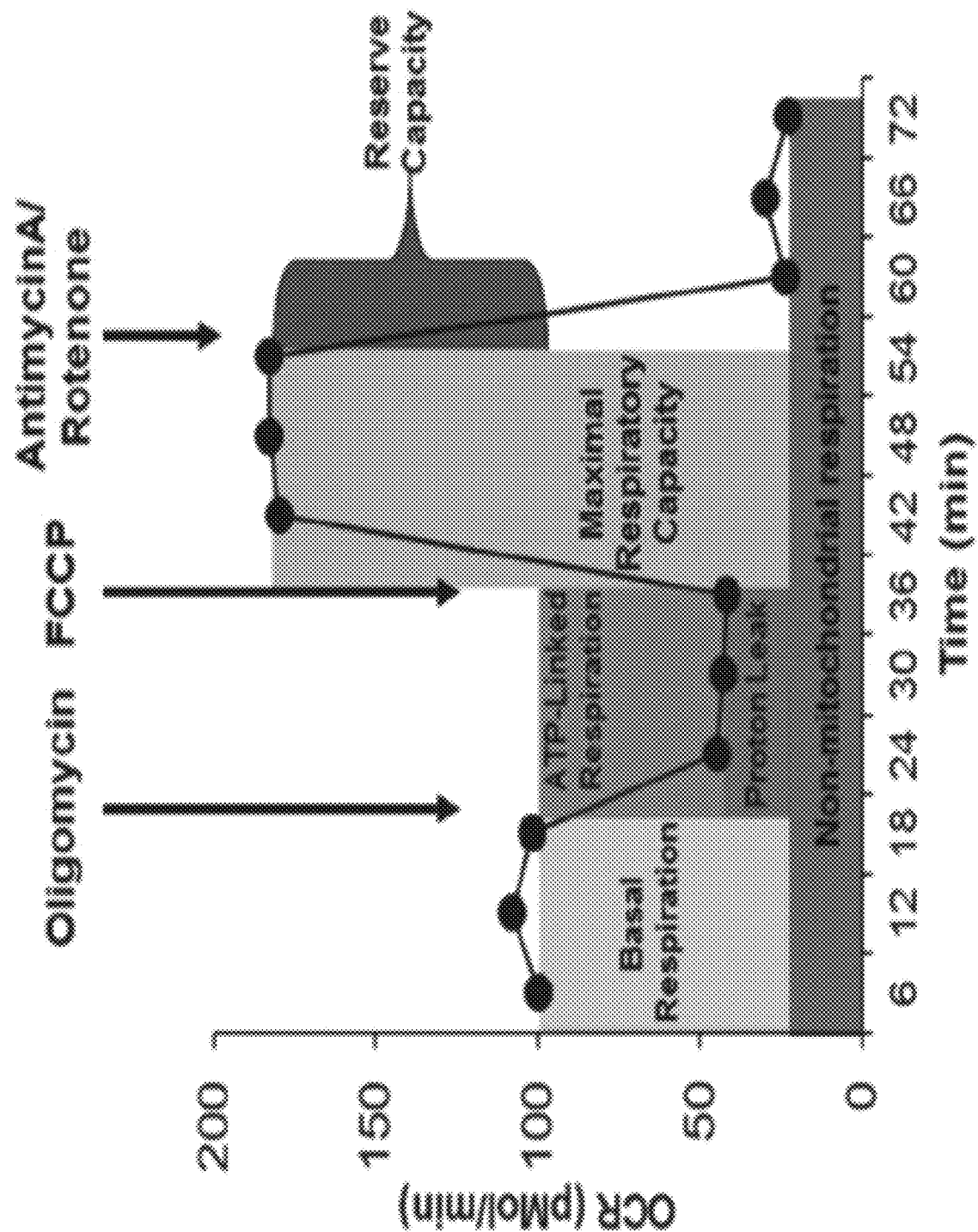
FIG. 18 and FIG. 19 show that the absence of miR-33 in macrophages, improves mitochondrial homeostasis (OCR is increased at baseline and after bleomycin injury), in accordance with some embodiments.
Figure 19:
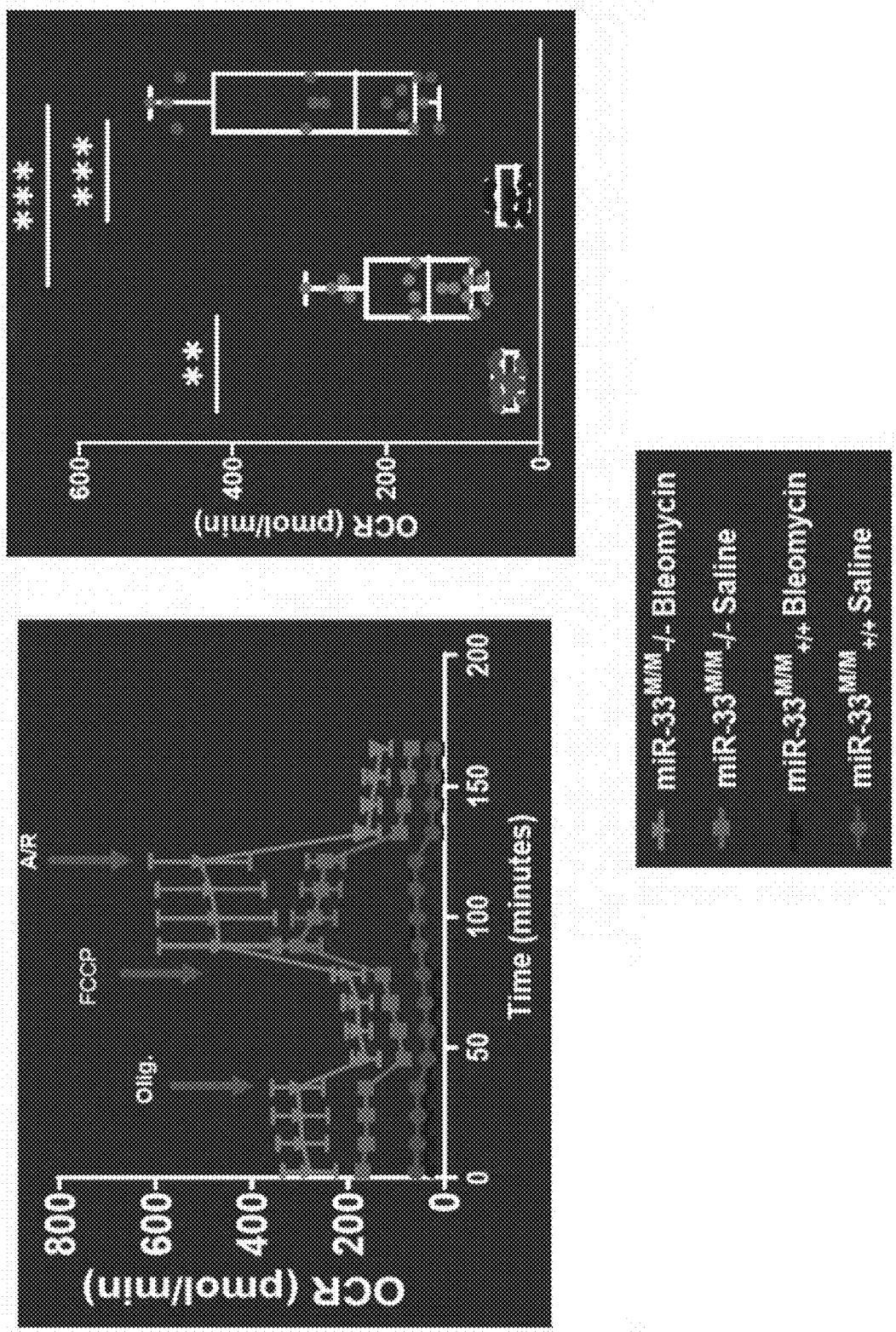

FIG. 18 and FIG. 19 show that the absence of miR-33 in macrophages, improves mitochondrial homeostasis (OCR is increased at baseline and after bleomycin injury).

Figure 20:
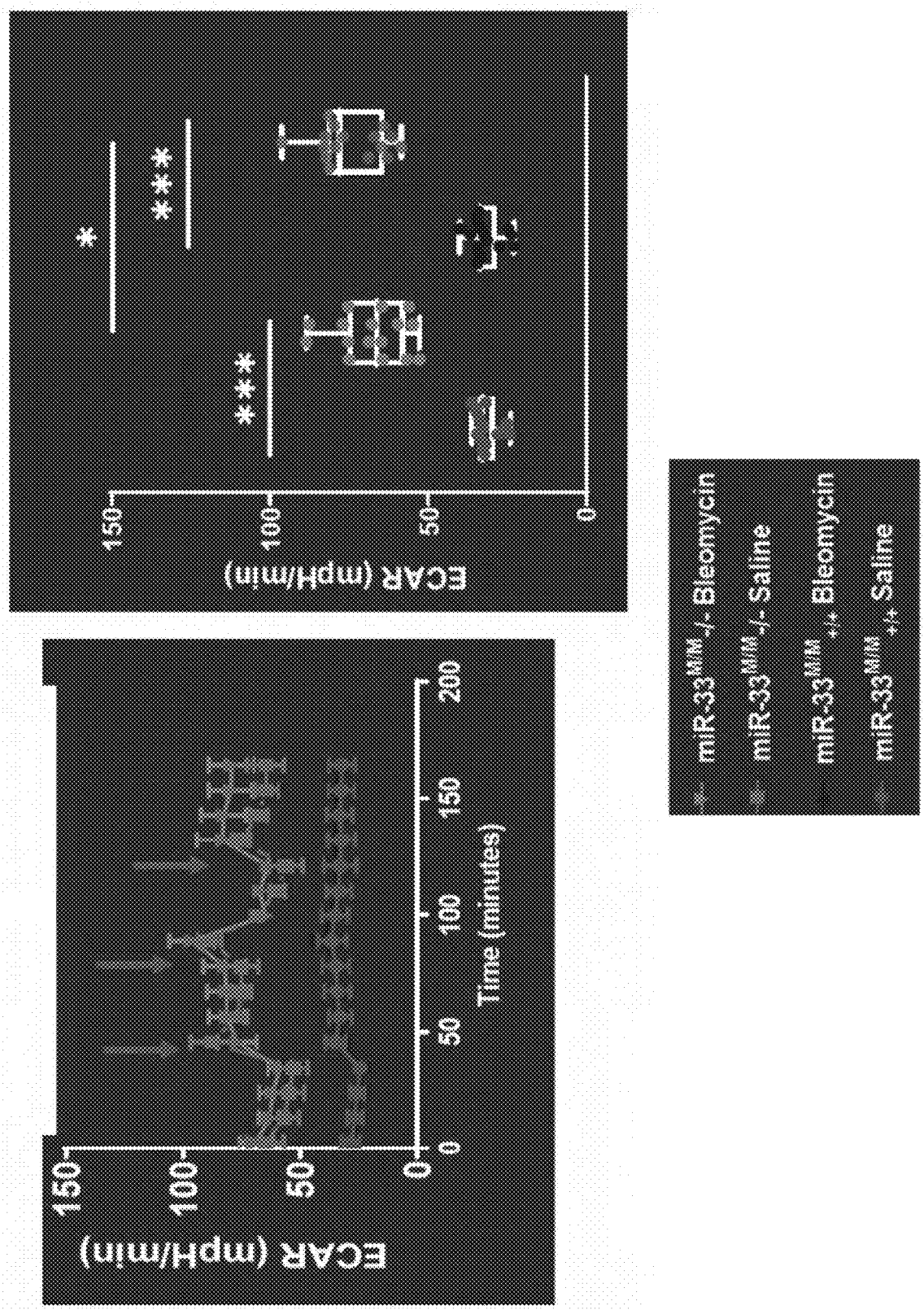
FIG. 20 shows that the absence of miR-33 in macrophages, improves mitochondrial homeostasis (ECAR is increased at baseline and after bleomycin injury), in accordance with some embodiments.

FIG. 20 shows that the absence of miR-33 in macrophages, improves mitochondrial homeostasis (ECAR is increased at baseline and after bleomycin injury).

Figure 21:
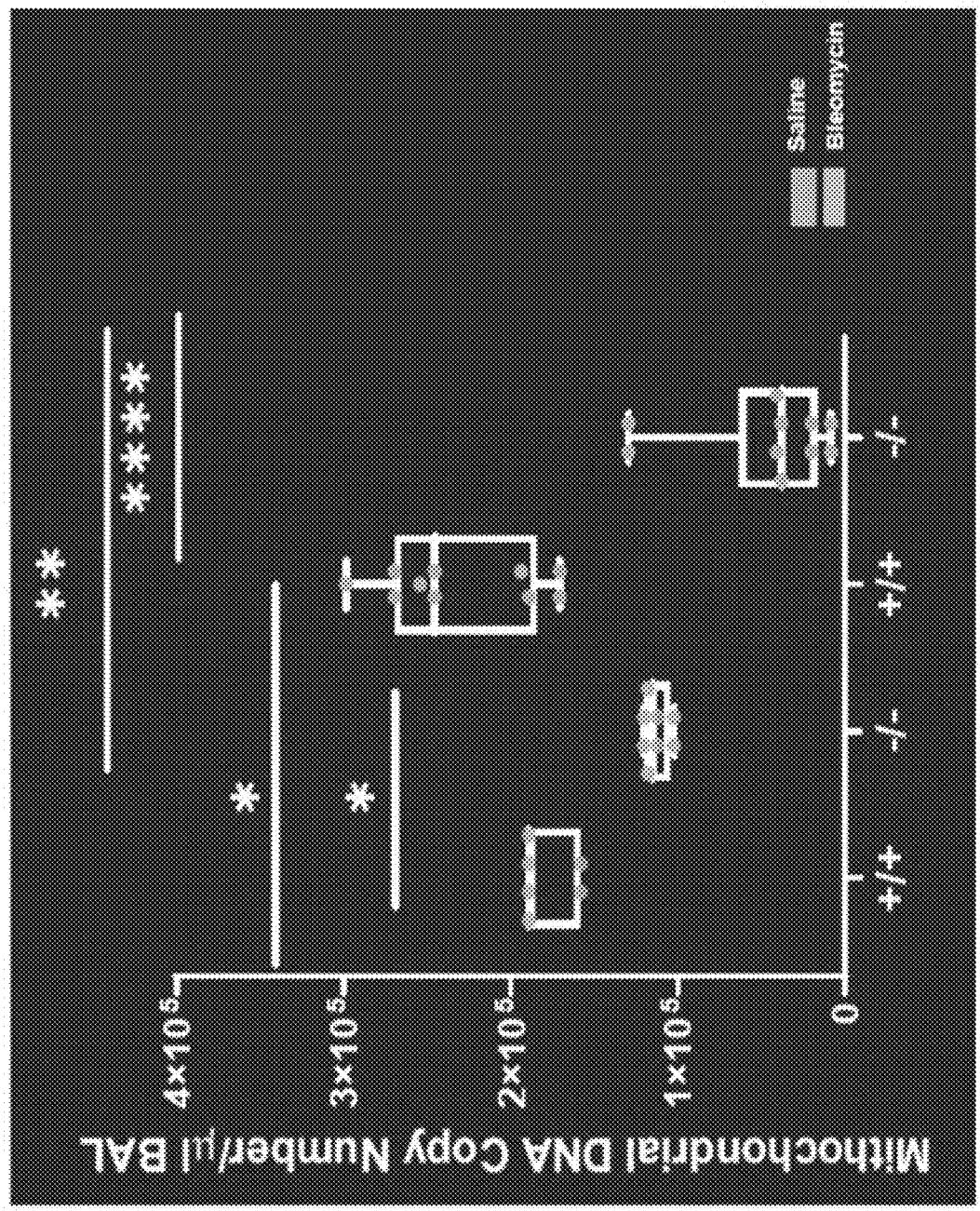
FIG. 21 shows that, in the absence of miR-33 in macrophages, bleomycin-induced mtDNA release in BAL is reduced, in accordance with some embodiments.

FIG. 21 shows that, in the absence of miR-33 in macrophages, bleomycin-induced mtDNA release in BAL is reduced.

Figure 22:
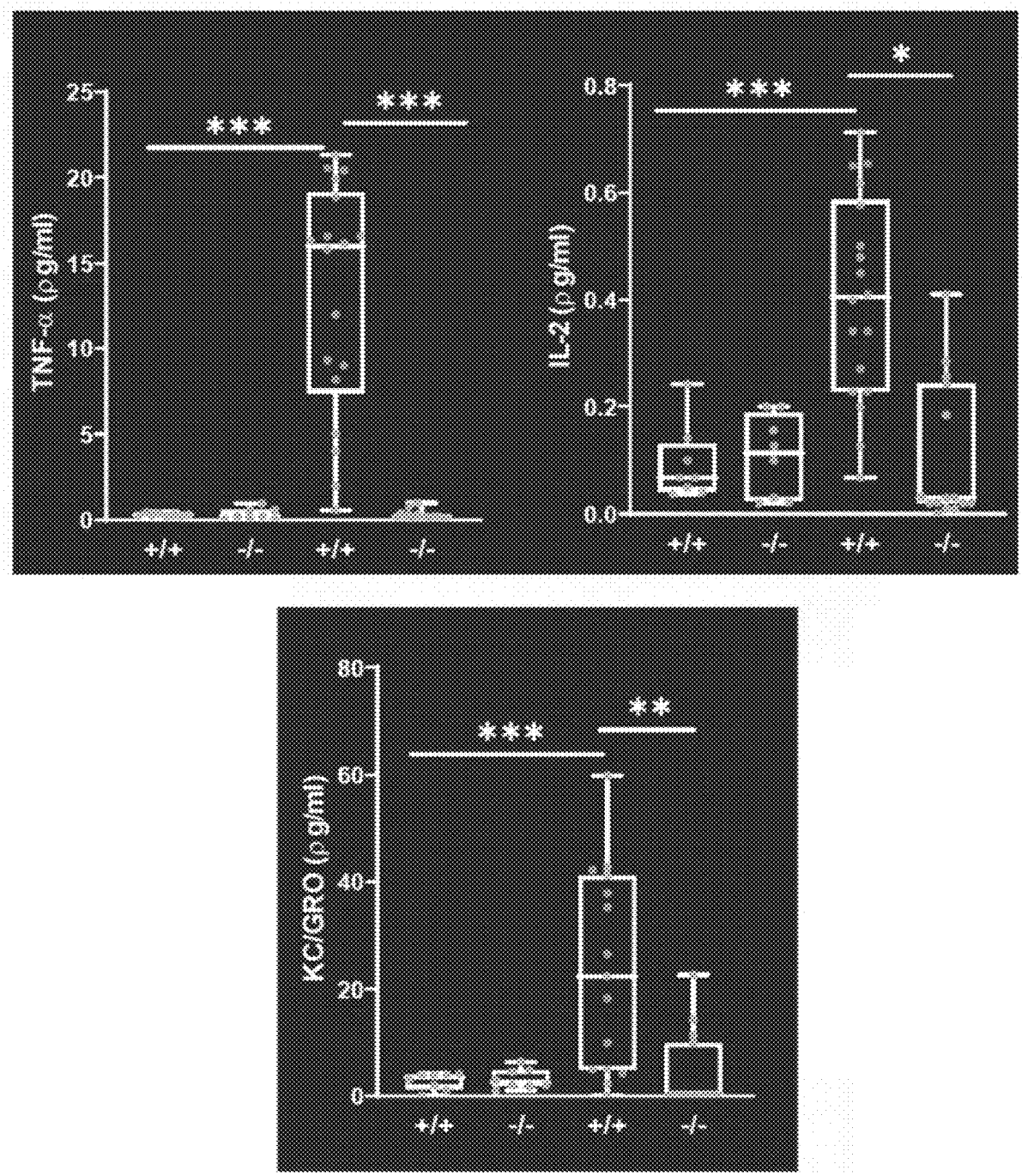
FIG. 22 shows that some BAL inflammatory cytokines change in the absence of miR-33 in macrophages, in accordance with some embodiments.

FIG. 22 shows that some BAL inflammatory cytokines change in the absence of miR-33 in macrophages.

Figure 23:
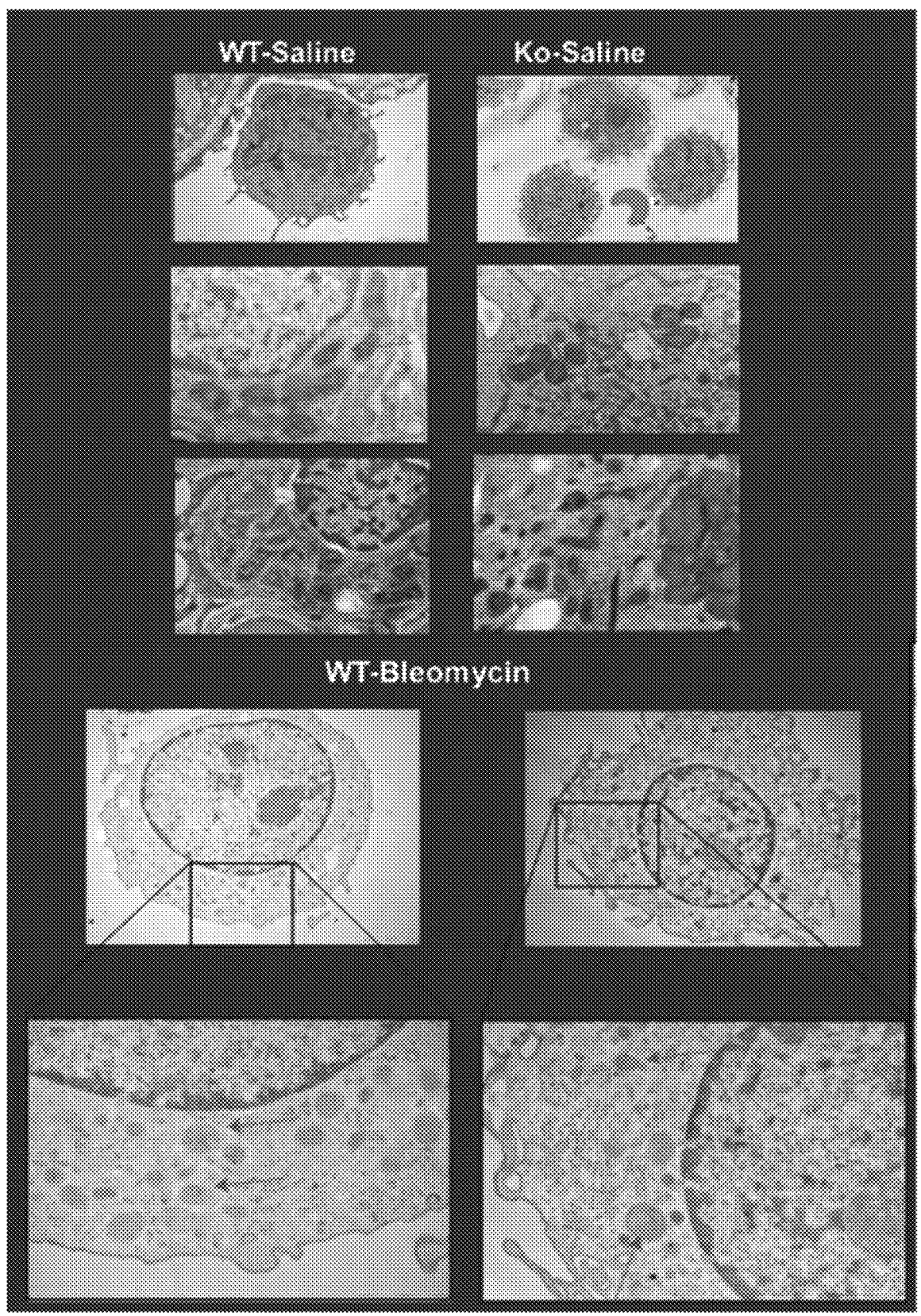
FIG. 23 and FIG. 24 provide images of lung tissues showing that the absence of miR-33 in macrophages improves mitochondrial homeostasis (structure) at baseline and after bleomycin injury, in accordance with some embodiments.
Figure 24:
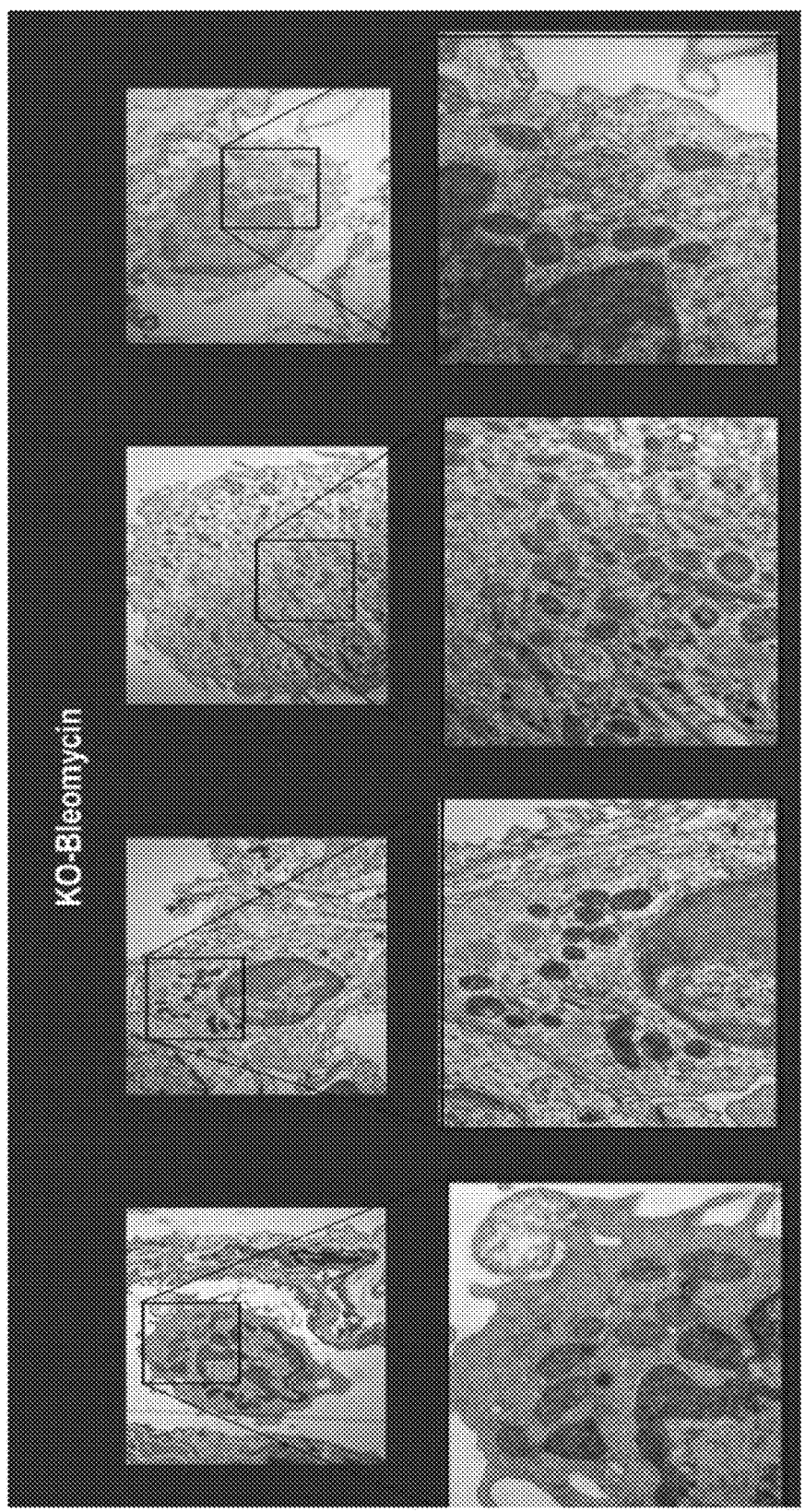

FIG. 23 and FIG. 24 provide images of lung tissues showing that the absence of miR-33 in macrophages improves mitochondrial homeostasis (structure) at baseline and after bleomycin injury.

Figure 25:
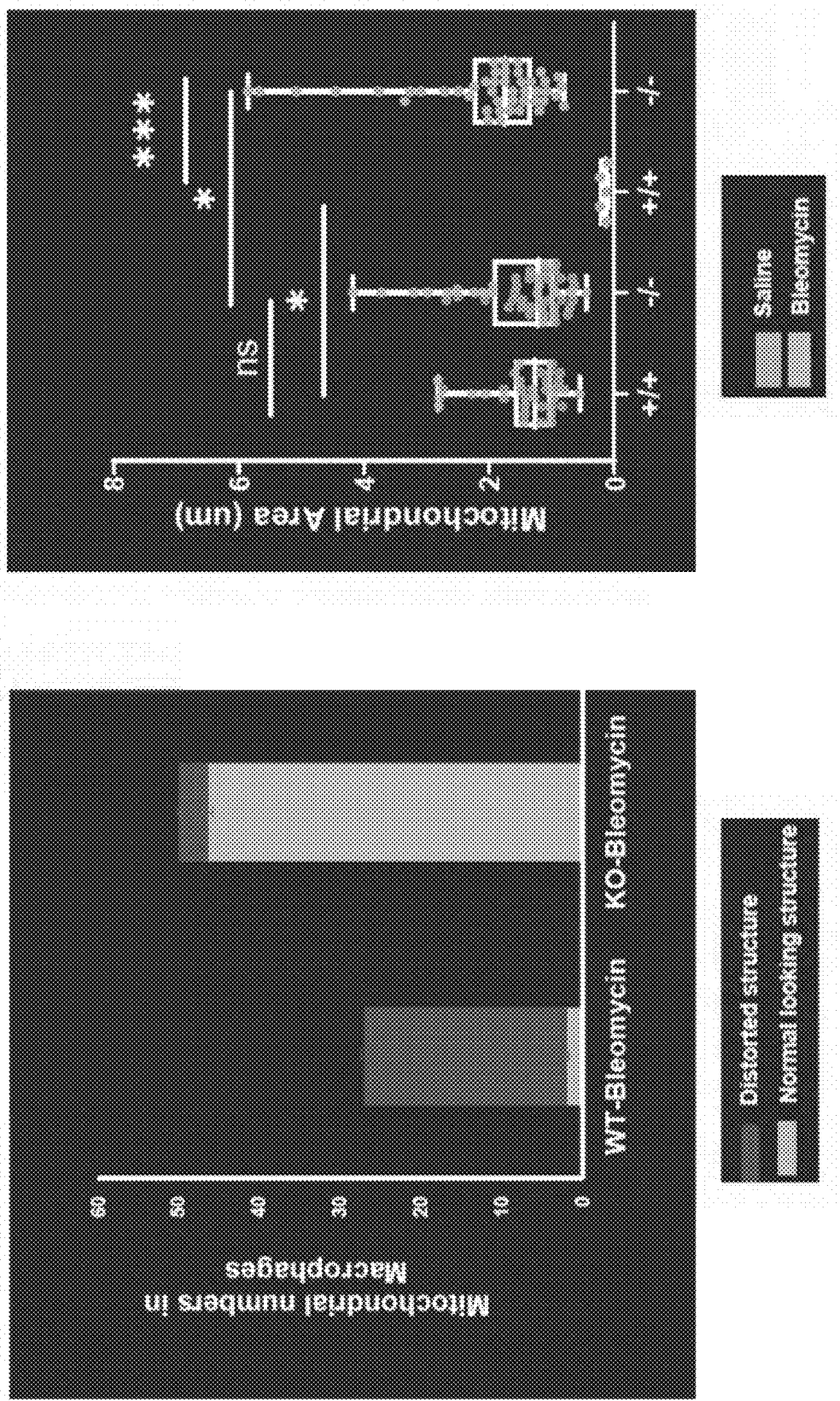
FIG. 25 depicts that, in the absence of miR-33 in macrophages, there is an increase in the number and area of healthy mitochondria after bleomycin injury, in accordance with some embodiments.

FIG. 25 depicts that, in the absence of miR-33 in macrophages, there is an increase in the number and area of healthy mitochondria after bleomycin injury.

Figure 26:
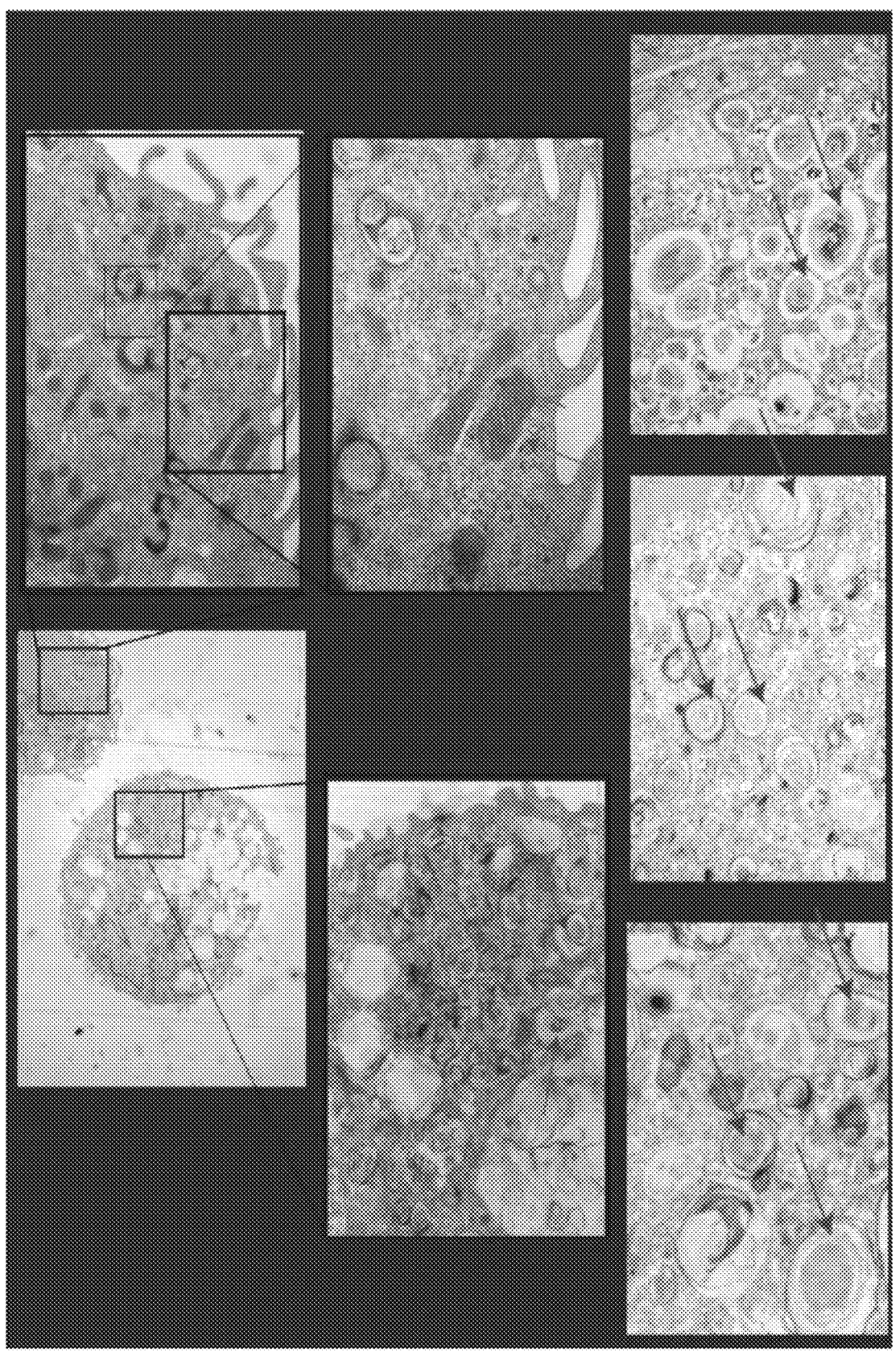
FIG. 26 provides images of lung tissues showing that the absence of miR-33 in macrophages augments autophagy after bleomycin injury, in accordance with some embodiments.

FIG. 26 provides images of lung tissues showing that the absence of miR-33 in macrophages augments autophagy after bleomycin injury.

Figure 27:
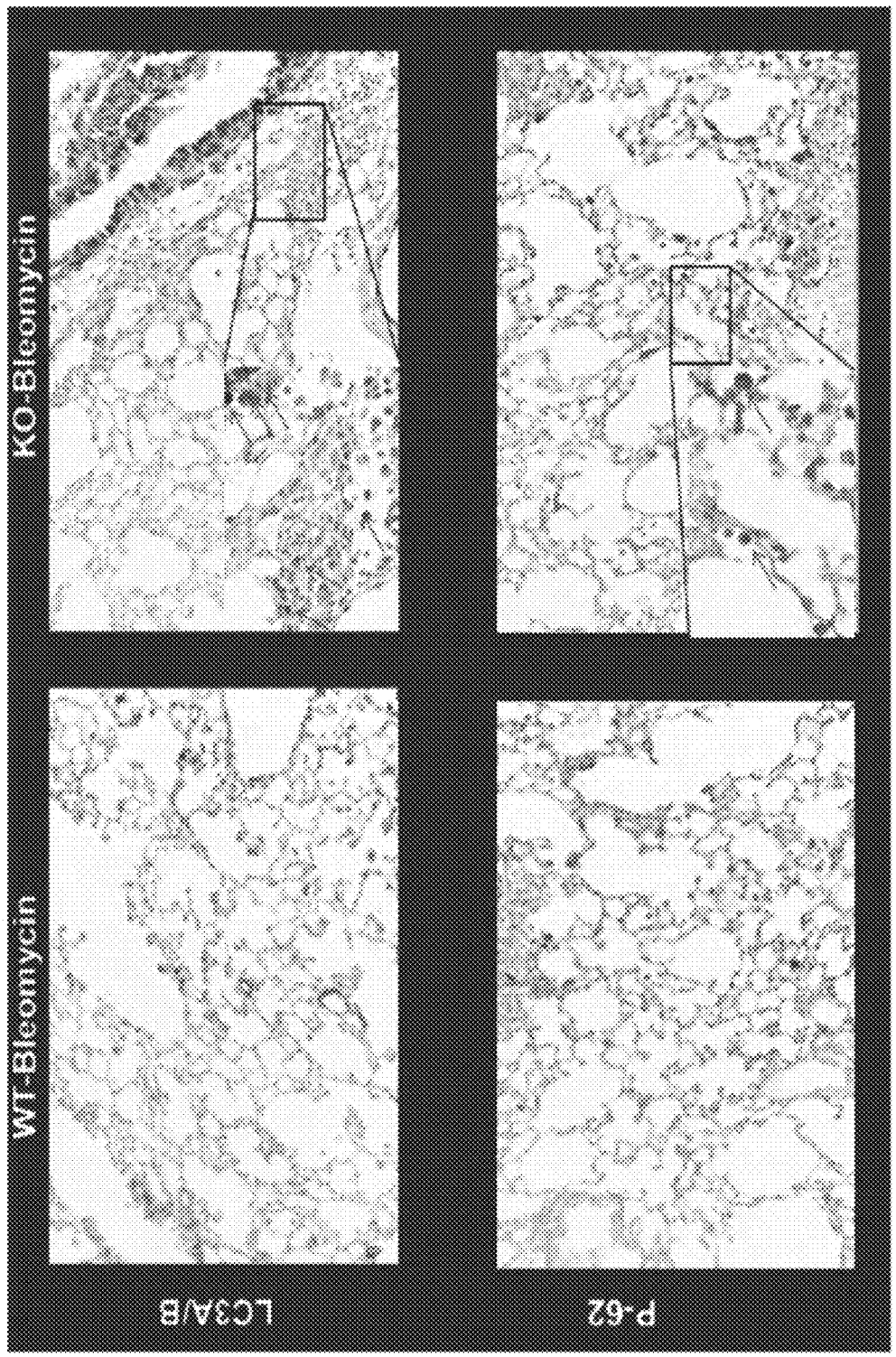
FIG. 27, FIG. 28, and FIG. 29 show that the absence of miR-33 in macrophages augments autophagy through the LC3A/B P62 pathway, in accordance with some embodiments.
Figure 28:
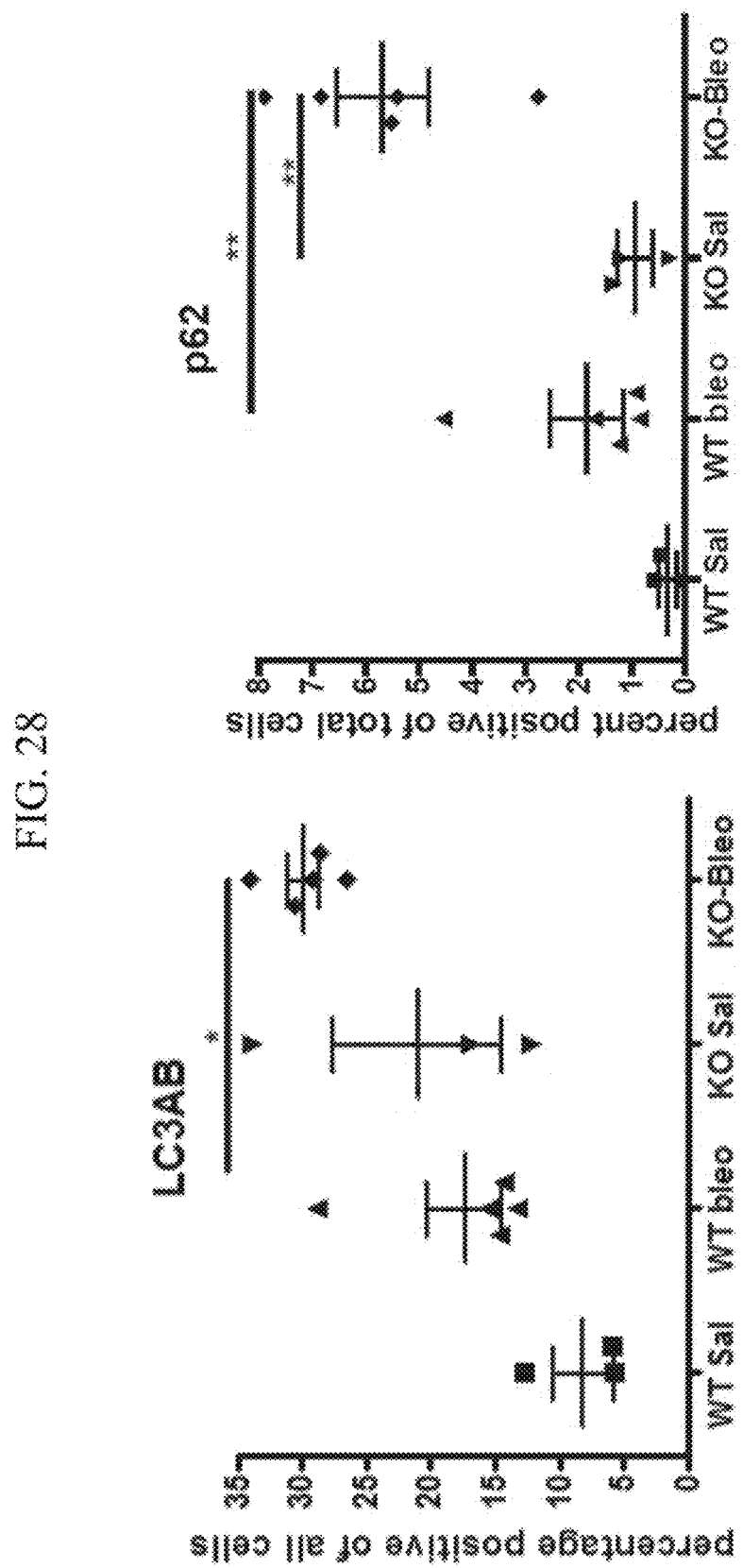
Figure 29:
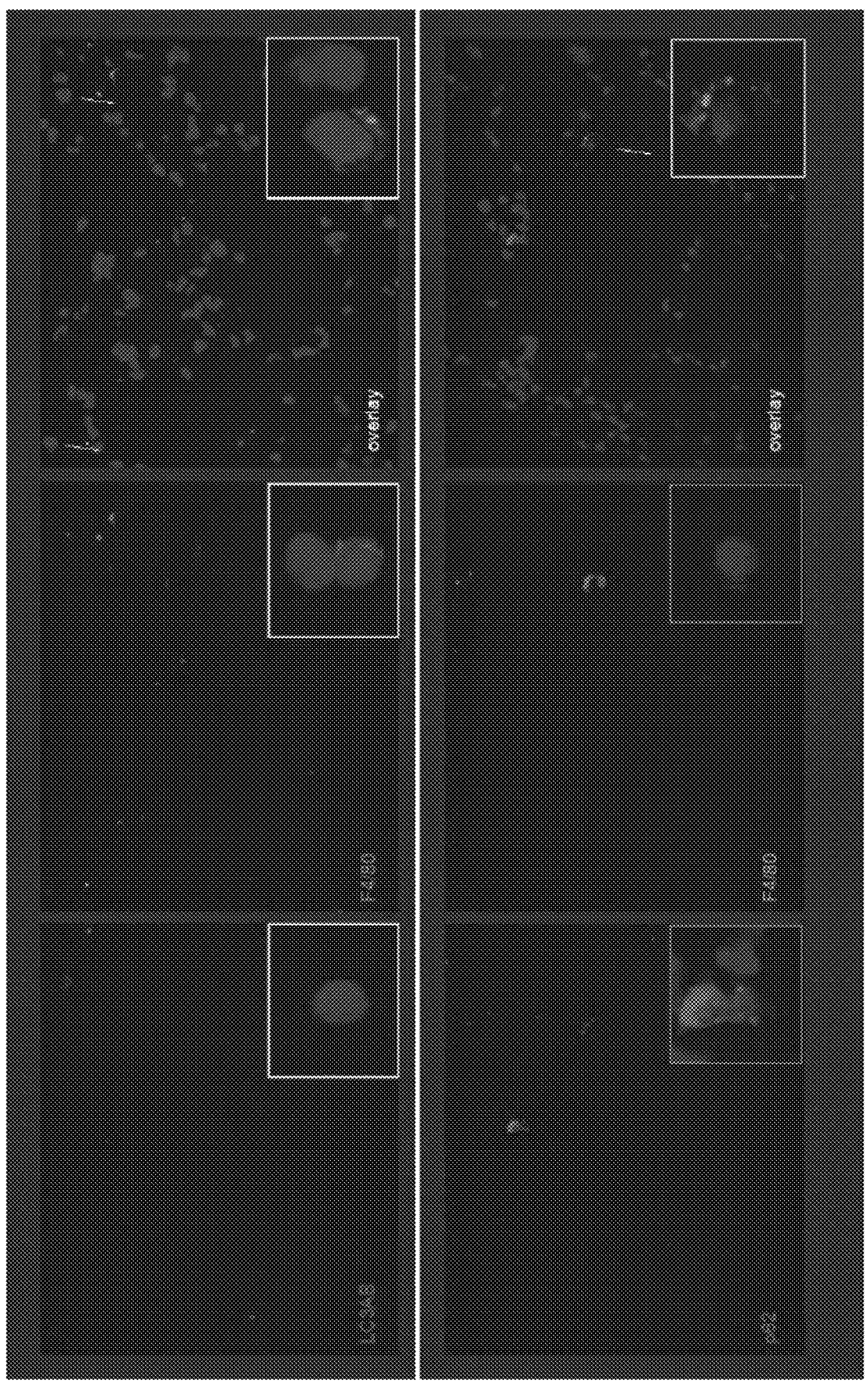

FIG. 27, FIG. 28, and FIG. 29 show that the absence of miR-33 in macrophages augments autophagy through the LC3A/B P62 pathway.

Figure 30:
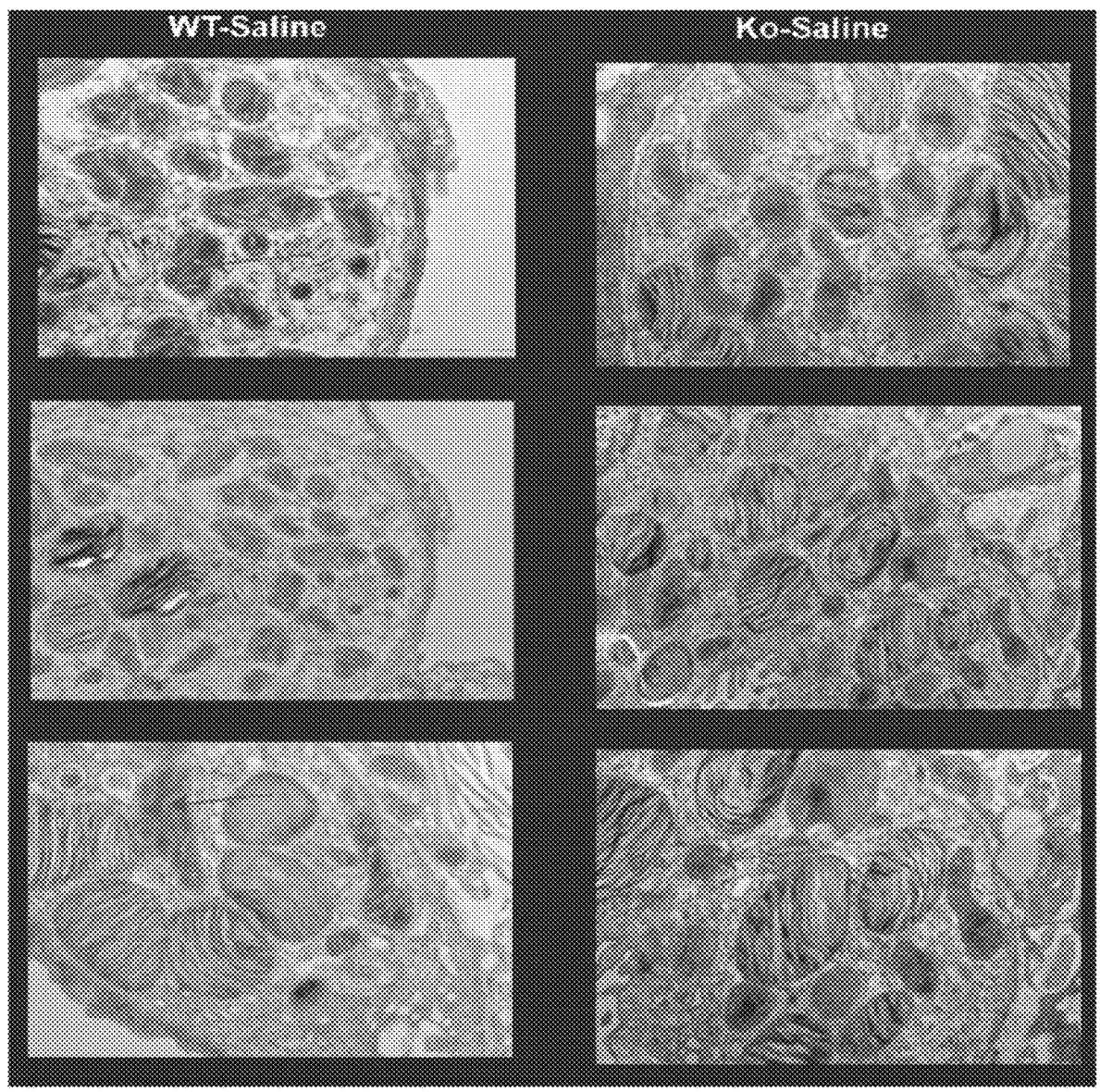
FIG. 30 and FIG. 31 provide images of lung tissues showing that the absence of miR-33 in macrophages improves mitochondrial homeostats in AEC-II cells, in accordance with some embodiments.
Figure 31:
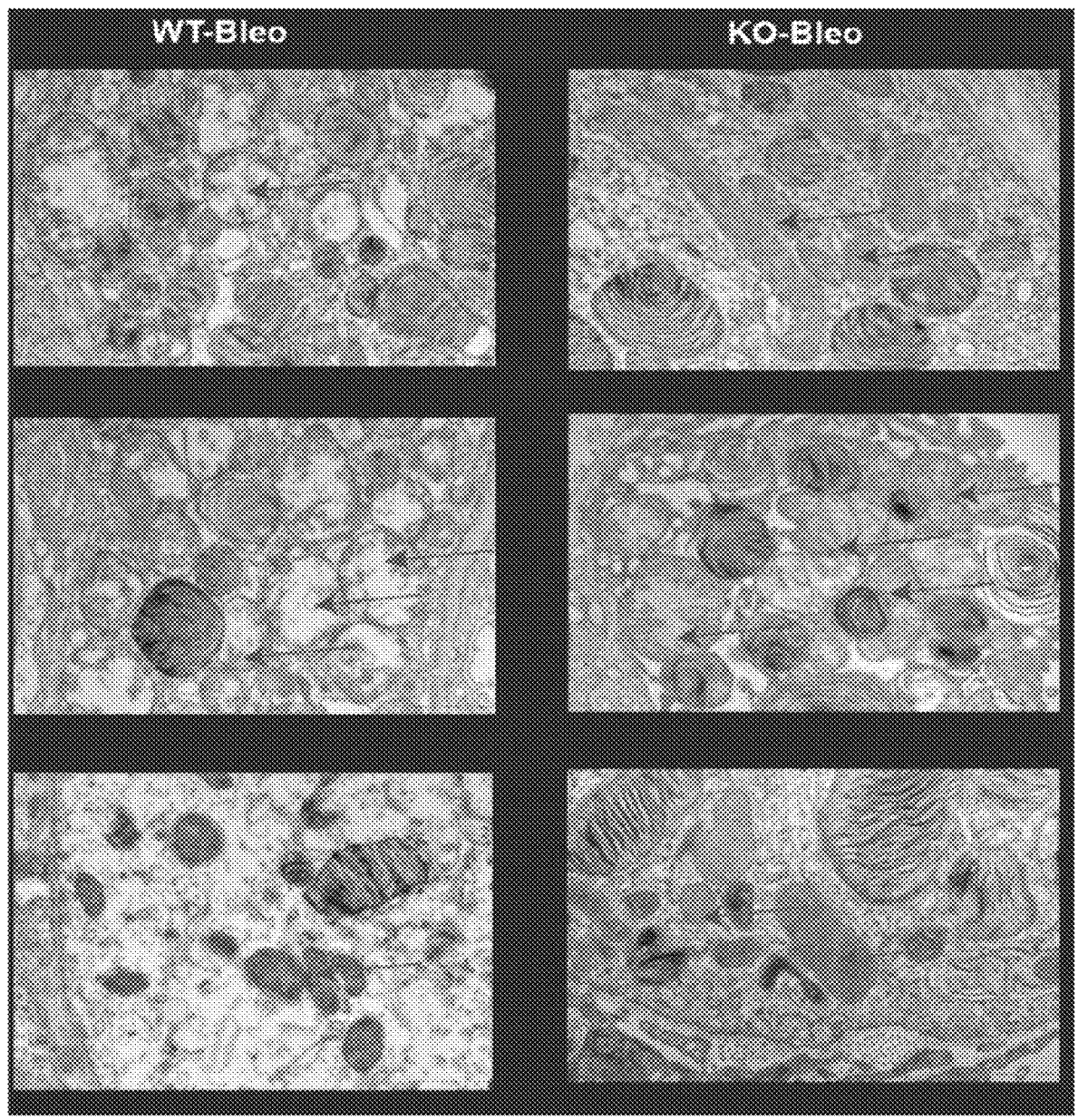

FIG. 30 and FIG. 31 provide images of lung tissues showing that the absence of miR-33 in macrophages improves mitochondrial homeostats in AEC-II cells.

Figure 32:
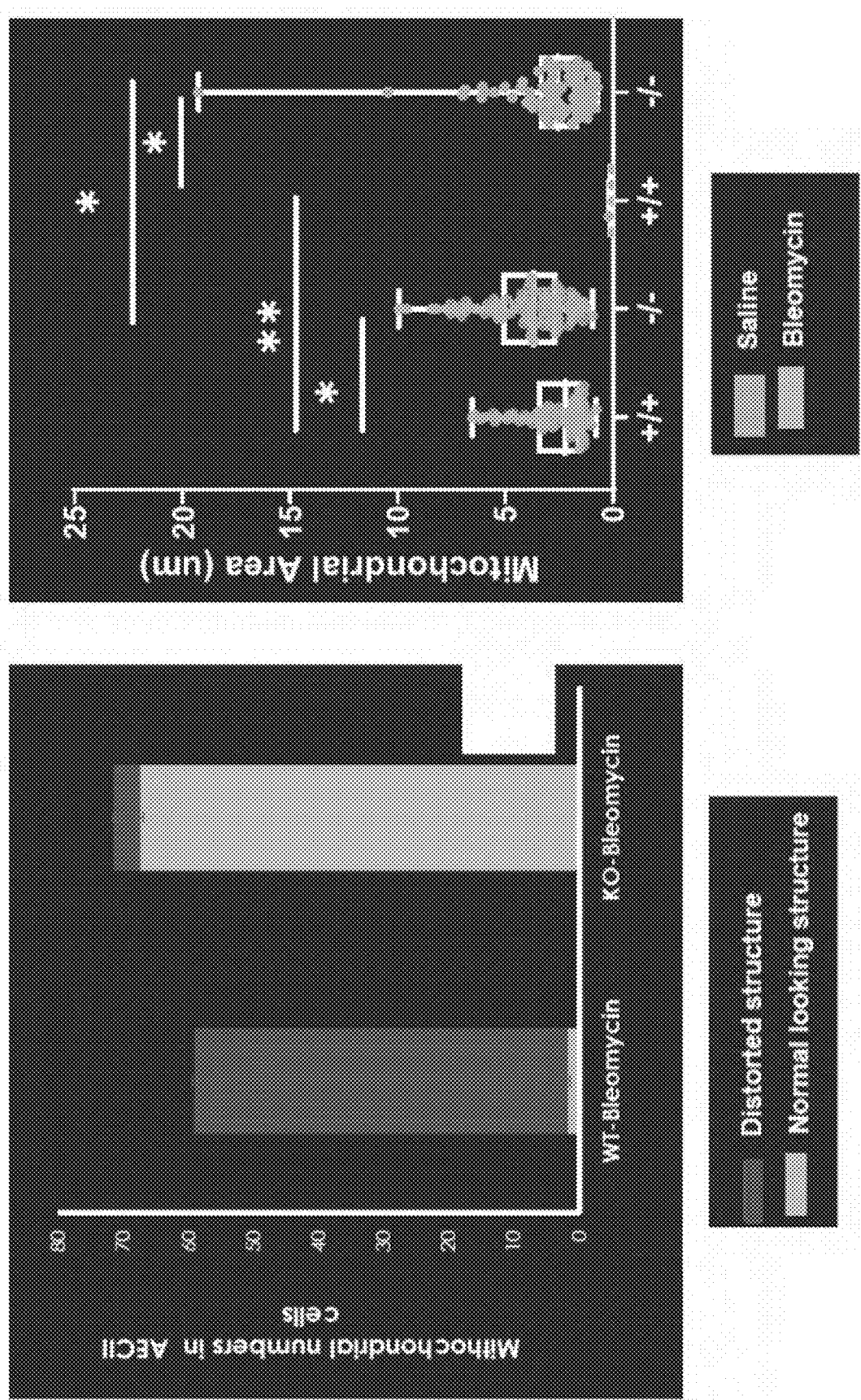
FIG. 32 contains plots demonstrating that, in the absence of miR-33 in macrophages, there is an increase in the number and area of healthy mitochondria in AEC-II cells after bleomycin injury, in accordance with some embodiments.

FIG. 32 contains plots demonstrating that, in the absence of miR-33 in macrophages, there is an increase in the number and area of healthy mitochondria in AEC-II cells after bleomycin injury.

Figure 33:
Figure 34:
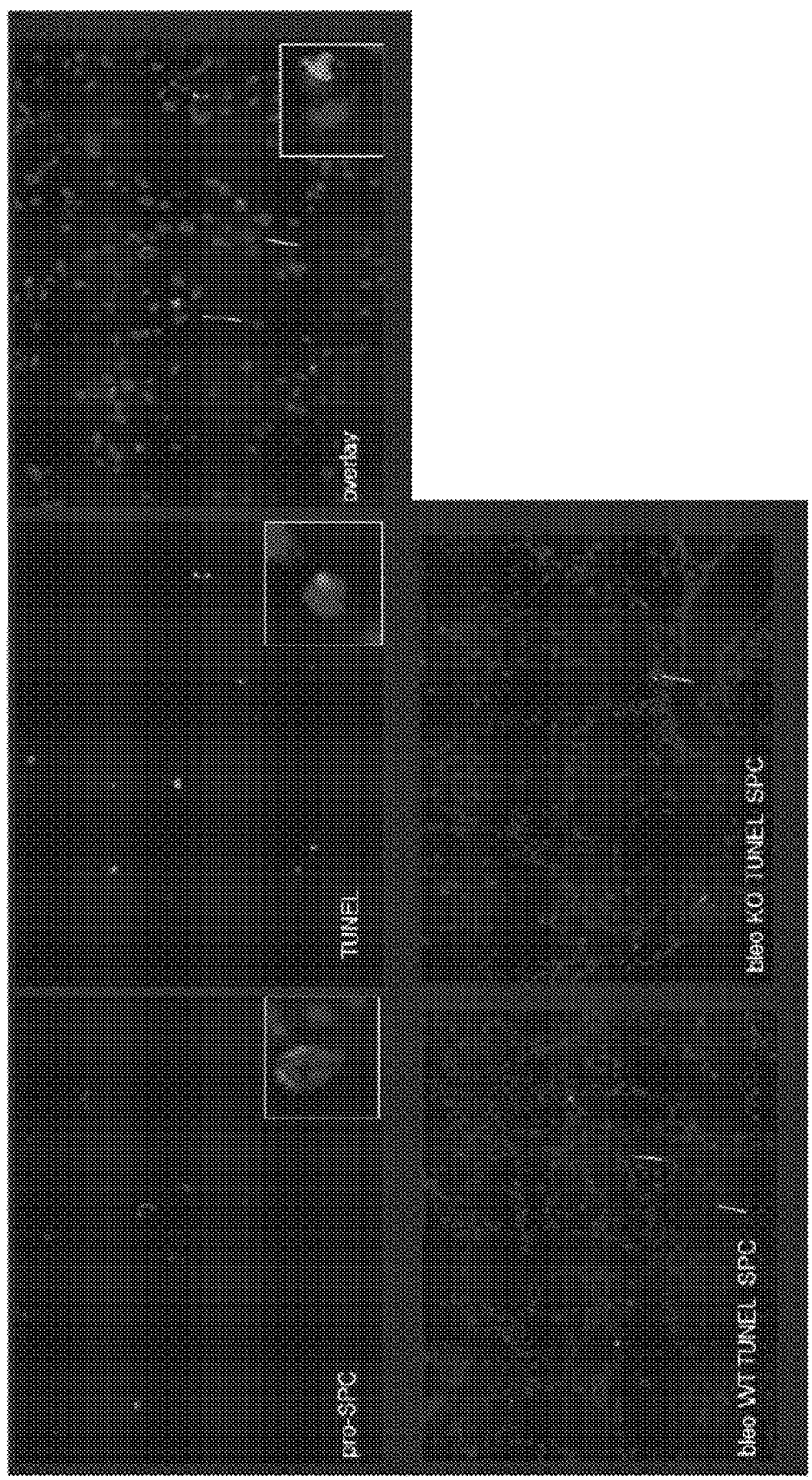

FIG. 33, FIG. 34, and FIG. 35 show that the absence of miR-33 in macrophages reduces bleomycin-induced cell death in AEC-II cells. FIG. 35 further shows that the absence of miR-33 in macrophages has a protective effect against bleomycin-induced cell death in lung and specifically on epithelial cell death. This is done by performing TUNNEL assay combined with SPC marker on the lung tissues from the mice of all the groups.

Figure 36A:
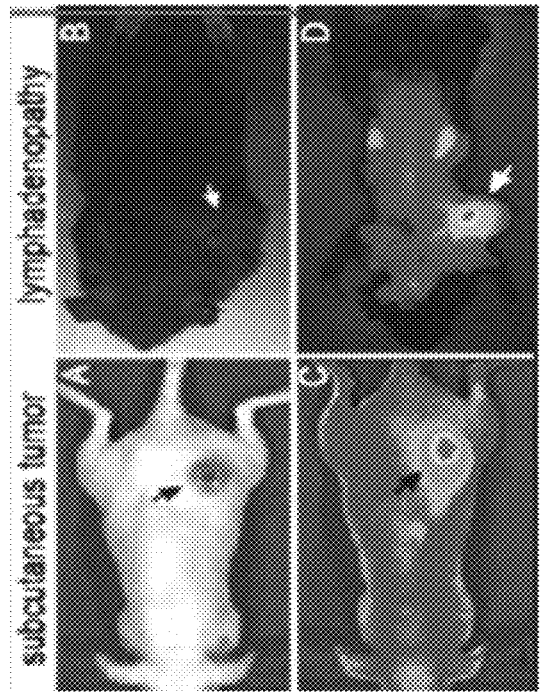
FIG. 36A is a peptide nucleic acid (PNA), which is a synthetic analogue of DNA comprised of nucleobases that are connected to a pseudopeptide backbone through a carboxymethylene linker, in accordance with some embodiments.

Determining the Therapeutic Role of Cell Specific miR-33 Silencing in Pulmonary Fibrosis The growing body of evidence supports the role for macrophages in the pathogenesis of pulmonary fibrosis. Alveolar macrophages are a crucial component of the pulmonary fibrotic response and manipulation of these cells may present an attractive therapeutic strategy. Current anti miR technologies are hindered by physiological and cellular barriers to delivery into targeted cells. Peptide nucleic acids (PNAs) are nucleic acid analogues comprising nucleobases joined by intramolecular amide bonds (FIG. 36A), which leads to increased binding affinity for complementary nucleic acids. The exemplary pHLIP used herein is a peptide that forms an inducible transmembrane a-helix which mediates lipid membrane translocation via a non-endocytic route.

Figure 36B:
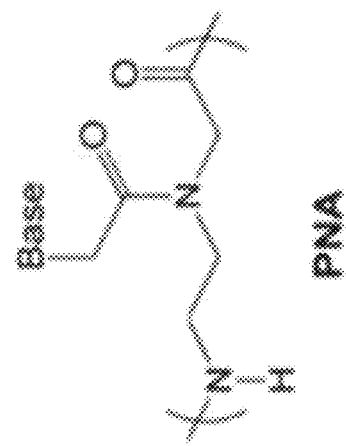
FIG. 36B shows the tumor targeting ability of PNAs in vivo wherein accumulations of conjugated PNA can be seen in the tumor 48 hours after intravenous injection, in accordance with some embodiments.
Figure 36C:
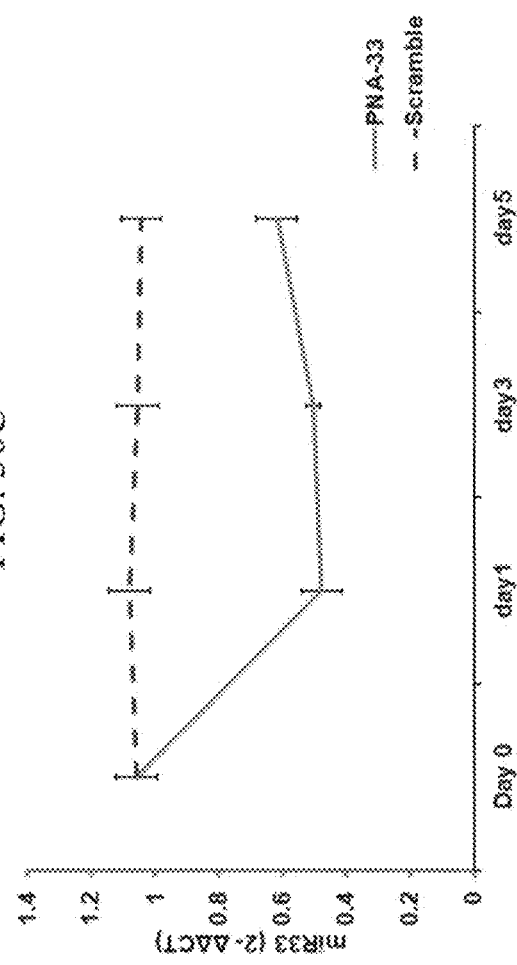
FIG. 36C is a graph of the miR-33 level in BAL macrophages after intranasal delivery of PNA-33, in accordance with some embodiments.

Linking a PNA to pHLIP represents and unique and novel therapeutic approach to target lung macrophages. FIG. 36B shows the feasibility of this technique in targeted therapy. FIG. 36C shows the macrophage specificity of the inhibition of miR-33 by this technique. The level of miR-33 in alveolar macrophages was dramatically decreased one day after a single administration of the inhibitor (intranasally) and remained at low levels for 5 days.

The data obtained from miR-33 macrophage-specific knockout mice confirmed the critical role of macrophages in pulmonary fibrosis. The efficiency and effects of the miR-33 inhibitor on primary macrophages were tested in an in vitro system. The investigation was extended by testing the cell specific delivery of a novel anti miR system. pHLIP-TAMRA conjugated anti miR was administered intravenously to mice and macrophage delivery of the compound in the lungs was confirmed 24 hours after injection using a two-photon microscopy imaging system (FIG. 37). The following experiments were used to determine the role of cell specific miR-33 silencing in pulmonary fibrosis.

1) To identify the most efficient method of cell specific microRNA silencing in murine lung: The microRNA inhibitor was used via intranasal/inhalational/intravenous routes to identify which route is most efficacious in cell specific inhibition.

2) To determine the role of microRNA silencing in lung macrophages as a potential anti-fibrotic therapeutic in pulmonary fibrosis: The minimal efficacious dose of the miR-33 inhibitor was used to evaluate the effect of macrophage specific micro RNA silencing in a bleomycin animal model of pulmonary fibrosis. Similar experiments will be performed in a TFG-β adenovirus-induced lung fibrosis animal model.

3) To elucidate whether a macrophage specific microRNA inhibition as any effects on the metabolic functions of these cells in the animal model of pulmonary fibrosis: The mitochondrial function/morphology was evaluated in isolated macrophages after miR-33 inhibition in lung fibrosis.

Figure 39:
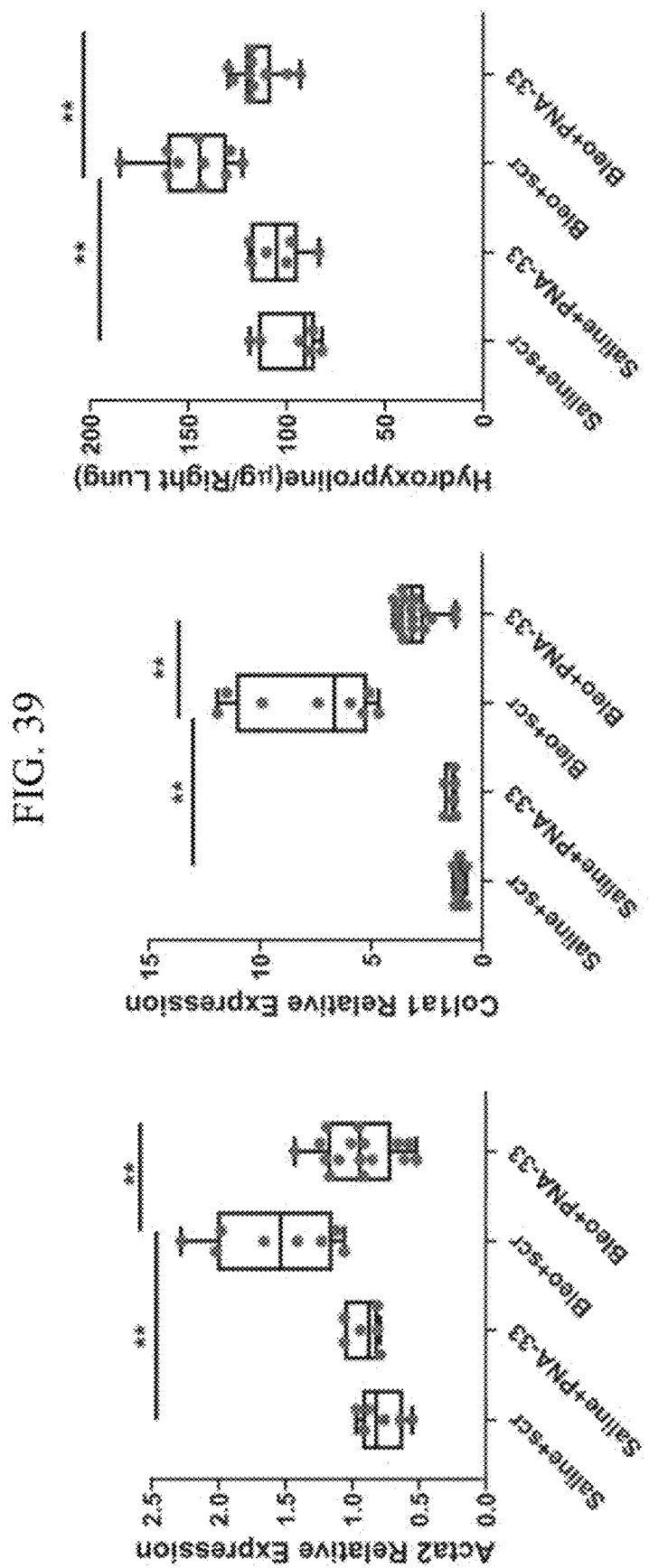
FIG. 39 and FIG. 40 provide results from intranasal delivery of PNA-33, showing inhibition of bleomycin-induced pulmonary fibrosis in mice, in accordance with some embodiments.
Figure 40:
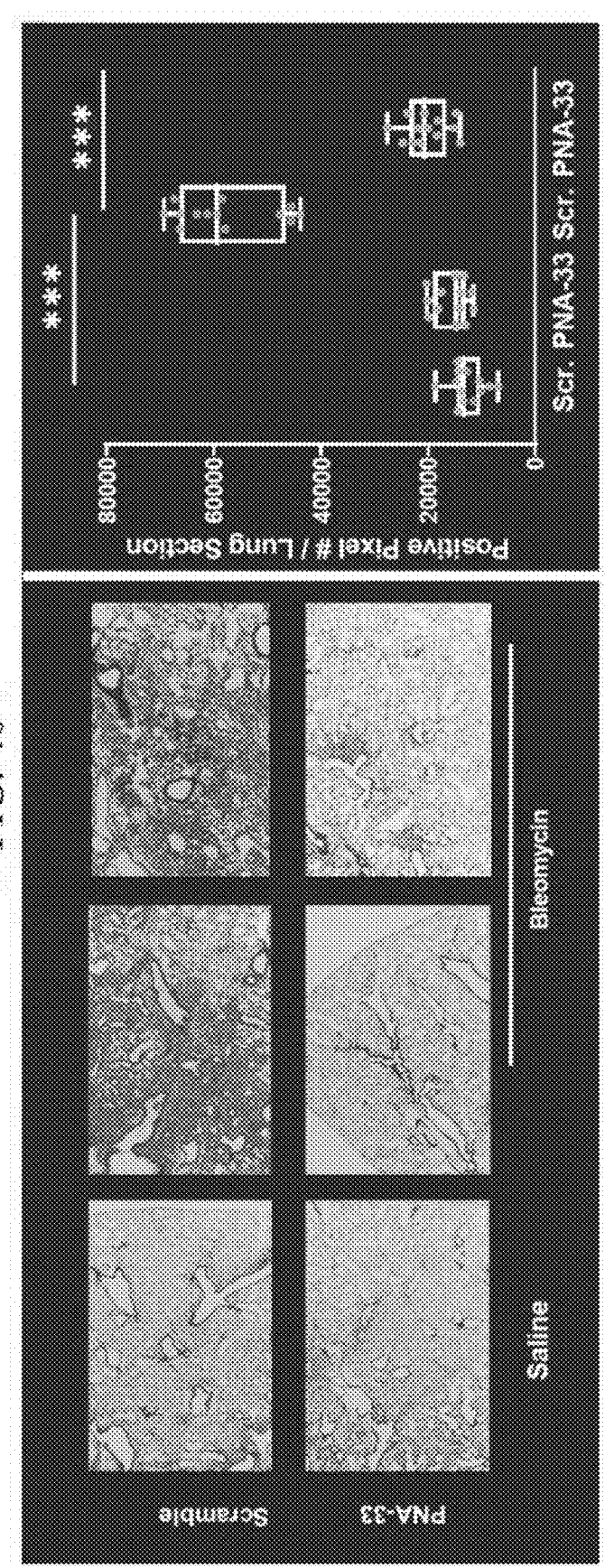

FIG. 38 shows the binding efficiency of inhibitor to the known miR-33 targets by gel shift assay, which confirms the specificity of the inhibitor for this microRNA. FIG. 39 and FIG. 40 show the protective effect of the inhibitor in bleomycin-induced lung fibrosis mice model. miR-33 inhibitor and control were administered intranasally to the WT mice after bleomycin exposure and significant fibro protective effects of this inhibition were identified as indicated by significant decrease collagen content measurements, and fibrogenic gene expressions (col1a1 and Acta2) in the inhibitor treated mice groups (FIG. 39). Histological assessments of these lung sections confirmed these findings (FIG. 40).

Figure 41:
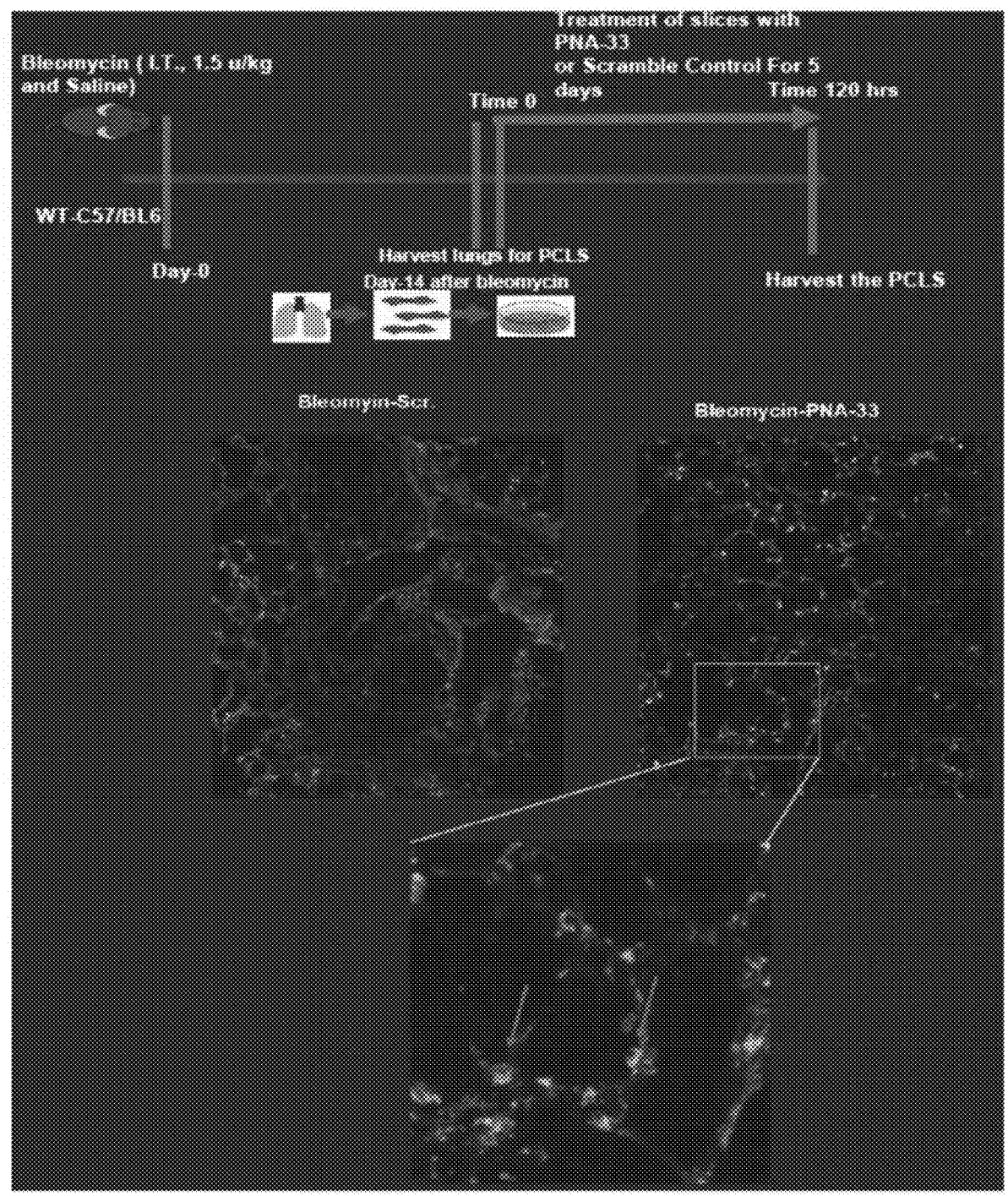
FIG. 41 and FIG. 42 show that PNA-33 inhibits pulmonary fibrosis in murine precision cut lung slices (ex vivo), in accordance with some embodiments.
Figure 42:
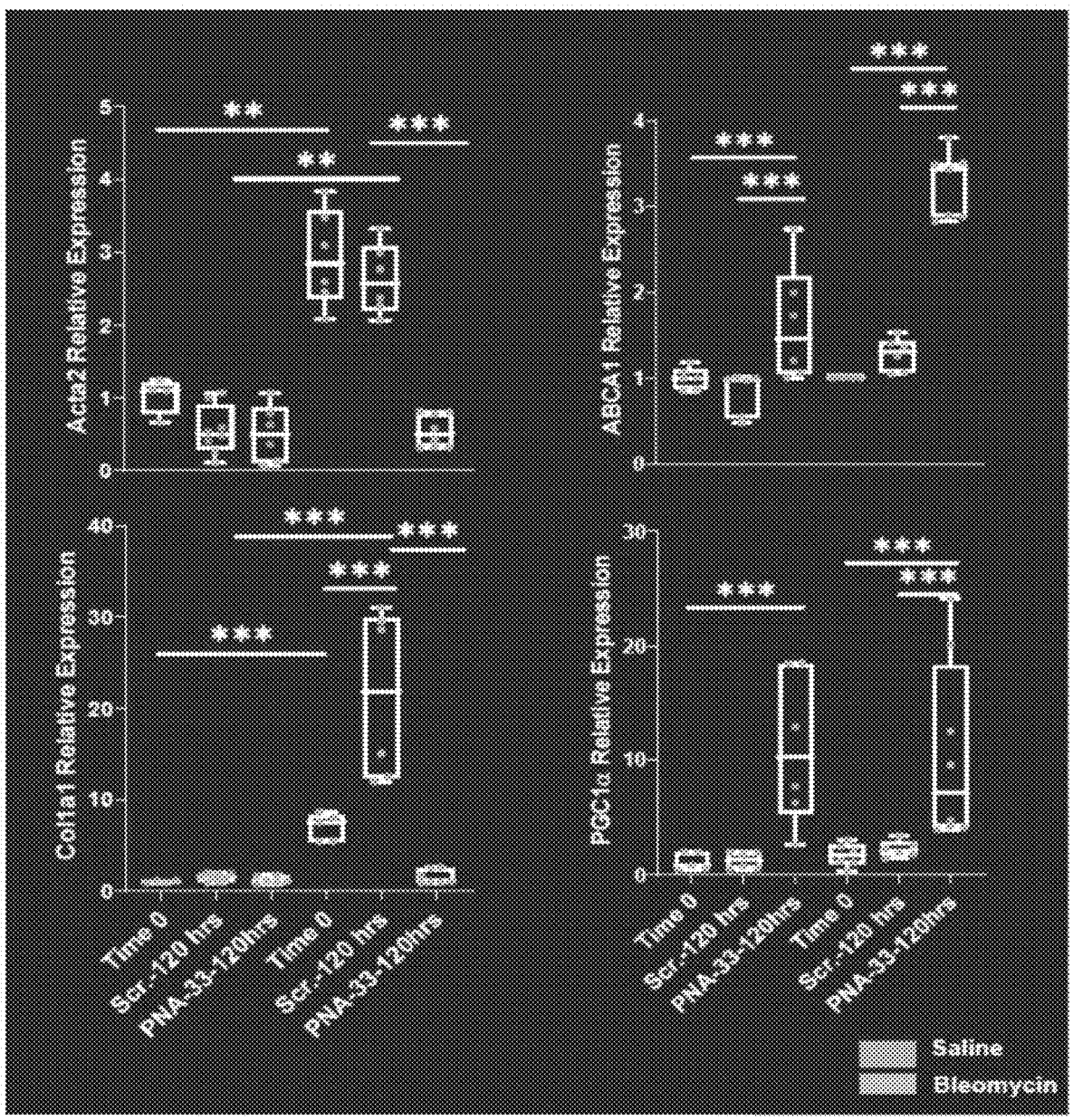
Figure 43:
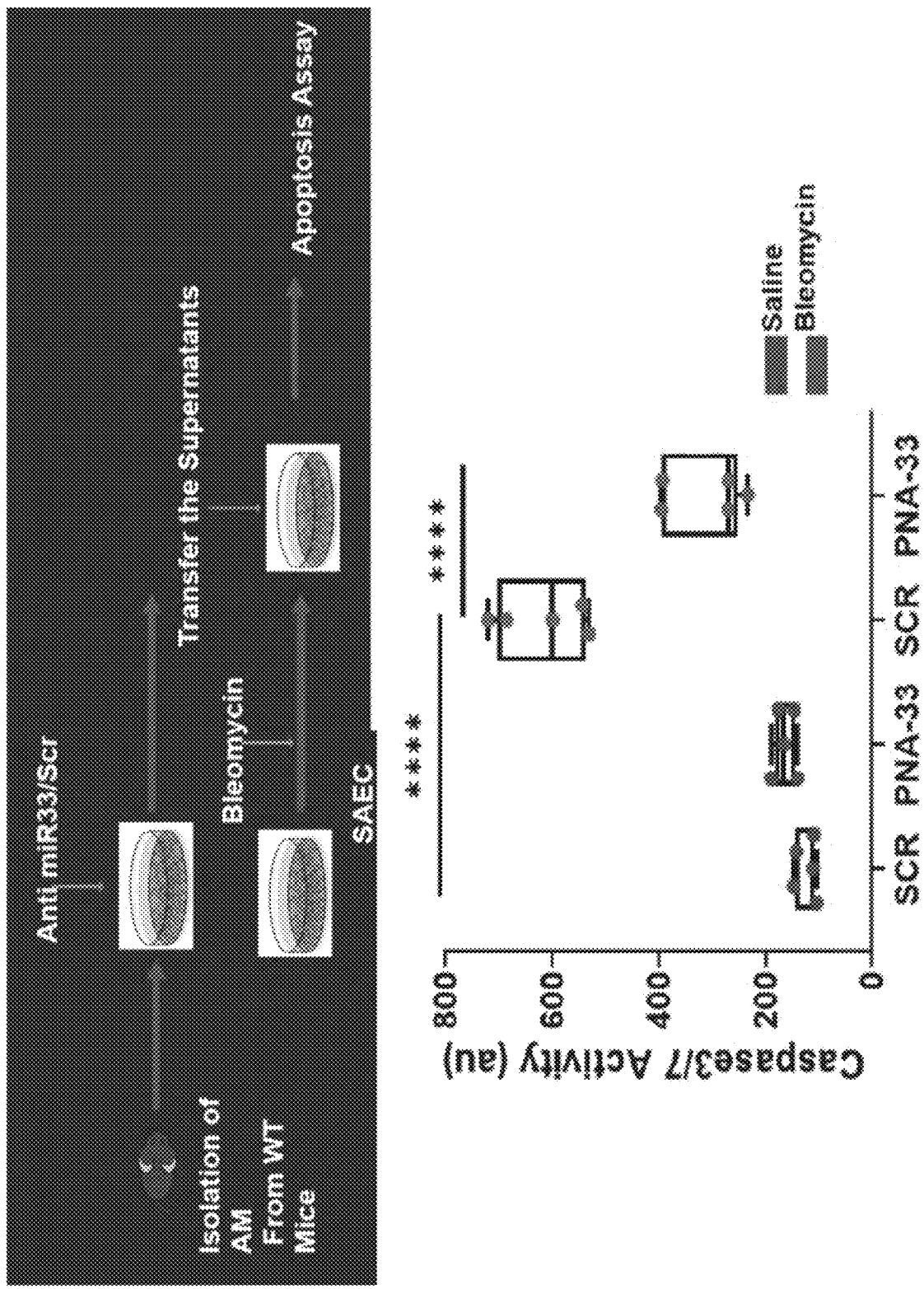
FIG. 43 depicts that miR-33 inhibition in macrophages has an anti-apoptotic effect in epithelial cells, in accordance with some embodiments.

FIG. 41 and FIG. 42 show the fibro protective effects of the inhibitor in murine PCLS generated from the bleomycin induced lung fibrosis model. FIG. 41 depicts the methodic description of this study as well as the imaging of the slices. In brief, the mice lung slices were prepared at day 14 after bleomycin and treated with the inhibitor and/or scramble control for 5 days. The imaging of the inhibitor conjugated to TAMRA identified the successful uptake of the inhibitor by macrophages in PCLS. As it is shown in this image, the inhibitor not only accumulates in the macrophages in mPCLS, but it also attenuates collagen accumulation measured by second harmonic generation microscopy (SHG) compared to control slices. FIG. 43 confirms that the miR-33 inhibition in macrophages has anti-apoptotic effects in epithelial cells. In this experiment the supernatants from the macrophages after miR-33 inhibition was added to the injured epithelial cells. The secretory components in these supernatants, reduced the level of caspase 3/7 activity (markers of the cell death) in the epithelial cells.

Figure 44:
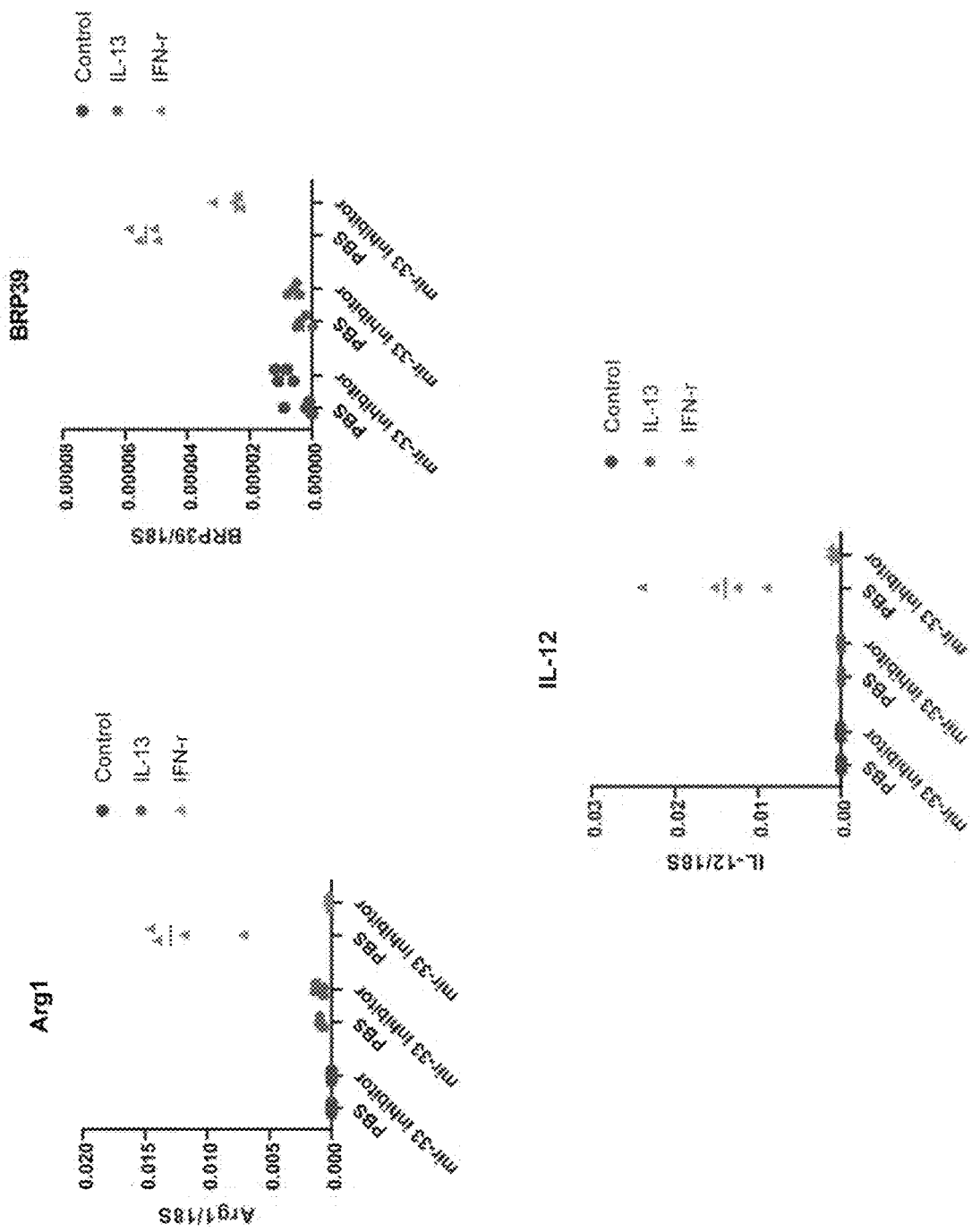
FIG. 44 depicts that the proinflammatory gene expression induced by cytokine (Arg1, IL-12 and BRP39) is reduced after miR-33 inhibition by PNA-33, in accordance with some embodiments.

To confirm the effect of miR-33 inhibition on proinflammatory macrophage phenotypes, primary AM from mice were treated with different cytokines after miR-33 inhibition. FIG. 44 confirms the proinflammatory gene expression induced by cytokine (Arg1, IL-12 and BRP39) is reduced after miR-33 inhibition by PNA-33.

Figure 45:
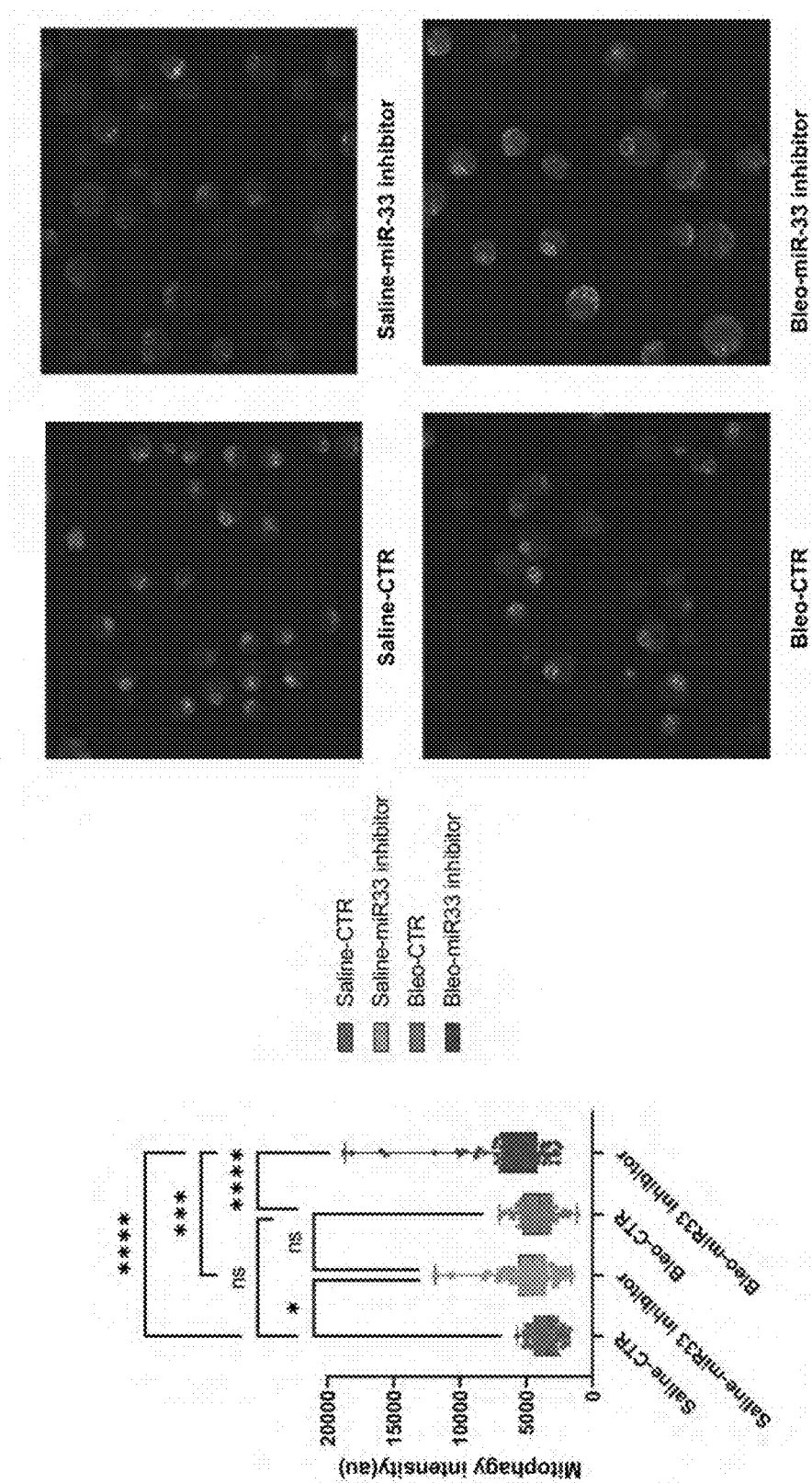
FIG. 45 shows that miR-33 inhibition significantly increases mitophagy at baseline (P value=0.0166) and after bleomycin (P Value<0.0001), in accordance with some embodiments.

To identify the effect of miR-33 inhibition on the process of mitophagy in macrophages, primary AM from mice were isolated and their response to bleomycin was evaluated after miR-33 inhibition. FIG. 45 confirms miR-33 inhibition significantly increases mitophagy at baseline (P value=0.0166) and after bleomycin (P Value<0.0001).

Figure 46:
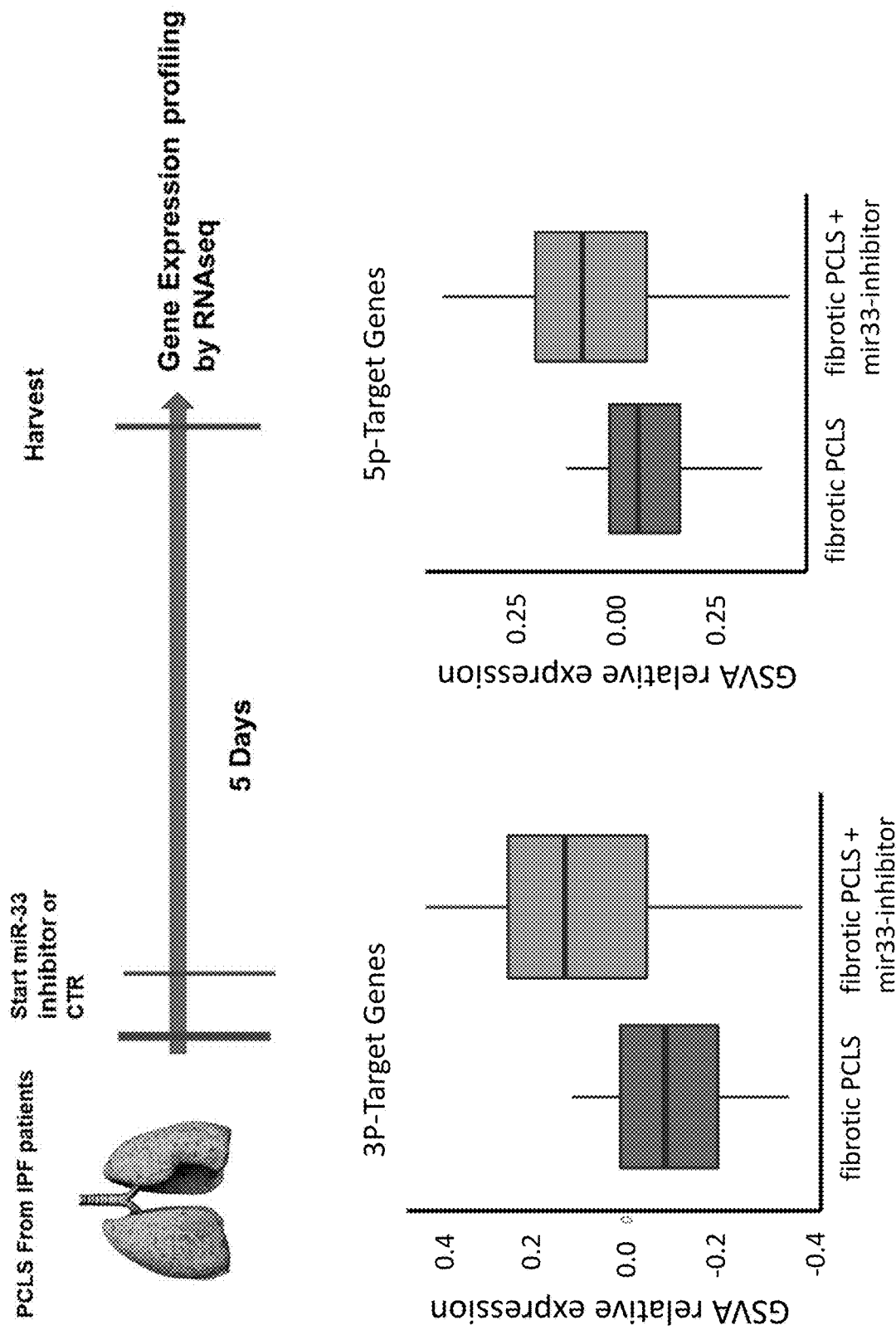
FIG. 46 shows the increases of the miR-33 target genes (3P and 5p) after inhibition, confirming the efficacy of this inhibition, in accordance with some embodiments.
Figure 47:
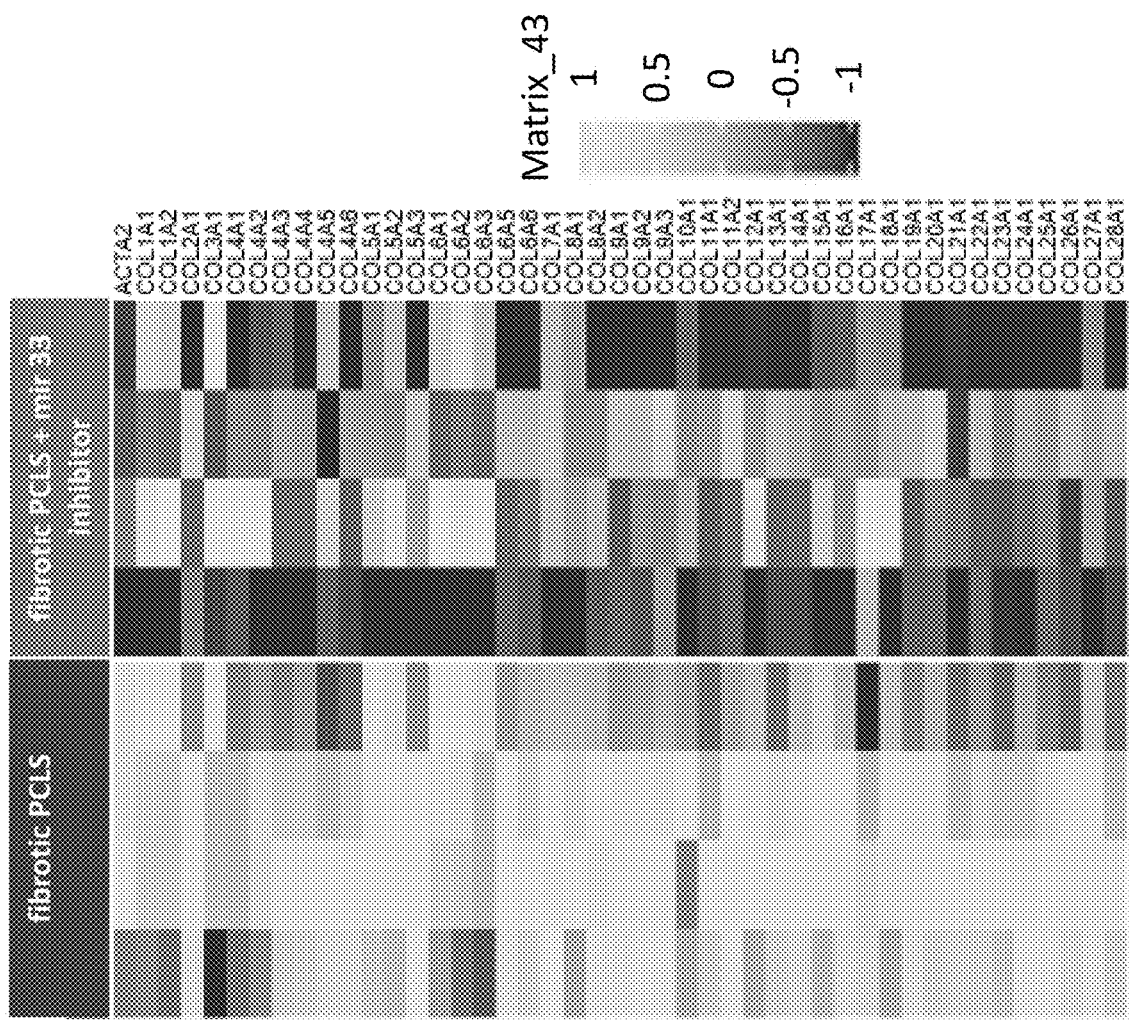
FIG. 47 shows a dramatic decrease in collagen gene expressions in IPF PCLS after miR-33 inhibition, in accordance with some embodiments.
Figure 48:
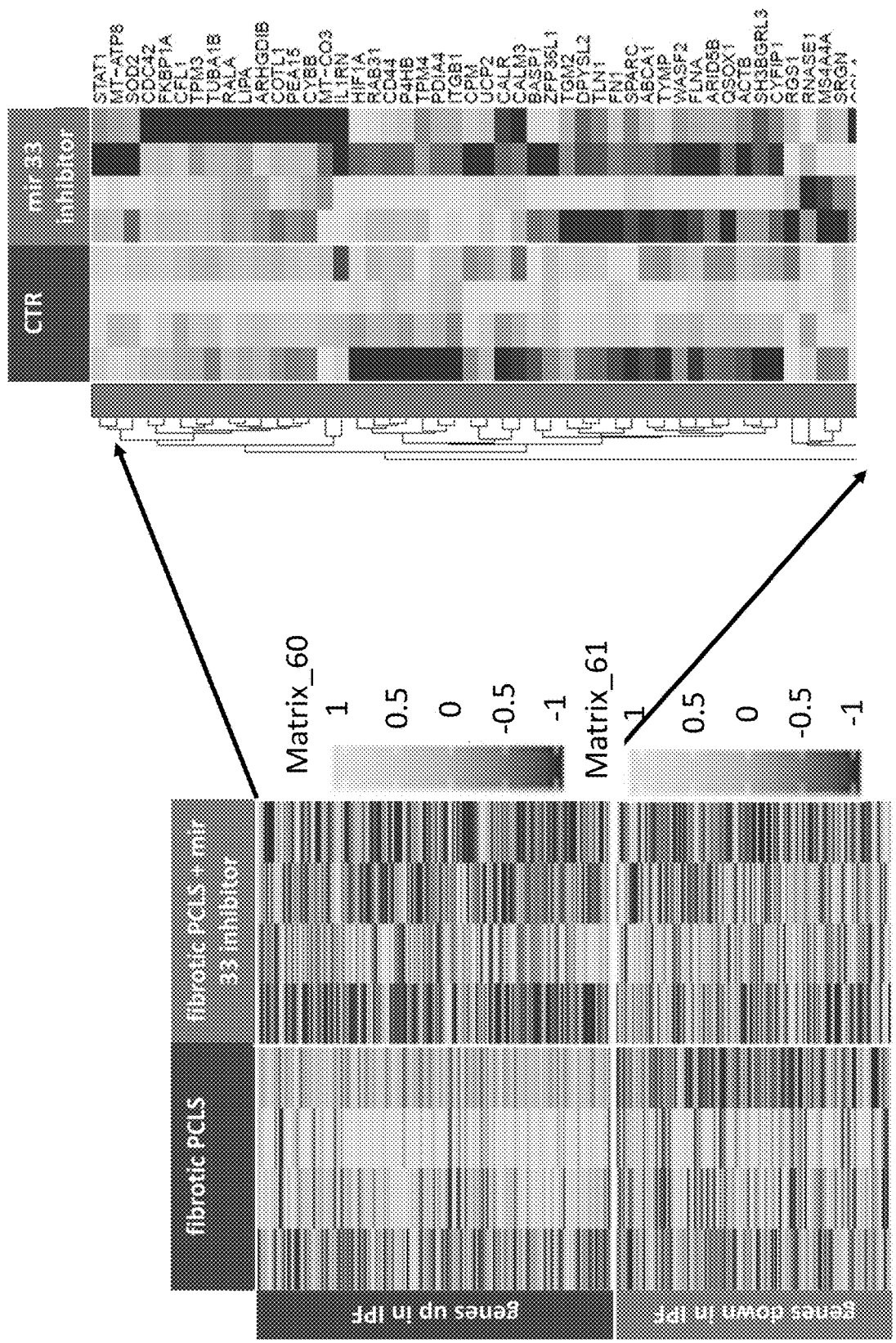
FIG. 48 shows a reversal in profibrotic macrophage gene expressions in IPF PCLS after miR-33, in accordance with some embodiments.

To confirm the therapeutic effect of miR-33 inhibition on human lung fibrosis, the PCLS isolated from IPF patients were treated with miR-33 inhibitor (PNA-33) or Scr. control for 5 days. RNA sequencing on these confirms the profound effects of this inhibition on IPF transcriptomic profile in these samples. FIG. 46 shows the increases of the miR-33 target genes (3P and 5p) after inhibition, confirming the efficacy of this inhibition. FIG. 47 shows a dramatic decrease in collagen gene expressions in IPF PCLS after miR-33 inhibition. FIG.48 identifies a reversal in profibrotic macrophage gene expressions in IPF PCLS after miR-33.

Enumerated Embodiments

In some embodiments, the instant specification is directed to the following non-limiting embodiments:

Embodiment 1

A method of treating pulmonary fibrosis in a subject, the method comprising administering to the subject a therapeutically effective amount of a microRNA-33 (miR-33) inhibitor via a mode of administration selected from nasal, pulmonary, aerosol, inhalational, intratracheal, intrabronchial, intraperitoneal, intravenous, and oral gavage.

Embodiment 2

The method of Embodiment 1, wherein the miR-33 inhibitor is an antisense peptide nucleic acid (PNA) comprising a peptide backbone modified with at least nine nucleobases that are complementary to at least nine contiguous nucleotides in miR-33. Embodiment 3: The method of Embodiment 1 or 2, wherein the miR-33 inhibitor comprises a structure of formula (I)

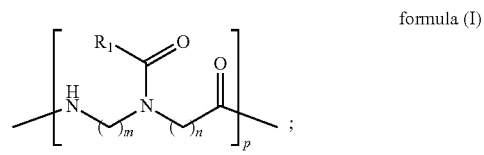

formula (I)

wherein:
    each $R_1$ is independently $(CH_2)_q$-nucleobase;
    m, n, and q are each independently an integer from 1 to 3;
    p is an integer from 5 to 50; and wherein the nucleobase is selected from adenine, guanine, cysteine, thymine, and uracil such that adjacent nucleobases are complementary to contiguous nucleotides in miR-33.

Embodiment 4

The method of Embodiment 3, wherein m is 2, n is 1, and each q is 1.

Embodiment 5

The method of Embodiment 3 or 4, wherein p is an integer from 9 to 17.

Embodiment 6

The method of any one of Embodiments 3-5, wherein p is 17.

Embodiment 7

The method of any one of Embodiments 3-6, wherein the nucleobases comprise the sequence 5'-ATGCAACTACAATGCAA-3' (SEQ ID NO: 1) or the sequence 5'-ATGCAACTACAATGCAA-Cys-SH-3' (SEQ ID NO: 2).

Embodiment 8

The method of any one of Embodiments 3-7, wherein the structure of formula (I) is linked to a pH low insertion peptide (pHLIP).

Embodiment 9

The method of any one of Embodiments 1-8, wherein the pulmonary fibrosis is idiopathic pulmonary fibrosis.

Embodiment 10

The method of any one of Embodiments 1-9, wherein the miR-33 inhibitor is administered to the subject intranasally.

Embodiment 11

The method of claim 10, wherein the miR-33 inhibitor dissolved in saline is administered directly to the lungs of the subject through the subject's nose.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the disclosure. The appended claims are intended to be construed to include all such embodiments and equivalent variations.

What is claimed is:

1. A method of treating, ameliorating, or reducing pulmonary fibrosis in a subject in need thereof, the method comprising administering to the subject a therapeutically effective amount of a microRNA-33 (miR-33) inhibitor via a mode of administration selected from nasal, pulmonary, aerosol, inhalational, intratracheal, intrabronchial, intraperitoneal, intravenous, and oral gavage, wherein the miR-33 inhibitor is an antisense peptide nucleic acid (PNA) comprising a nucleobase sequence set forth in SEQ ID NO:1 (5'-ATGCAACTA-CAATGCAA-3') or SEQ ID NO:2 (5'-ATGCAACTA-CAATGCAA-Cys-SH-3').

2. The method of claim 1, wherein the PNA the comprises a structure of formula (I)

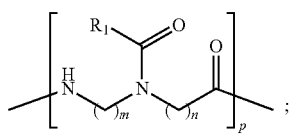

formula (I)

wherein:

each $R_1$ is independently $(CH_2)_q$-nucleobase;

m, n, and q are each independently an integer from 1 to 3; and p is an integer from 17 to 50.

3. The method of claim 2, wherein m is 2, n is 1, and each q is 1.

4. The method of claim 2 or 3, wherein p is 17.

5. The method of claim 1, wherein the PNA is linked to a pH low insertion peptide (pHLIP).

6. The method of claim 1, wherein the pulmonary fibrosis is idiopathic pulmonary fibrosis.

7. The method of claim 1, wherein the miR-33 inhibitor is administered to the subject intranasally.

8. The method of claim 7, wherein the miR-33 inhibitor dissolved in saline is administered directly to the lungs of the subject through the subject's nose.

* * * * *

```
                         SEQUENCE LISTING

<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Nucelic acid portion of antisense peptide
      nucleic acid (PNA)

<400> SEQUENCE: 1
atgcaactac aatgcaa                                                    17

<210> SEQ ID NO 2
<211> LENGTH: 17
<212> TYPE: DNA
<213> ORGANISM: Artificial Sequence
<220> FEATURE:
<223> OTHER INFORMATION: Nucleic acid portion of antisense peptide
      nucleic acid (PNA). Includes a -Cys-SH group at the 3' end

<400> SEQUENCE: 2
atgcaactac aatgcaa                                                    17

<210> SEQ ID NO 3
<211> LENGTH: 17
<212> TYPE: DNA
<213> ORGANISM: Artificial Sequence
<220> FEATURE:
<223> OTHER INFORMATION: Nucleic acid portion of antisense peptide
      nucleic acid (PNA). Includes a -Cys-SH group at the 3' end.

<400> SEQUENCE: 3
tacgctaatc acaaaga                                                    17
```